(12) United States Patent
Bauer et al.

(10) Patent No.: US 7,662,415 B2
(45) Date of Patent: Feb. 16, 2010

(54) MICROBIALLY EXPRESSES XYLANASES AND THEIR USE AS FEED ADDITIVES AND OTHER USES

(75) Inventors: Michael Bauer, Newton, MA (US); Michael Richard Bedford, Wiltshire (GB); Derrick Allen Pulliam, Durham, NC (US)

(73) Assignee: Syngenta Participations AG (CH)

( * ) Notice: Subject to any disclaimer, the term of this patent is extended or adjusted under 35 U.S.C. 154(b) by 350 days.

(21) Appl. No.: 11/821,489

(22) Filed: Jun. 22, 2007

(65) Prior Publication Data

US 2008/0187627 A1  Aug. 7, 2008

Related U.S. Application Data

(62) Division of application No. 11/018,645, filed on Dec. 20, 2004, now Pat. No. 7,291,493.

(60) Provisional application No. 60/531,404, filed on Dec. 19, 2003.

(51) Int. Cl.
| | |
|---|---|
| A23K 3/00 | (2006.01) |
| C12N 9/24 | (2006.01) |
| C12N 9/00 | (2006.01) |
| C12P 21/06 | (2006.01) |
| A61K 38/43 | (2006.01) |
| A61K 38/54 | (2006.01) |
| C07H 21/04 | (2006.01) |

(52) U.S. Cl. .............. 426/53; 426/54; 426/56; 435/200; 435/183; 435/69.1; 424/94.1; 424/94.2; 536/23.2

(58) Field of Classification Search .................. None
See application file for complete search history.

(56) References Cited

U.S. PATENT DOCUMENTS 5,437,992 A  8/1995 Bodie et al.
6,228,629 B1  5/2001 Paloheimo et al.

FOREIGN PATENT DOCUMENTS

| EP | 1 184 460 | 3/2002 |
| WO | WO00/29587 | 5/2000 |
| WO | WO03/106654 | 12/2003 |

OTHER PUBLICATIONS

U.S. Appl. No. 10/463,720, Short, et al.
Bedford, M.R. & Classen, H.L., An in vitro Assay for Prediction of Broiler Intestinal Viscosity and Growth When Fed Rye-Based Diets in the Presence of Exogeneous Enzymes *Poultry Science*, vol. 72 (1993) pp. 137-143.
Biely et al., "*Proceedings of the second Tricel Symposium on Trichoderma reesei Cellulases and Other Hydrolases*," Espoo 1993, P. Souminen and T. Reinikainen eds., Foundation for Biotechnical and Industrial Fermentation Research 8:125-135.
Collins et al, Xylanases, Xylanase Families and Extremophilic Xylanases *Federation of European Microbiological Societies Microbiology Reviews*, vol. 29 (2005) p. 3-23.
Kulkarni et al, *Molecular and Biotechnological Aspects of Xylanases Federation of European Microbiological Societies Microbiology Reviews*, vol. 23 (1999) p. 411-456.
Tenkanen et al, *Two Major Xylanases of Trichoderma reesei Enzyme and Microbial Technology*, vol. 14 (1992) pp. 566-574.
Törrönen et al, *The Two Major Xylanases from Trichoderma reesei: Characterization of Both Enzymes and Genes Bio/Technology*, vol. 10 (1992) pp. 1461-1465.
Wong et al, *Multiplicity of $\beta$-1, 4-Xylanase in Microorganisms: Functions and Applications Microbiological Reviews*, vol. 52 (1988) pp. 305-317.
Xu et al, *A third xylanase from Trichoderma reesei PC-3-7 Applied Microbiological Biotechnology*, vol. 49 (1998) pp. 718-724.
Inagaki, K. et al. Gene cloning and characterization of an acidic xylanase from *Acidobacterium capsulatum*. Biosci. Biotechnol. Biochem, 1998, vol. 62, No. 6, pp. 1061-1067.

*Primary Examiner*—Ganapathirama Raghu
(74) *Attorney, Agent, or Firm*—Joshua Price

(57) ABSTRACT

The present invention relates to codon-optimized xylanase coding sequences and the expression of xylanases in microbes and yeast. The invention further relates to using multiple copies of the xylanase expression construct for high levels of protein expression. The invention also relates to the use of xylanases as feed or food additives. The invention also relates to methods of expression of enzymes to increase thermotolerance by expressing them in organisms that glycosylate proteins compared to expression that the same enzyme without the glycosylation. Further, the invention relates to methods of preparing feed, enzyme feed additives, and methods of reducing the feed conversion ration or increasing weight gain of animals.

12 Claims, 5 Drawing Sheets

SEQUENCE LISTING

```
<160> NUMBER OF SEQ ID NOS: 39

<210> SEQ ID NO 1
<211> LENGTH: 555
<212> TYPE: DNA
<213> ORGANISM: artificial sequence
<220> FEATURE:
<223> OTHER INFORMATION: xylanase coding region of PP6002
<220> FEATURE:
<221> NAME/KEY: CDS
<222> LOCATION: (1)..(555)
<220> FEATURE:
<221> NAME/KEY: msic_feature
<222> LOCATION: (1)..(555)

<400> SEQUENCE: 1 gca tct act gac tac tgg cag aac tgg act gac ggt ggt ggt acc gtg      48
Ala Ser Thr Asp Tyr Trp Gln Asn Trp Thr Asp Gly Gly Gly Thr Val
1               5                   10                  15 aac gct act aat ggt agt gat ggt aat tac tca gtt tct tgg tca aac      96
Asn Ala Thr Asn Gly Ser Asp Gly Asn Tyr Ser Val Ser Trp Ser Asn
            20                  25                  30 tgt gga aac ttc gtc gtt ggt aag gga tgg aca acc gga tct gct act     144
Cys Gly Asn Phe Val Val Gly Lys Gly Trp Thr Thr Gly Ser Ala Thr
        35                  40                  45 aga gta atc aac tac aat gcc gga gct ttt tct cct tct ggt aat ggt     192
Arg Val Ile Asn Tyr Asn Ala Gly Ala Phe Ser Pro Ser Gly Asn Gly
    50                  55                  60 tac ttg gcc ttg tat gga tgg aca aga aac tct ttg att gaa tat tac     240
Tyr Leu Ala Leu Tyr Gly Trp Thr Arg Asn Ser Leu Ile Glu Tyr Tyr
65                  70                  75                  80 gtt gtg gat tcc tgg ggt act tat cgt cca act gga aca tat aaa ggt     288
Val Val Asp Ser Trp Gly Thr Tyr Arg Pro Thr Gly Thr Tyr Lys Gly
                85                  90                  95 act gta act tct gac gga ggt acc tat gat att tac aca act aca aga     336
Thr Val Thr Ser Asp Gly Gly Thr Tyr Asp Ile Tyr Thr Thr Thr Arg
            100                 105                 110 act aat gct cca tct atc gac gga aat aac act aca ttt acc cag ttt     384
Thr Asn Ala Pro Ser Ile Asp Gly Asn Asn Thr Thr Phe Thr Gln Phe
        115                 120                 125 tgg tct gtc aga caa tct aaa aga cct att gga act aat aat acc ata     432
Trp Ser Val Arg Gln Ser Lys Arg Pro Ile Gly Thr Asn Asn Thr Ile
    130                 135                 140 act ttc agt aat cat gtt aac gct tgg aag tca aaa ggt atg aac ttg     480
Thr Phe Ser Asn His Val Asn Ala Trp Lys Ser Lys Gly Met Asn Leu
145                 150                 155                 160 ggt tcc tcc tgg tcc tac caa gtt ttg gca act gag ggt tac caa tct     528
Gly Ser Ser Trp Ser Tyr Gln Val Leu Ala Thr Glu Gly Tyr Gln Ser
                165                 170                 175
```

-continued

```
agt ggt tat tca aat gtt act gtc tgg                                      555
Ser Gly Tyr Ser Asn Val Thr Val Trp
        180                 185

<210> SEQ ID NO 2
<211> LENGTH: 185
<212> TYPE: PRT
<213> ORGANISM: artificial sequence
<220> FEATURE:
<223> OTHER INFORMATION: xylanase coding region of PP6002

<400> SEQUENCE: 2

Ala Ser Thr Asp Tyr Trp Gln Asn Trp Thr Asp Gly Gly Thr Val
1               5                   10                  15

Asn Ala Thr Asn Gly Ser Asp Gly Asn Tyr Ser Val Ser Trp Ser Asn
                20                  25                  30

Cys Gly Asn Phe Val Val Gly Lys Gly Trp Thr Thr Gly Ser Ala Thr
            35                  40                  45

Arg Val Ile Asn Tyr Asn Ala Gly Ala Phe Ser Pro Ser Gly Asn Gly
        50                  55                  60

Tyr Leu Ala Leu Tyr Gly Trp Thr Arg Asn Ser Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Thr Ser Asp Gly Gly Thr Tyr Asp Ile Tyr Thr Thr Thr Arg
            100                 105                 110

Thr Asn Ala Pro Ser Ile Asp Gly Asn Asn Thr Phe Thr Gln Phe
        115                 120                 125

Trp Ser Val Arg Gln Ser Lys Arg Pro Ile Gly Thr Asn Asn Thr Ile
130                 135                 140

Thr Phe Ser Asn His Val Asn Ala Trp Lys Ser Lys Gly Met Asn Leu
145                 150                 155                 160

Gly Ser Ser Trp Ser Tyr Gln Val Leu Ala Thr Glu Gly Tyr Gln Ser
                165                 170                 175

Ser Gly Tyr Ser Asn Val Thr Val Trp
        180                 185

<210> SEQ ID NO 3
<211> LENGTH: 591
<212> TYPE: DNA
<213> ORGANISM: artificial sequence
<220> FEATURE:
<223> OTHER INFORMATION: xylanase coding region of PP6016
<220> FEATURE:
<221> NAME/KEY: CDS
<222> LOCATION: (1)..(591)
<220> FEATURE:
<221> NAME/KEY: misc_feature
<222> LOCATION: (1)..(591)

<400> SEQUENCE: 3 gct cag act atc tgt tct aac cag act ggt act aat aac gga tat ttt     48
Ala Gln Thr Ile Cys Ser Asn Gln Thr Gly Thr Asn Asn Gly Tyr Phe
1               5                   10                  15 tac tca ttt tgg aag gac act ggt tct gca tgc atg acc ctt ggt tcc     96
Tyr Ser Phe Trp Lys Asp Thr Gly Ser Ala Cys Met Thr Leu Gly Ser
                20                  25                  30 gga gga aac tat tct gtt aat tgg aac ttg ggt tct ggt aat atg gtc    144
Gly Gly Asn Tyr Ser Val Asn Trp Asn Leu Gly Ser Gly Asn Met Val
            35                  40                  45 tgt ggt aag gga tgg tct acc gga tct tca tca aga aga atc ggt tac    192
Cys Gly Lys Gly Trp Ser Thr Gly Ser Ser Ser Arg Arg Ile Gly Tyr
```

```
Cys Gly Lys Gly Trp Ser Thr Gly Ser Ser Ser Arg Arg Ile Gly Tyr
     50                  55                  60 aac gca gga gtt tgg gcc cca aac ggt aac gct tac ttg aca ttg tat       240
Asn Ala Gly Val Trp Ala Pro Asn Gly Asn Ala Tyr Leu Thr Leu Tyr
65                   70                  75                  80 ggt tgg act agg aac cct ttg ata gaa tac tac gtc gta gat agt tgg       288
Gly Trp Thr Arg Asn Pro Leu Ile Glu Tyr Tyr Val Val Asp Ser Trp
                     85                  90                  95 gga tca tgg cgt cct cca ggt gga act tca gct ggt acc gta aat tcc       336
Gly Ser Trp Arg Pro Pro Gly Gly Thr Ser Ala Gly Thr Val Asn Ser
                 100                 105                 110 gat gga ggt act tat aat tta tac aga act caa agg gtg aac gct cca       384
Asp Gly Gly Thr Tyr Asn Leu Tyr Arg Thr Gln Arg Val Asn Ala Pro
             115                 120                 125 tct att gat ggt acc aga act ttt tac caa tat tgg tcc gtt aga aca       432
Ser Ile Asp Gly Thr Arg Thr Phe Tyr Gln Tyr Trp Ser Val Arg Thr
         130                 135                 140 agt aaa cgt cct act gga tct aat cag aca att aca ttc gca aat cat       480
Ser Lys Arg Pro Thr Gly Ser Asn Gln Thr Ile Thr Phe Ala Asn His
145                 150                 155                 160 gtt aat gct tgg aga tcc aaa ggt tgg aat ctg ggt tct cac gtg tac       528
Val Asn Ala Trp Arg Ser Lys Gly Trp Asn Leu Gly Ser His Val Tyr
                     165                 170                 175 caa att atg gcc act gag ggt tat caa tct agt gga aat tct aat ttg       576
Gln Ile Met Ala Thr Glu Gly Tyr Gln Ser Ser Gly Asn Ser Asn Leu
                 180                 185                 190 aca gtt tgg gct caa                                                    591
Thr Val Trp Ala Gln
             195

<210> SEQ ID NO 4
<211> LENGTH: 197
<212> TYPE: PRT
<213> ORGANISM: artificial sequence
<220> FEATURE:
<223> OTHER INFORMATION: xylanase coding region of PP6016

<400> SEQUENCE: 4

Ala Gln Thr Ile Cys Ser Asn Gln Thr Gly Thr Asn Gly Tyr Phe
1               5                   10                  15

Tyr Ser Phe Trp Lys Asp Thr Gly Ser Ala Cys Met Thr Leu Gly Ser
                 20                  25                  30

Gly Gly Asn Tyr Ser Val Asn Trp Asn Leu Gly Ser Gly Asn Met Val
             35                  40                  45

Cys Gly Lys Gly Trp Ser Thr Gly Ser Ser Ser Arg Arg Ile Gly Tyr
         50                  55                  60

Asn Ala Gly Val Trp Ala Pro Asn Gly Asn Ala Tyr Leu Thr Leu Tyr
65                   70                  75                  80

Gly Trp Thr Arg Asn Pro Leu Ile Glu Tyr Tyr Val Val Asp Ser Trp
                     85                  90                  95

Gly Ser Trp Arg Pro Pro Gly Gly Thr Ser Ala Gly Thr Val Asn Ser
                 100                 105                 110

Asp Gly Gly Thr Tyr Asn Leu Tyr Arg Thr Gln Arg Val Asn Ala Pro
             115                 120                 125

Ser Ile Asp Gly Thr Arg Thr Phe Tyr Gln Tyr Trp Ser Val Arg Thr
         130                 135                 140

Ser Lys Arg Pro Thr Gly Ser Asn Gln Thr Ile Thr Phe Ala Asn His
145                 150                 155                 160
```

Val Asn Ala Trp Arg Ser Lys Gly Trp Asn Leu Gly Ser His Val Tyr
            165                 170                 175

Gln Ile Met Ala Thr Glu Gly Tyr Gln Ser Ser Gly Asn Ser Asn Leu
        180                 185                 190

Thr Val Trp Ala Gln
        195

<210> SEQ ID NO 5
<211> LENGTH: 972
<212> TYPE: DNA
<213> ORGANISM: artificial sequence
<220> FEATURE:
<223> OTHER INFORMATION: xylanase coding region of PP6407
<220> FEATURE:
<221> NAME/KEY: CDS
<222> LOCATION: (1)..(972)
<220> FEATURE:
<221> NAME/KEY: msic_feature
<222> LOCATION: (1)..(972)

<400> SEQUENCE: 5

| gca | caa | act | ttg | aac | aac | aac | tcc | act | gga | act | cac | gac | ggt | ttt | tat | 48 |
|-----|-----|-----|-----|-----|-----|-----|-----|-----|-----|-----|-----|-----|-----|-----|-----|----|
| Ala | Gln | Thr | Leu | Asn | Asn | Asn | Ser | Thr | Gly | Thr | His | Asp | Gly | Phe | Tyr |    |
| 1   |     |     |     | 5   |     |     |     |     | 10  |     |     |     |     | 15  |     |    |

| tac | aca | ttt | tgg | aaa | gac | tct | ggt | tct | gct | tcc | atg | acc | ctt | cac | cct | 96 |
|-----|-----|-----|-----|-----|-----|-----|-----|-----|-----|-----|-----|-----|-----|-----|-----|----|
| Tyr | Thr | Phe | Trp | Lys | Asp | Ser | Gly | Ser | Ala | Ser | Met | Thr | Leu | His | Pro |    |
|     |     |     | 20  |     |     |     |     | 25  |     |     |     |     | 30  |     |     |    |

| ggt | gga | aga | tat | tca | tca | cag | tgg | aca | tct | aac | act | aac | aat | tgg | gtt | 144 |
|-----|-----|-----|-----|-----|-----|-----|-----|-----|-----|-----|-----|-----|-----|-----|-----|-----|
| Gly | Gly | Arg | Tyr | Ser | Ser | Gln | Trp | Thr | Ser | Asn | Thr | Asn | Asn | Trp | Val |     |
|     |     | 35  |     |     |     |     | 40  |     |     |     |     | 45  |     |     |     |     |

| ggt | ggt | aag | ggt | tgg | aac | cct | gga | ggt | cct | aga | gta | gtt | aac | tac | agt | 192 |
|-----|-----|-----|-----|-----|-----|-----|-----|-----|-----|-----|-----|-----|-----|-----|-----|-----|
| Gly | Gly | Lys | Gly | Trp | Asn | Pro | Gly | Gly | Pro | Arg | Val | Val | Asn | Tyr | Ser |     |
| 50  |     |     |     |     | 55  |     |     |     |     | 60  |     |     |     |     |     |     |

| gga | tat | tac | ggt | gtt | aat | aac | tcc | caa | aac | tcc | tac | ctt | gcc | ttg | tac | 240 |
|-----|-----|-----|-----|-----|-----|-----|-----|-----|-----|-----|-----|-----|-----|-----|-----|-----|
| Gly | Tyr | Tyr | Gly | Val | Asn | Asn | Ser | Gln | Asn | Ser | Tyr | Leu | Ala | Leu | Tyr |     |
| 65  |     |     |     |     | 70  |     |     |     |     | 75  |     |     |     |     | 80  |     |

| ggt | tgg | act | cgt | aat | cct | ttg | gtg | gaa | tac | tac | gtt | att | gag | agt | tac | 288 |
|-----|-----|-----|-----|-----|-----|-----|-----|-----|-----|-----|-----|-----|-----|-----|-----|-----|
| Gly | Trp | Thr | Arg | Asn | Pro | Leu | Val | Glu | Tyr | Tyr | Val | Ile | Glu | Ser | Tyr |     |
|     |     |     |     | 85  |     |     |     |     | 90  |     |     |     |     | 95  |     |     |

| ggt | tct | tac | aat | cca | gca | tcc | tgt | gct | gga | gga | gtt | gat | tat | ggt | tcc | 336 |
|-----|-----|-----|-----|-----|-----|-----|-----|-----|-----|-----|-----|-----|-----|-----|-----|-----|
| Gly | Ser | Tyr | Asn | Pro | Ala | Ser | Cys | Ala | Gly | Gly | Val | Asp | Tyr | Gly | Ser |     |
|     |     |     | 100 |     |     |     |     | 105 |     |     |     |     | 110 |     |     |     |

| ttc | caa | tct | gac | ggt | gct | acc | tat | aac | gta | aga | agg | tgc | ttg | aga | caa | 384 |
|-----|-----|-----|-----|-----|-----|-----|-----|-----|-----|-----|-----|-----|-----|-----|-----|-----|
| Phe | Gln | Ser | Asp | Gly | Ala | Thr | Tyr | Asn | Val | Arg | Arg | Cys | Leu | Arg | Gln |     |
|     |     | 115 |     |     |     |     | 120 |     |     |     |     | 125 |     |     |     |     |

| aat | gct | cca | agt | atc | gaa | ggt | aat | aac | tct | aca | ttt | tac | cag | tac | ttt | 432 |
|-----|-----|-----|-----|-----|-----|-----|-----|-----|-----|-----|-----|-----|-----|-----|-----|-----|
| Asn | Ala | Pro | Ser | Ile | Glu | Gly | Asn | Asn | Ser | Thr | Phe | Tyr | Gln | Tyr | Phe |     |
|     | 130 |     |     |     |     | 135 |     |     |     |     | 140 |     |     |     |     |     |

| tca | gtt | cgt | aat | cca | aag | aag | ggt | ttc | ggt | aat | att | tct | ggt | act | att | 480 |
|-----|-----|-----|-----|-----|-----|-----|-----|-----|-----|-----|-----|-----|-----|-----|-----|-----|
| Ser | Val | Arg | Asn | Pro | Lys | Lys | Gly | Phe | Gly | Asn | Ile | Ser | Gly | Thr | Ile |     |
| 145 |     |     |     |     | 150 |     |     |     |     | 155 |     |     |     |     | 160 |     |

| acc | gtc | gct | aat | cat | ttt | aat | tat | tgg | gca | tcc | aga | ggt | ctg | aac | tta | 528 |
|-----|-----|-----|-----|-----|-----|-----|-----|-----|-----|-----|-----|-----|-----|-----|-----|-----|
| Thr | Val | Ala | Asn | His | Phe | Asn | Tyr | Trp | Ala | Ser | Arg | Gly | Leu | Asn | Leu |     |
|     |     |     |     | 165 |     |     |     |     | 170 |     |     |     |     | 175 |     |     |

| gga | aac | cat | gat | tat | atg | gtt | ttc | gcc | act | gaa | ggt | tat | caa | tct | caa | 576 |
|-----|-----|-----|-----|-----|-----|-----|-----|-----|-----|-----|-----|-----|-----|-----|-----|-----|
| Gly | Asn | His | Asp | Tyr | Met | Val | Phe | Ala | Thr | Glu | Gly | Tyr | Gln | Ser | Gln |     |
|     |     |     | 180 |     |     |     |     | 185 |     |     |     |     | 190 |     |     |     |

| ggt | tct | agt | gat | att | act | gtg | tca | agt | ggt | act | gga | ggt | gga | gga | 624 |
|-----|-----|-----|-----|-----|-----|-----|-----|-----|-----|-----|-----|-----|-----|-----|-----|
| Gly | Ser | Ser | Asp | Ile | Thr | Val | Ser | Ser | Gly | Thr | Gly | Gly | Gly | Gly |     |
|     | 195 |     |     |     |     | 200 |     |     |     |     | 205 |     |     |     |     |

| gga | gga | aat | acc | gga | tct | aaa | aca | ata | gtc | gtc | aga | gcc | aga | ggt | acc | 672 |
|-----|-----|-----|-----|-----|-----|-----|-----|-----|-----|-----|-----|-----|-----|-----|-----|-----|
| Gly | Gly | Asn | Thr | Gly | Ser | Lys | Thr | Ile | Val | Val | Arg | Ala | Arg | Gly | Thr |     |

```
                210                 215                 220
gca ggt gga gag aat ata tcc ttg aag gta aat aat gcc act atc gct   720
Ala Gly Gly Glu Asn Ile Ser Leu Lys Val Asn Asn Ala Thr Ile Ala
225                 230                 235                 240 tca tgg acc ttg aca act tca atg gct aac tac aca gct act aca tct   768
Ser Trp Thr Leu Thr Thr Ser Met Ala Asn Tyr Thr Ala Thr Thr Ser
            245                 250                 255 gct tct ggt gga tct ctg gtt gag ttc act aac gat gga ggt aat aga   816
Ala Ser Gly Gly Ser Leu Val Glu Phe Thr Asn Asp Gly Gly Asn Arg
        260                 265                 270 gat gtt caa gtg gac tat tta tca gtc aat ggt gct gtc aga caa gca   864
Asp Val Gln Val Asp Tyr Leu Ser Val Asn Gly Ala Val Arg Gln Ala
    275                 280                 285 gaa gat cag act tat aat act ggt gtg tat cag aac gga cag tgc gga   912
Glu Asp Gln Thr Tyr Asn Thr Gly Val Tyr Gln Asn Gly Gln Cys Gly
290                 295                 300 ggt gga aac gga agg tct gag tgg ttg cat tgt aac ggt gcc att gga   960
Gly Gly Asn Gly Arg Ser Glu Trp Leu His Cys Asn Gly Ala Ile Gly
305                 310                 315                 320 ttt ggt aat ttg                                                   972
Phe Gly Asn Leu <210> SEQ ID NO 6
<211> LENGTH: 324
<212> TYPE: PRT
<213> ORGANISM: artificial sequence
<220> FEATURE:
<223> OTHER INFORMATION: xylanase coding region of PP6407

<400> SEQUENCE: 6

Ala Gln Thr Leu Asn Asn Asn Ser Thr Gly Thr His Asp Gly Phe Tyr
1               5                   10                  15

Tyr Thr Phe Trp Lys Asp Ser Gly Ser Ala Ser Met Thr Leu His Pro
            20                  25                  30

Gly Gly Arg Tyr Ser Ser Gln Trp Thr Ser Asn Thr Asn Asn Trp Val
        35                  40                  45

Gly Gly Lys Gly Trp Asn Pro Gly Gly Pro Arg Val Val Asn Tyr Ser
    50                  55                  60

Gly Tyr Tyr Gly Val Asn Asn Ser Gln Asn Ser Tyr Leu Ala Leu Tyr
65                  70                  75                  80

Gly Trp Thr Arg Asn Pro Leu Val Glu Tyr Tyr Val Ile Glu Ser Tyr
                85                  90                  95

Gly Ser Tyr Asn Pro Ala Ser Cys Ala Gly Gly Val Asp Tyr Gly Ser
            100                 105                 110

Phe Gln Ser Asp Gly Ala Thr Tyr Asn Val Arg Arg Cys Leu Arg Gln
        115                 120                 125

Asn Ala Pro Ser Ile Glu Gly Asn Asn Ser Thr Phe Tyr Gln Tyr Phe
    130                 135                 140

Ser Val Arg Asn Pro Lys Lys Gly Phe Gly Asn Ile Ser Gly Thr Ile
145                 150                 155                 160

Thr Val Ala Asn His Phe Asn Tyr Trp Ala Ser Arg Gly Leu Asn Leu
                165                 170                 175

Gly Asn His Asp Tyr Met Val Phe Ala Thr Glu Gly Tyr Gln Ser Gln
            180                 185                 190

Gly Ser Ser Asp Ile Thr Val Ser Ser Gly Thr Gly Gly Gly Gly
        195                 200                 205

Gly Gly Asn Thr Gly Ser Lys Thr Ile Val Val Arg Ala Arg Gly Thr
```

```
                210                 215                 220
Ala Gly Gly Glu Asn Ile Ser Leu Lys Val Asn Asn Ala Thr Ile Ala
225                 230                 235                 240

Ser Trp Thr Leu Thr Thr Ser Met Ala Asn Tyr Thr Ala Thr Thr Ser
                245                 250                 255

Ala Ser Gly Gly Ser Leu Val Glu Phe Thr Asn Asp Gly Gly Asn Arg
            260                 265                 270

Asp Val Gln Val Asp Tyr Leu Ser Val Asn Gly Ala Val Arg Gln Ala
        275                 280                 285

Glu Asp Gln Thr Tyr Asn Thr Gly Val Tyr Gln Asn Gly Gln Cys Gly
    290                 295                 300

Gly Gly Asn Gly Arg Ser Glu Trp Leu His Cys Asn Gly Ala Ile Gly
305                 310                 315                 320

Phe Gly Asn Leu

<210> SEQ ID NO 7
<211> LENGTH: 579
<212> TYPE: DNA
<213> ORGANISM: artificial sequence
<220> FEATURE:
<223> OTHER INFORMATION: xylanase region of PP7436
<220> FEATURE:
<221> NAME/KEY: CDS
<222> LOCATION: (1)..(579)
<220> FEATURE:
<221> NAME/KEY: misc_feature
<222> LOCATION: (1)..(579)

<400> SEQUENCE: 7 gag gct gaa gct gct ctg atg gct tcc act ttc tac tgg cat ctt tgg      48
Glu Ala Glu Ala Ala Leu Met Ala Ser Thr Phe Tyr Trp His Leu Trp
1               5                   10                  15 act gat gga atc ggt aca gtt aac gcc acc aac ggt tcc gat gga aac      96
Thr Asp Gly Ile Gly Thr Val Asn Ala Thr Asn Gly Ser Asp Gly Asn
            20                  25                  30 tac tcc gtt tct tgg agt aac tgt gga aac ttt gtc gta ggc aag gga     144
Tyr Ser Val Ser Trp Ser Asn Cys Gly Asn Phe Val Val Gly Lys Gly
        35                  40                  45 tgg acc act ggc agt gca acc aga gtc att aac tac aat gcc cat gcc     192
Trp Thr Thr Gly Ser Ala Thr Arg Val Ile Asn Tyr Asn Ala His Ala
    50                  55                  60 ttt tct gtg gtt ggt aat gct tat tta gct ctc tat gga tgg aca aga     240
Phe Ser Val Val Gly Asn Ala Tyr Leu Ala Leu Tyr Gly Trp Thr Arg
65                  70                  75                  80 aat tca cta atc gaa tac tat gtg gtt gat tct tgg ggt act tat aga     288
Asn Ser Leu Ile Glu Tyr Tyr Val Val Asp Ser Trp Gly Thr Tyr Arg
                85                  90                  95 cca act ggt act tac aaa ggt act gtt acc tcc gac ggt ggc act tac     336
Pro Thr Gly Thr Tyr Lys Gly Thr Val Thr Ser Asp Gly Gly Thr Tyr
            100                 105                 110 gac att tac aca aca aca cgt act aac gct cct agt atc gac gga aat     384
Asp Ile Tyr Thr Thr Thr Arg Thr Asn Ala Pro Ser Ile Asp Gly Asn
        115                 120                 125 aat aca acc ttt act cag ttc tgg tca gtt cga cag agt aag agg cca     432
Asn Thr Thr Phe Thr Gln Phe Trp Ser Val Arg Gln Ser Lys Arg Pro
    130                 135                 140 att ggt acc aac aat act att acc ttc tct aat cac gta aat gca tgg     480
Ile Gly Thr Asn Asn Thr Ile Thr Phe Ser Asn His Val Asn Ala Trp
145                 150                 155                 160 aaa tct aag ggt atg aac ttg gga tct tca tgg agt tac caa gtc ttg     528
```

```
Lys Ser Lys Gly Met Asn Leu Gly Ser Ser Trp Ser Tyr Gln Val Leu
            165                 170                 175 gct act gag ggt tat caa tca tct ggt tat tct aat gta aca gtg tgg      576
Ala Thr Glu Gly Tyr Gln Ser Ser Gly Tyr Ser Asn Val Thr Val Trp
            180                 185                 190 taa                                                                   579

<210> SEQ ID NO 8
<211> LENGTH: 192
<212> TYPE: PRT
<213> ORGANISM: artificial sequence
<220> FEATURE:
<223> OTHER INFORMATION: xylanase region of PP7436

<400> SEQUENCE: 8

Glu Ala Glu Ala Ala Leu Met Ala Ser Thr Phe Tyr Trp His Leu Trp
1               5                   10                  15

Thr Asp Gly Ile Gly Thr Val Asn Ala Thr Asn Gly Ser Asp Gly Asn
            20                  25                  30

Tyr Ser Val Ser Trp Ser Asn Cys Gly Asn Phe Val Val Gly Lys Gly
        35                  40                  45

Trp Thr Thr Gly Ser Ala Thr Arg Val Ile Asn Tyr Asn Ala His Ala
    50                  55                  60

Phe Ser Val Val Gly Asn Ala Tyr Leu Ala Leu Tyr Gly Trp Thr Arg
65                  70                  75                  80

Asn Ser Leu Ile Glu Tyr Tyr Val Val Asp Ser Trp Gly Thr Tyr Arg
                85                  90                  95

Pro Thr Gly Thr Tyr Lys Gly Thr Val Thr Ser Asp Gly Gly Thr Tyr
            100                 105                 110

Asp Ile Tyr Thr Thr Thr Arg Thr Asn Ala Pro Ser Ile Asp Gly Asn
        115                 120                 125

Asn Thr Thr Phe Thr Gln Phe Trp Ser Val Arg Gln Ser Lys Arg Pro
    130                 135                 140

Ile Gly Thr Asn Asn Thr Ile Thr Phe Ser Asn His Val Asn Ala Trp
145                 150                 155                 160

Lys Ser Lys Gly Met Asn Leu Gly Ser Ser Trp Ser Tyr Gln Val Leu
                165                 170                 175

Ala Thr Glu Gly Tyr Gln Ser Ser Gly Tyr Ser Asn Val Thr Val Trp
            180                 185                 190

<210> SEQ ID NO 9
<211> LENGTH: 598
<212> TYPE: DNA
<213> ORGANISM: artificial sequence
<220> FEATURE:
<223> OTHER INFORMATION: PP6002 cassette
<220> FEATURE:
<221> NAME/KEY: misc_feature
<222> LOCATION: (1)..(598)

<400> SEQUENCE: 9
tttccctctc gagaagaggg catctactga ctactggcag aactggactg acggtggtgg      60
taccgtgaac gctactaatg gtagtgatgg taattactca gtttcttggt caaactgtgg     120
aaacttcgtc gttggtaagg gatggacaac cggatctgct actagagtaa tcaactacaa     180
tgccggagct ttttctcctt ctggtaatgg ttacttggcc ttgtatggat ggacaagaaa     240
ctctttgatt gaatattacg ttgtggattc ctggggtact tatcgtccaa ctggaacata     300
taaaggtact gtaacttctg acggaggtac ctatgatatt tacacaacta caagaactaa     360
```

```
tgctccatct atcgacggaa ataacactac atttacccag ttttggtctg tcagacaatc    420
taaaagacct attggaacta ataataccat aactttcagt aatcatgtta acgcttggaa    480
gtcaaaaggt atgaacttgg ttcctcctg tcctaccaa gttttggcaa ctgagggtta     540
ccaatctagt ggttattcaa atgttactgt ctggtaatag gcggccgcaa aaggaaaa     598
```

<210> SEQ ID NO 10
<211> LENGTH: 628
<212> TYPE: DNA
<213> ORGANISM: artificial sequence
<220> FEATURE:
<223> OTHER INFORMATION: PP6016 exp. cassette
<220> FEATURE:
<221> NAME/KEY: misc_feature
<222> LOCATION: (1)..(628)

<400> SEQUENCE: 10

```
tttccctctc gagaagagag ctcagactat ctgttctaac cagactggta ctaataacgg    60
atatttttac tcattttgga aggacactgg ttctgcatgc atgacccttg gttccggagg   120
aaactattct gttaattgga acttgggttc tggtaatatg gtctgtggta agggatggtc   180
taccggatct tcatcaagaa gaatcggtta caacgcagga gtttgggccc caaacggtaa   240
cgcttacttg acattgtatg gttggactag gaaccctttg atagaatact acgtcgtaga   300
tagttgggga tcatggcgtc ctccaggtgg aacttcagct ggtaccgtaa attccgatgg   360
aggtacttat aatttataca gaactcaaag ggtgaacgct ccatctattg atggtaccag   420 aacttttac caatattggt ccgttagaac aagtaaacgt cctactggat ctaatcagac   480
aattacattc gcaaatcatg ttaatgcttg gagatccaaa ggttggaatc tgggttctca   540
cgtgtaccaa attatggcca ctgagggtta tcaatctagt ggaaattcta atttgacagt   600
ttgggctcaa tagtaagcgg ccgcaaaa                                      628
```

<210> SEQ ID NO 11
<211> LENGTH: 1009
<212> TYPE: DNA
<213> ORGANISM: artificial sequence
<220> FEATURE:
<223> OTHER INFORMATION: PP6407 exp. cassette
<220> FEATURE:
<221> NAME/KEY: misc_feature
<222> LOCATION: (1)..(1009)

<400> SEQUENCE: 11

```
tttccctctc gagaaaagag cacaaacttt gaacaacaac tccactggaa ctcacgacgg    60
tttttattac acattttgga agactctgg ttctgcttcc atgacccttc accctggtgg   120
aagatattca tcacagtgga catctaacac taacaattgg gttggtggta agggttggaa   180
ccctggaggt cctagagtag ttaactacag tggatattac ggtgttaata actcccaaaa   240
ctcctacctt gccttgtacg gttggactcg taatcctttg gtggaatact acgttattga   300
gagttacggt tcttacaatc cagcatcctg tgctggagga gttgattatg gttccttcca   360
atctgacggt gctacctata acgtaagaag gtgcttgaga caaaatgctc caagtatcga   420
aggtaataac tctacatttt accagtactt ttcagttcgt aatccaaaga agggtttcgg   480
taatatttct ggtactatta ccgtcgctaa tcatttaat tattgggcat ccagaggtct   540
gaacttagga aaccatgatt atatggtttt cgccactgaa ggttatcaat ctcaaggttc   600
tagtgatatt actgtgtcaa gtggtactgg aggtggtgga ggaggaggaa ataccggatc   660
```

-continued

```
taaaacaata gtcgtcagag ccagaggtac cgcaggtgga gagaatatat ccttgaaggt    720
aaataatgcc actatcgctt catggacctt gacaacttca atggctaact acacagctac    780
tacatctgct tctggtggat ctctggttga gttcactaac gatggaggta atagagatgt    840
tcaagtggac tatttatcag tcaatggtgc tgtcagacaa gcagaagatc agacttataa    900
tactggtgtg tatcagaacg gacagtgcgg aggtggaaac ggaaggtctg agtggttgca    960
ttgtaacggt gccattggat ttggtaattt gtaataggcg ccgcaaaa                 1009
```

<210> SEQ ID NO 12
<211> LENGTH: 619
<212> TYPE: DNA
<213> ORGANISM: artificial sequence
<220> FEATURE:
<223> OTHER INFORMATION: PP7436 exp. cassette
<220> FEATURE:
<221> NAME/KEY: misc_feature
<222> LOCATION: (1)..(619)

<400> SEQUENCE: 12

```
tttccctctc gagaaaagag aggctgaagc tgctctgatg gcttccactt tctactggca     60
tctttggact gatggaatcg gtacagttaa cgccaccaac ggttccgatg gaaactactc    120
cgtttcttgg agtaactgtg gaacttttgt cgtaggcaag ggatggacca ctggcagtgc    180
aaccagagtc attaactaca atgcccatgc cttttctgtg gttggtaatg cttatttagc    240
tctctatgga tggacaagaa attcactaat cgaatactat gtggttgatt cttggggtac    300
ttatagacca actggtactt acaaaggtac tgttacctcc gacggtggca cttacgacat    360
ttacacaaca acacgtacta acgctcctag tatcgacgga aataatacaa cctttactca    420
gttctggtca gttcgacaga gtaagaggcc aattggtacc aacaatacta ttaccttctc    480
taatcacgta aatgcatgga atctaaggg tatgaacttg ggatcttcat ggagttacca    540
agtcttggct actgagggtt atcaatcatc tggttattct aatgtaacag tgtggtaata    600
ggcggccgca aaggaaaa                                                  619
```

<210> SEQ ID NO 13
<211> LENGTH: 561
<212> TYPE: DNA
<213> ORGANISM: artificial nucleotide sequence
<220> FEATURE:
<223> OTHER INFORMATION: XYLA1A (BD6002)
<220> FEATURE:
<221> NAME/KEY: CDS
<222> LOCATION: (1)..(561)

<400> SEQUENCE: 13

```
atg gct tcg aca gac tac tgg caa aat tgg act gat ggt ggt ggg aca      48
Met Ala Ser Thr Asp Tyr Trp Gln Asn Trp Thr Asp Gly Gly Gly Thr
1               5                   10                  15 gta aat gct acc aat gga tct gat ggc aat tac agc gtt tca tgg tca      96
Val Asn Ala Thr Asn Gly Ser Asp Gly Asn Tyr Ser Val Ser Trp Ser
            20                  25                  30 aat tgc ggg aat ttt gtt gtt ggt aaa ggc tgg act acc gga tca gca     144
Asn Cys Gly Asn Phe Val Val Gly Lys Gly Trp Thr Thr Gly Ser Ala
        35                  40                  45 act agg gta ata aac tat aat gcc gga gcc ttt tcg ccg tcc ggt aat     192
Thr Arg Val Ile Asn Tyr Asn Ala Gly Ala Phe Ser Pro Ser Gly Asn
    50                  55                  60 gga tat ttg gct ctt tat ggg tgg acg aga aat tca ctc ata gaa tat     240
Gly Tyr Leu Ala Leu Tyr Gly Trp Thr Arg Asn Ser Leu Ile Glu Tyr
65                  70                  75                  80
```

```
tac gtc gtt gat agc tgg ggg act tat aga cct act gga act tat aaa          288
Tyr Val Val Asp Ser Trp Gly Thr Tyr Arg Pro Thr Gly Thr Tyr Lys
                85                  90                  95 ggc act gtg act agt gat gga ggg act tat gac ata tac acg act aca          336
Gly Thr Val Thr Ser Asp Gly Gly Thr Tyr Asp Ile Tyr Thr Thr Thr
            100                 105                 110 cga acc aac gca cct tcc att gac ggc aat aat aca act ttc acc cag          384
Arg Thr Asn Ala Pro Ser Ile Asp Gly Asn Asn Thr Thr Phe Thr Gln
        115                 120                 125 ttc tgg agt gtt agg cag tcg aag aga ccg att ggt acc aac aat acc          432
Phe Trp Ser Val Arg Gln Ser Lys Arg Pro Ile Gly Thr Asn Asn Thr
130                 135                 140 atc acc ttt agc aac cat gtt aac gcc tgg aag agt aaa gga atg aat          480
Ile Thr Phe Ser Asn His Val Asn Ala Trp Lys Ser Lys Gly Met Asn
145                 150                 155                 160 ttg ggg agt agt tgg tct tat cag gta tta gca aca gag ggc tat caa          528
Leu Gly Ser Ser Trp Ser Tyr Gln Val Leu Ala Thr Glu Gly Tyr Gln
                165                 170                 175 agt agt ggg tac tct aac gta acg gtc tgg taa                              561
Ser Ser Gly Tyr Ser Asn Val Thr Val Trp
                180                 185

<210> SEQ ID NO 14
<211> LENGTH: 186
<212> TYPE: PRT
<213> ORGANISM: artificial nucleotide sequence
<220> FEATURE:
<223> OTHER INFORMATION: XylA1A (BD6002)

<400> SEQUENCE: 14

Met Ala Ser Thr Asp Tyr Trp Gln Asn Trp Thr Asp Gly Gly Gly Thr
1               5                   10                  15

Val Asn Ala Thr Asn Gly Ser Asp Gly Asn Tyr Ser Val Ser Trp Ser
            20                  25                  30

Asn Cys Gly Asn Phe Val Val Gly Lys Gly Trp Thr Thr Gly Ser Ala
        35                  40                  45

Thr Arg Val Ile Asn Tyr Asn Ala Gly Ala Phe Ser Pro Ser Gly Asn
    50                  55                  60

Gly Tyr Leu Ala Leu Tyr Gly Trp Thr Arg Asn Ser Leu Ile Glu Tyr
65                  70                  75                  80

Tyr Val Val Asp Ser Trp Gly Thr Tyr Arg Pro Thr Gly Thr Tyr Lys
                85                  90                  95

Gly Thr Val Thr Ser Asp Gly Gly Thr Tyr Asp Ile Tyr Thr Thr Thr
            100                 105                 110

Arg Thr Asn Ala Pro Ser Ile Asp Gly Asn Asn Thr Thr Phe Thr Gln
        115                 120                 125

Phe Trp Ser Val Arg Gln Ser Lys Arg Pro Ile Gly Thr Asn Asn Thr
130                 135                 140

Ile Thr Phe Ser Asn His Val Asn Ala Trp Lys Ser Lys Gly Met Asn
145                 150                 155                 160

Leu Gly Ser Ser Trp Ser Tyr Gln Val Leu Ala Thr Glu Gly Tyr Gln
                165                 170                 175

Ser Ser Gly Tyr Ser Asn Val Thr Val Trp
            180                 185

<210> SEQ ID NO 15
<211> LENGTH: 561
<212> TYPE: DNA
```

<213> ORGANISM: Artificial Sequence
<220> FEATURE:
<223> OTHER INFORMATION: xylA1B (BD7436)
<220> FEATURE:
<221> NAME/KEY: CDS
<222> LOCATION: (1)..(561)

<400> SEQUENCE: 15

```
atg gct tcg aca ttc tac tgg cac ttg tgg act gat ggt ata ggg aca      48
Met Ala Ser Thr Phe Tyr Trp His Leu Trp Thr Asp Gly Ile Gly Thr
 1               5                  10                  15 gta aat gct acc aat gga tct gat ggc aat tac agc gtt tca tgg tca      96
Val Asn Ala Thr Asn Gly Ser Asp Gly Asn Tyr Ser Val Ser Trp Ser
             20                  25                  30 aat tgc ggg aat ttt gtt gtt ggt aaa ggc tgg act acc gga tca gca     144
Asn Cys Gly Asn Phe Val Val Gly Lys Gly Trp Thr Thr Gly Ser Ala
         35                  40                  45 act agg gta ata aac tat aat gcc cac gcc ttt tcg gta gtg ggt aat     192
Thr Arg Val Ile Asn Tyr Asn Ala His Ala Phe Ser Val Val Gly Asn
     50                  55                  60 gct tat ttg gct ctt tat ggg tgg acg aga aat tca ctc ata gaa tat     240
Ala Tyr Leu Ala Leu Tyr Gly Trp Thr Arg Asn Ser Leu Ile Glu Tyr
 65                  70                  75                  80 tac gtc gtt gat agc tgg ggg act tat aga cct act gga act tat aaa     288
Tyr Val Val Asp Ser Trp Gly Thr Tyr Arg Pro Thr Gly Thr Tyr Lys
                 85                  90                  95 ggc act gtg act agt gat gga ggg act tat gac ata tac acg act aca     336
Gly Thr Val Thr Ser Asp Gly Gly Thr Tyr Asp Ile Tyr Thr Thr Thr
            100                 105                 110 cga acc aac gca cct tcc att gac ggc aat aat aca act ttc acc cag     384
Arg Thr Asn Ala Pro Ser Ile Asp Gly Asn Asn Thr Thr Phe Thr Gln
        115                 120                 125 ttc tgg agt gtt agg cag tcg aag aga ccg att ggt acc aac aat acc     432
Phe Trp Ser Val Arg Gln Ser Lys Arg Pro Ile Gly Thr Asn Asn Thr
130                 135                 140 atc acc ttt agc aac cat gtt aac gcc tgg aag agt aaa gga atg aat     480
Ile Thr Phe Ser Asn His Val Asn Ala Trp Lys Ser Lys Gly Met Asn
145                 150                 155                 160 ttg ggg agt agt tgg tct tat cag gta tta gca aca gag ggc tat caa     528
Leu Gly Ser Ser Trp Ser Tyr Gln Val Leu Ala Thr Glu Gly Tyr Gln
                165                 170                 175 agt agt ggg tac tct aac gta acg gtc tgg taa                         561
Ser Ser Gly Tyr Ser Asn Val Thr Val Trp
            180                 185
```

<210> SEQ ID NO 16
<211> LENGTH: 186
<212> TYPE: PRT
<213> ORGANISM: Artificial Sequence
<220> FEATURE:
<223> OTHER INFORMATION: xylA1B (BD7436)

<400> SEQUENCE: 16

```
Met Ala Ser Thr Phe Tyr Trp His Leu Trp Thr Asp Gly Ile Gly Thr
 1               5                  10                  15

Val Asn Ala Thr Asn Gly Ser Asp Gly Asn Tyr Ser Val Ser Trp Ser
             20                  25                  30

Asn Cys Gly Asn Phe Val Val Gly Lys Gly Trp Thr Thr Gly Ser Ala
         35                  40                  45

Thr Arg Val Ile Asn Tyr Asn Ala His Ala Phe Ser Val Val Gly Asn
     50                  55                  60
```

```
Ala Tyr Leu Ala Leu Tyr Gly Trp Thr Arg Asn Ser Leu Ile Glu Tyr
 65                  70                  75                  80

Tyr Val Val Asp Ser Trp Gly Thr Tyr Arg Pro Thr Gly Thr Tyr Lys
                 85                  90                  95

Gly Thr Val Thr Ser Asp Gly Gly Thr Tyr Asp Ile Tyr Thr Thr Thr
            100                 105                 110

Arg Thr Asn Ala Pro Ser Ile Asp Gly Asn Asn Thr Thr Phe Thr Gln
        115                 120                 125

Phe Trp Ser Val Arg Gln Ser Lys Arg Pro Ile Gly Thr Asn Asn Thr
    130                 135                 140

Ile Thr Phe Ser Asn His Val Asn Ala Trp Lys Ser Lys Gly Met Asn
145                 150                 155                 160

Leu Gly Ser Ser Trp Ser Tyr Gln Val Leu Ala Thr Glu Gly Tyr Gln
                165                 170                 175

Ser Ser Gly Tyr Ser Asn Val Thr Val Trp
            180                 185

<210> SEQ ID NO 17
<211> LENGTH: 594
<212> TYPE: DNA
<213> ORGANISM: Artificial Sequence
<220> FEATURE:
<223> OTHER INFORMATION: xylA1C
<220> FEATURE:
<221> NAME/KEY: CDS
<222> LOCATION: (1)..(594)

<400> SEQUENCE: 17 atg gct caa acc atc tgc agc aac cag acc ggc acc aac aac ggc tac      48
Met Ala Gln Thr Ile Cys Ser Asn Gln Thr Gly Thr Asn Asn Gly Tyr
 1               5                  10                  15 ttc tac tcg ttc tgg aag gac acc ggg tcg gcg tgc atg aca ctg ggt      96
Phe Tyr Ser Phe Trp Lys Asp Thr Gly Ser Ala Cys Met Thr Leu Gly
             20                  25                  30 tcc ggc ggc aac tac agc gtc aac tgg aac ctg ggt tcc ggg aac atg     144
Ser Gly Gly Asn Tyr Ser Val Asn Trp Asn Leu Gly Ser Gly Asn Met
         35                  40                  45 gtc tgc ggc aaa ggc tgg agt acc gga tct tca agc cgc aga atc ggc     192
Val Cys Gly Lys Gly Trp Ser Thr Gly Ser Ser Ser Arg Arg Ile Gly
     50                  55                  60 tac aac gcc ggc gtc tgg gcg ccg aac ggc aat gcc tac ctg act ctg     240
Tyr Asn Ala Gly Val Trp Ala Pro Asn Gly Asn Ala Tyr Leu Thr Leu
 65                  70                  75                  80 tat ggg tgg acc agg aac ccg ctc atc gag tac tac gtg gtc gac agt     288
Tyr Gly Trp Thr Arg Asn Pro Leu Ile Glu Tyr Tyr Val Val Asp Ser
                 85                  90                  95 tgg gga agc tgg agg ccg cca ggc gga acc tcc gcg ggc acc gtc aat     336
Trp Gly Ser Trp Arg Pro Pro Gly Gly Thr Ser Ala Gly Thr Val Asn
            100                 105                 110 agc gat ggc ggg acc tac aac ctc tat cgg acg cag cgg gtc aac gcg     384
Ser Asp Gly Gly Thr Tyr Asn Leu Tyr Arg Thr Gln Arg Val Asn Ala
        115                 120                 125 cct tcc atc gac ggc acc cgg acg ttc tat cag tac tgg agt gtc cgg     432
Pro Ser Ile Asp Gly Thr Arg Thr Phe Tyr Gln Tyr Trp Ser Val Arg
    130                 135                 140 acc tcg aag agg ccc acc ggg agc aac cag acc atc acc ttc gcg aac     480
Thr Ser Lys Arg Pro Thr Gly Ser Asn Gln Thr Ile Thr Phe Ala Asn
145                 150                 155                 160 cac gtg aat gcg tgg agg agc aaa ggg tgg aat ctg ggg agt cac gtc     528
His Val Asn Ala Trp Arg Ser Lys Gly Trp Asn Leu Gly Ser His Val
```

```
                        165                 170                 175
tac cag ata atg gca aca gag gga tat caa agc agc ggg aat tcc aac      576
Tyr Gln Ile Met Ala Thr Glu Gly Tyr Gln Ser Ser Gly Asn Ser Asn
                    180                 185                 190 ctg acg gtg tgg gcg cag                                              594
Leu Thr Val Trp Ala Gln
        195

<210> SEQ ID NO 18
<211> LENGTH: 198
<212> TYPE: PRT
<213> ORGANISM: Artificial Sequence
<220> FEATURE:
<223> OTHER INFORMATION: xylA1C

<400> SEQUENCE: 18

Met Ala Gln Thr Ile Cys Ser Asn Gln Thr Gly Thr Asn Asn Gly Tyr
1               5                   10                  15

Phe Tyr Ser Phe Trp Lys Asp Thr Gly Ser Ala Cys Met Thr Leu Gly
                20                  25                  30

Ser Gly Gly Asn Tyr Ser Val Asn Trp Asn Leu Gly Ser Gly Asn Met
            35                  40                  45

Val Cys Gly Lys Gly Trp Ser Thr Gly Ser Ser Arg Arg Ile Gly
    50                  55                  60

Tyr Asn Ala Gly Val Trp Ala Pro Asn Gly Asn Ala Tyr Leu Thr Leu
65                  70                  75                  80

Tyr Gly Trp Thr Arg Asn Pro Leu Ile Glu Tyr Tyr Val Val Asp Ser
                85                  90                  95

Trp Gly Ser Trp Arg Pro Pro Gly Gly Thr Ser Ala Gly Thr Val Asn
            100                 105                 110

Ser Asp Gly Gly Thr Tyr Asn Leu Tyr Arg Thr Gln Arg Val Asn Ala
        115                 120                 125

Pro Ser Ile Asp Gly Thr Arg Thr Phe Tyr Gln Tyr Trp Ser Val Arg
    130                 135                 140

Thr Ser Lys Arg Pro Thr Gly Ser Asn Gln Thr Ile Thr Phe Ala Asn
145                 150                 155                 160

His Val Asn Ala Trp Arg Ser Lys Gly Trp Asn Leu Gly Ser His Val
                165                 170                 175

Tyr Gln Ile Met Ala Thr Glu Gly Tyr Gln Ser Ser Gly Asn Ser Asn
            180                 185                 190

Leu Thr Val Trp Ala Gln
        195

<210> SEQ ID NO 19
<211> LENGTH: 972
<212> TYPE: DNA
<213> ORGANISM: Artificial Sequence
<220> FEATURE:
<223> OTHER INFORMATION: XylA1D
<220> FEATURE:
<221> NAME/KEY: CDS
<222> LOCATION: (1)..(972)

<400> SEQUENCE: 19 atg cag acg ctc aac aac aat tcc acc ggc acg cac gac ggc ttc tac      48
Met Gln Thr Leu Asn Asn Asn Ser Thr Gly Thr His Asp Gly Phe Tyr
1               5                   10                  15 tac acg ttc tgg aag gac tcg ggc agc gcc tcg atg acc ctc cat ccg      96
Tyr Thr Phe Trp Lys Asp Ser Gly Ser Ala Ser Met Thr Leu His Pro
                20                  25                  30
```

```
ggc gga cgc tac agc tcc cag tgg acc agc aac acc aac aac tgg gtc      144
Gly Gly Arg Tyr Ser Ser Gln Trp Thr Ser Asn Thr Asn Asn Trp Val
         35                  40                  45 ggc ggg aaa ggc tgg aat ccc ggt ggc ccg cgc gtg gtc aac tac tcg      192
Gly Gly Lys Gly Trp Asn Pro Gly Gly Pro Arg Val Val Asn Tyr Ser
 50                  55                  60 ggc tac tac ggg gtc aac aac agc cag aac tcc tac ctg gcg ctg tac      240
Gly Tyr Tyr Gly Val Asn Asn Ser Gln Asn Ser Tyr Leu Ala Leu Tyr
 65                  70                  75                  80 ggc tgg acc cgc aat ccg ctg gtc gag tac tac gtg atc gag agc tac      288
Gly Trp Thr Arg Asn Pro Leu Val Glu Tyr Tyr Val Ile Glu Ser Tyr
                 85                  90                  95 ggc tcc tac aac ccg gcc agt tgc gcc ggc ggg gtg gac tac ggc agc      336
Gly Ser Tyr Asn Pro Ala Ser Cys Ala Gly Gly Val Asp Tyr Gly Ser
            100                 105                 110 ttc cag agc gat ggc gcc acc tac aac gta cgc cgc tgc ctg cgc cag      384
Phe Gln Ser Asp Gly Ala Thr Tyr Asn Val Arg Arg Cys Leu Arg Gln
            115                 120                 125 aac gcg ccg tcg atc gaa ggc aac aac agc acc ttc tac cag tac ttc      432
Asn Ala Pro Ser Ile Glu Gly Asn Asn Ser Thr Phe Tyr Gln Tyr Phe
130                 135                 140 agc gtg cgc aat ccc aag aag gga ttc ggc aac atc tcc ggc acg atc      480
Ser Val Arg Asn Pro Lys Lys Gly Phe Gly Asn Ile Ser Gly Thr Ile
145                 150                 155                 160 acc gtc gcc aac cac ttc aac tac tgg gcc agc cgc ggc ctc aac ctc      528
Thr Val Ala Asn His Phe Asn Tyr Trp Ala Ser Arg Gly Leu Asn Leu
                165                 170                 175 ggc aac cac gac tac atg gtg ttc gcc acc gag ggc tac cag agc cag      576
Gly Asn His Asp Tyr Met Val Phe Ala Thr Glu Gly Tyr Gln Ser Gln
            180                 185                 190 ggc agc agc gac atc acc gtg agt tcg ggt acc ggc ggc ggt ggc          624
Gly Ser Ser Asp Ile Thr Val Ser Ser Gly Thr Gly Gly Gly Gly
            195                 200                 205 ggc ggc aac acg ggc agc aag acc atc gtg gtg cgc gcg cgc ggc acc      672
Gly Gly Asn Thr Gly Ser Lys Thr Ile Val Val Arg Ala Arg Gly Thr
210                 215                 220 gcc ggc gga gag aac atc tcg ctc aag gtc aac aac gcc acc atc gcc      720
Ala Gly Gly Glu Asn Ile Ser Leu Lys Val Asn Asn Ala Thr Ile Ala
225                 230                 235                 240 agc tgg acg ctc acc acc agc atg gcc aac tac acg gcc acc acc tcg      768
Ser Trp Thr Leu Thr Thr Ser Met Ala Asn Tyr Thr Ala Thr Thr Ser
                245                 250                 255 gca tcg ggc ggc tcg ctg gtg gag ttc acc aac gac ggc ggc aac cgc      816
Ala Ser Gly Gly Ser Leu Val Glu Phe Thr Asn Asp Gly Gly Asn Arg
            260                 265                 270 gac gtg cag gtg gac tac ctc agc gtc aat ggc gcc gtc cgc cag gcc      864
Asp Val Gln Val Asp Tyr Leu Ser Val Asn Gly Ala Val Arg Gln Ala
            275                 280                 285 gag gac cag acc tac aac acc ggc gtg tac cag aac ggc cag tgc ggc      912
Glu Asp Gln Thr Tyr Asn Thr Gly Val Tyr Gln Asn Gly Gln Cys Gly
            290                 295                 300 ggc ggc aac ggc cgc agc gaa tgg ctg cac tgc aac ggt gcc atc ggc      960
Gly Gly Asn Gly Arg Ser Glu Trp Leu His Cys Asn Gly Ala Ile Gly
305                 310                 315                 320 ttc gga aat ctc                                                      972
Phe Gly Asn Leu

<210> SEQ ID NO 20
<211> LENGTH: 324
```

<212> TYPE: PRT
<213> ORGANISM: Artificial Sequence
<220> FEATURE:
<223> OTHER INFORMATION: XylA1D

<400> SEQUENCE: 20

Met Gln Thr Leu Asn Asn Ser Thr Gly Thr His Asp Gly Phe Tyr
1               5                   10                  15

Tyr Thr Phe Trp Lys Asp Ser Gly Ser Ala Ser Met Thr Leu His Pro
            20                  25                  30

Gly Gly Arg Tyr Ser Ser Gln Trp Thr Ser Asn Thr Asn Asn Trp Val
        35                  40                  45

Gly Gly Lys Gly Trp Asn Pro Gly Gly Pro Arg Val Val Asn Tyr Ser
    50                  55                  60

Gly Tyr Tyr Gly Val Asn Asn Ser Gln Asn Ser Tyr Leu Ala Leu Tyr
65                  70                  75                  80

Gly Trp Thr Arg Asn Pro Leu Val Glu Tyr Tyr Val Ile Glu Ser Tyr
                85                  90                  95

Gly Ser Tyr Asn Pro Ala Ser Cys Ala Gly Gly Val Asp Tyr Gly Ser
            100                 105                 110

Phe Gln Ser Asp Gly Ala Thr Tyr Asn Val Arg Arg Cys Leu Arg Gln
        115                 120                 125

Asn Ala Pro Ser Ile Glu Gly Asn Asn Ser Thr Phe Tyr Gln Tyr Phe
    130                 135                 140

Ser Val Arg Asn Pro Lys Lys Gly Phe Gly Asn Ile Ser Gly Thr Ile
145                 150                 155                 160

Thr Val Ala Asn His Phe Asn Tyr Trp Ala Ser Arg Gly Leu Asn Leu
                165                 170                 175

Gly Asn His Asp Tyr Met Val Phe Ala Thr Glu Gly Tyr Gln Ser Gln
            180                 185                 190

Gly Ser Ser Asp Ile Thr Val Ser Ser Gly Thr Gly Gly Gly Gly Gly
        195                 200                 205

Gly Gly Asn Thr Gly Ser Lys Thr Ile Val Val Arg Ala Arg Gly Thr
    210                 215                 220

Ala Gly Gly Glu Asn Ile Ser Leu Lys Val Asn Asn Ala Thr Ile Ala
225                 230                 235                 240

Ser Trp Thr Leu Thr Thr Ser Met Ala Asn Tyr Thr Ala Thr Thr Ser
                245                 250                 255

Ala Ser Gly Gly Ser Leu Val Glu Phe Thr Asn Asp Gly Gly Asn Arg
            260                 265                 270

Asp Val Gln Val Asp Tyr Leu Ser Val Asn Gly Ala Val Arg Gln Ala
        275                 280                 285

Glu Asp Gln Thr Tyr Asn Thr Gly Val Tyr Gln Asn Gly Gln Cys Gly
    290                 295                 300

Gly Gly Asn Gly Arg Ser Glu Trp Leu His Cys Asn Gly Ala Ile Gly
305                 310                 315                 320

Phe Gly Asn Leu

<210> SEQ ID NO 21
<211> LENGTH: 978
<212> TYPE: DNA
<213> ORGANISM: Artificial Sequence
<220> FEATURE:
<223> OTHER INFORMATION: XylA1E
<220> FEATURE:
<221> NAME/KEY: CDS
<222> LOCATION: (1)..(978)

<400> SEQUENCE: 21

```
atg gct caa acc tgc atc acg tcg agc cag acg ggc acc aac aac ggc     48
Met Ala Gln Thr Cys Ile Thr Ser Ser Gln Thr Gly Thr Asn Asn Gly
1               5                   10                  15 aat tac ttt tcg ttc tgg aaa gac agt ccg ggc acg gtg aac ttc tgc     96
Asn Tyr Phe Ser Phe Trp Lys Asp Ser Pro Gly Thr Val Asn Phe Cys
            20                  25                  30 atg tat gcg aat ggc cgc tat acc tcc aac tgg agc ggc atc aac aac    144
Met Tyr Ala Asn Gly Arg Tyr Thr Ser Asn Trp Ser Gly Ile Asn Asn
        35                  40                  45 tgg gtg ggc ggc aag ggc tgg gct acc ggc tcc agc cac acg atc agc    192
Trp Val Gly Gly Lys Gly Trp Ala Thr Gly Ser Ser His Thr Ile Ser
    50                  55                  60 tac tcc ggc acg ttc aat tcg ccg ggc aac ggt tac ctg gcc ctg tat    240
Tyr Ser Gly Thr Phe Asn Ser Pro Gly Asn Gly Tyr Leu Ala Leu Tyr
65                  70                  75                  80 ggc tgg acc acc aat cca ttg gtc gag tac tac atc gtc gac agc tgg    288
Gly Trp Thr Thr Asn Pro Leu Val Glu Tyr Tyr Ile Val Asp Ser Trp
                85                  90                  95 ggt acc tac cgt ccg ccg ggc ggc cag ggt ttc atg ggc acg gta gtt    336
Gly Thr Tyr Arg Pro Pro Gly Gly Gln Gly Phe Met Gly Thr Val Val
            100                 105                 110 agc gac ggg ggc acg tac gac gtg tac cgg acg caa cgc gtg aac cag    384
Ser Asp Gly Gly Thr Tyr Asp Val Tyr Arg Thr Gln Arg Val Asn Gln
        115                 120                 125 cca tcc atc atc ggc aac gcc acg ttc tac cag tac tgg agc gtg cgg    432
Pro Ser Ile Ile Gly Asn Ala Thr Phe Tyr Gln Tyr Trp Ser Val Arg
    130                 135                 140 cag tcg aag cgc gtg ggc ggc acc atc acc atc gcc aac cat ttc aac    480
Gln Ser Lys Arg Val Gly Gly Thr Ile Thr Ile Ala Asn His Phe Asn
145                 150                 155                 160 gcc tgg gcc acg ctg ggc atg aac ctg ggc cag cac aac tac cag gtc    528
Ala Trp Ala Thr Leu Gly Met Asn Leu Gly Gln His Asn Tyr Gln Val
                165                 170                 175 atg gcc acc gag ggt tac cag agc agc ggc agc tcc gac atc acc gtg    576
Met Ala Thr Glu Gly Tyr Gln Ser Ser Gly Ser Ser Asp Ile Thr Val
            180                 185                 190 acc gaa ggt ggc ggc agc tcc tcg tcg tcc tcg ggc ggc ggc agc acc    624
Thr Glu Gly Gly Gly Ser Ser Ser Ser Ser Gly Gly Gly Ser Thr
        195                 200                 205 agc agc agt ggt ggc ggc ggc aac aag agc ttc acg gtg cgt gcg cgc    672
Ser Ser Ser Gly Gly Gly Gly Asn Lys Ser Phe Thr Val Arg Ala Arg
    210                 215                 220 ggc acg gcc gga ggc gag aac atc cag ctg cag gtg aac aac cag acg    720
Gly Thr Ala Gly Gly Glu Asn Ile Gln Leu Gln Val Asn Asn Gln Thr
225                 230                 235                 240 gtc gcg agc tgg aac ctc acc acc agc atg cag aac tac acc gcc tcg    768
Val Ala Ser Trp Asn Leu Thr Thr Ser Met Gln Asn Tyr Thr Ala Ser
                245                 250                 255 acc agc ctg agc ggc ggc atc acc gtg ctc tac acc aac gac ggc ggc    816
Thr Ser Leu Ser Gly Gly Ile Thr Val Leu Tyr Thr Asn Asp Gly Gly
            260                 265                 270 agc cgc gac gtg cag gtg gac tac atc atc gtg aac ggc cag acc cgc    864
Ser Arg Asp Val Gln Val Asp Tyr Ile Ile Val Asn Gly Gln Thr Arg
        275                 280                 285 cag tcc gaa gcg cag agc tac aac acc ggg ttg tat gcg aat gga cgc    912
Gln Ser Glu Ala Gln Ser Tyr Asn Thr Gly Leu Tyr Ala Asn Gly Arg
    290                 295                 300
```

```
tgc ggc ggt ggc tcg aac agc gag tgg atg cat tgc aac ggc gcg atc       960
Cys Gly Gly Gly Ser Asn Ser Glu Trp Met His Cys Asn Gly Ala Ile
305                 310                 315                 320 ggc tac ggc aat acg ccc                                                978
Gly Tyr Gly Asn Thr Pro
            325
```

<210> SEQ ID NO 22
<211> LENGTH: 326
<212> TYPE: PRT
<213> ORGANISM: Artificial Sequence
<220> FEATURE:
<223> OTHER INFORMATION: XylA1E

<400> SEQUENCE: 22

```
Met Ala Gln Thr Cys Ile Thr Ser Ser Gln Thr Gly Thr Asn Asn Gly
1               5                   10                  15

Asn Tyr Phe Ser Phe Trp Lys Asp Ser Pro Gly Thr Val Asn Phe Cys
            20                  25                  30

Met Tyr Ala Asn Gly Arg Tyr Thr Ser Asn Trp Ser Gly Ile Asn Asn
        35                  40                  45

Trp Val Gly Gly Lys Gly Trp Ala Thr Gly Ser Ser His Thr Ile Ser
50                  55                  60

Tyr Ser Gly Thr Phe Asn Ser Pro Gly Asn Gly Tyr Leu Ala Leu Tyr
65                  70                  75                  80

Gly Trp Thr Thr Asn Pro Leu Val Glu Tyr Tyr Ile Val Asp Ser Trp
                85                  90                  95

Gly Thr Tyr Arg Pro Pro Gly Gly Gln Gly Phe Met Gly Thr Val Val
            100                 105                 110

Ser Asp Gly Gly Thr Tyr Asp Val Tyr Arg Thr Gln Arg Val Asn Gln
        115                 120                 125

Pro Ser Ile Ile Gly Asn Ala Thr Phe Tyr Gln Tyr Trp Ser Val Arg
130                 135                 140

Gln Ser Lys Arg Val Gly Gly Thr Ile Thr Ile Ala Asn His Phe Asn
145                 150                 155                 160

Ala Trp Ala Thr Leu Gly Met Asn Leu Gly Gln His Asn Tyr Gln Val
                165                 170                 175

Met Ala Thr Glu Gly Tyr Gln Ser Ser Gly Ser Ser Asp Ile Thr Val
            180                 185                 190

Thr Glu Gly Gly Gly Ser Ser Ser Ser Gly Gly Gly Ser Thr
        195                 200                 205

Ser Ser Ser Gly Gly Gly Asn Lys Ser Phe Thr Val Arg Ala Arg
210                 215                 220

Gly Thr Ala Gly Gly Glu Asn Ile Gln Leu Gln Val Asn Asn Gln Thr
225                 230                 235                 240

Val Ala Ser Trp Asn Leu Thr Thr Ser Met Gln Asn Tyr Thr Ala Ser
                245                 250                 255

Thr Ser Leu Ser Gly Ile Thr Val Leu Tyr Thr Asn Asp Gly Gly
            260                 265                 270

Ser Arg Asp Val Gln Val Asp Tyr Ile Ile Val Asn Gly Gln Thr Arg
        275                 280                 285

Gln Ser Glu Ala Gln Ser Tyr Asn Thr Gly Leu Tyr Ala Asn Gly Arg
    290                 295                 300

Cys Gly Gly Gly Ser Asn Ser Glu Trp Met His Cys Asn Gly Ala Ile
305                 310                 315                 320

Gly Tyr Gly Asn Thr Pro
```

```
                        325

<210> SEQ ID NO 23
<211> LENGTH: 36
<212> TYPE: DNA
<213> ORGANISM: Artificial Sequence
<220> FEATURE:
<223> OTHER INFORMATION: primer 1
<220> FEATURE:
<221> NAME/KEY: misc_feature
<222> LOCATION: (1)..(36)

<400> SEQUENCE: 23
agatctaaca tccaaagacg aaaggttgaa tgaaac                          36

<210> SEQ ID NO 24
<211> LENGTH: 36
<212> TYPE: DNA
<213> ORGANISM: Artificial Sequence
<220> FEATURE:
<223> OTHER INFORMATION: primer 2
<220> FEATURE:
<221> NAME/KEY: misc_feature
<222> LOCATION: (1)..(36)

<400> SEQUENCE: 24
cattaggatc cgcacaaacg aacgtctcac ttaatc                          36

<210> SEQ ID NO 25
<211> LENGTH: 37
<212> TYPE: DNA
<213> ORGANISM: Artificial Sequence
<220> FEATURE:
<223> OTHER INFORMATION: primer3
<220> FEATURE:
<221> NAME/KEY: misc_feature
<222> LOCATION: (1)..(37)

<400> SEQUENCE: 25
ggggccggga attccgatga gatttccttc aattttt                         37

<210> SEQ ID NO 26
<211> LENGTH: 45
<212> TYPE: DNA
<213> ORGANISM: Artificial Sequence
<220> FEATURE:
<223> OTHER INFORMATION: primer 4
<220> FEATURE:
<221> NAME/KEY: misc_feature
<222> LOCATION: (1)..(45)

<400> SEQUENCE: 26
gccggggaat tccgcggccg cctattacca gacagtaaca tttga                45

<210> SEQ ID NO 27
<211> LENGTH: 21
<212> TYPE: DNA
<213> ORGANISM: Artificial Sequence
<220> FEATURE:
<223> OTHER INFORMATION: primer 5
<220> FEATURE:
<221> NAME/KEY: misc_feature
<222> LOCATION: (1)..(21)

<400> SEQUENCE: 27
gcatctactg actactggca g                                          21

<210> SEQ ID NO 28
```

```
<211> LENGTH: 24
<212> TYPE: DNA
<213> ORGANISM: Artificial Sequence
<220> FEATURE:
<223> OTHER INFORMATION: primer 6
<220> FEATURE:
<221> NAME/KEY: misc_feature
<222> LOCATION: (1)..(24)

<400> SEQUENCE: 28
ccagacagta acatttgaat aacc                                         24

<210> SEQ ID NO 29
<211> LENGTH: 28
<212> TYPE: DNA
<213> ORGANISM: Artificial Sequence
<220> FEATURE:
<223> OTHER INFORMATION: primer 7
<220> FEATURE:
<221> NAME/KEY: misc_feature
<222> LOCATION: (1)..(28)

<400> SEQUENCE: 29
gggcgacacg gaaatgttga atactcat                                     28

<210> SEQ ID NO 30
<211> LENGTH: 27
<212> TYPE: DNA
<213> ORGANISM: Artificial Sequence
<220> FEATURE:
<223> OTHER INFORMATION: primer 8
<220> FEATURE:
<221> NAME/KEY: misc_feature
<222> LOCATION: (1)..(27)

<400> SEQUENCE: 30
ttaccaatgc ttaatcagtg aggcacc                                      27

<210> SEQ ID NO 31
<211> LENGTH: 25
<212> TYPE: DNA
<213> ORGANISM: Artificial Sequence
<220> FEATURE:
<223> OTHER INFORMATION: primer 9
<220> FEATURE:
<221> NAME/KEY: misc_feature
<222> LOCATION: (1)..(25)

<400> SEQUENCE: 31
gctgcctcgc gcgtttcggt gatga                                        25

<210> SEQ ID NO 32
<211> LENGTH: 25
<212> TYPE: DNA
<213> ORGANISM: Artificial Sequence
<220> FEATURE:
<223> OTHER INFORMATION: primer 10
<220> FEATURE:
<221> NAME/KEY: misc_feature
<222> LOCATION: (1)..(25)

<400> SEQUENCE: 32
gggaacactg aaaaataaca gttat                                        25

<210> SEQ ID NO 33
<211> LENGTH: 8546
<212> TYPE: DNA
<213> ORGANISM: Artificial Sequence
<220> FEATURE:
```

<223> OTHER INFORMATION: plasmid pBCS12771
<220> FEATURE:
<221> NAME/KEY: misc_feature
<222> LOCATION: (1)..(8546)

<400> SEQUENCE: 33

```
aaacgctgtc ttggaaccta atatgacaaa agcgtgatct catccaagat gaactaagtt      60
tggttcgttg aaatgctaac ggccagttgg tcaaaaagaa acttccaaaa gtcgccatac     120
cgtttgtctt gtttggtatt gattgacgaa tgctcaaaaa taatctcatt aatgcttagc     180
gcagtctctc tatcgcttct gaaccccggt gcacctgtgc cgaaacgcaa atggggaaac     240
acccgctttt tggatgatta tgcattgtct ccacattgta tgcttccaag attctggtgg     300
gaatactgct gatagcctaa cgttcatgat caaaatttaa ctgttctaac ccctacttga     360
cagcaatata taaacagaag gaagctgccc tgtcttaaac ctttttttt atcatcatta      420
ttagcttact ttcataattg cgactggttc caattgacaa gcttttgatt ttaacgactt     480
ttaacgacaa cttgagaaga tcaaaaaaca actaattatt cgaaggatcc aaacgatgag     540
atttccttca attttactg cagttttatt cgcagcatcc tccgcattag ctgctccagt      600
caacactaca acagaagatg aaacggcaca aattccggct gaagctgtca tcggttactc     660
agatttagaa ggggatttcg atgttgctgt tttgccattt tccaacagca caataacgg      720
gttattgttt ataaatacta ctattgccag cattgctgct aaagaagaag gggtatctct     780
cgagaagagg gcatctactg actactggca gaactggact gacggtggtg gtaccgtgaa     840
cgctactaat ggtagtgatg gtaattactc agtttcttgg tcaaactgtg gaaacttcgt     900
cgttggtaag ggatggacaa ccggatctgc tactagagta atcaactaca atgccggagc     960
tttttctcct tctggtaatg gttacttggc cttgtatgga tggacaagaa actctttgat    1020
tgaatattac gttgtggatt cctggggtac ttatcgtcca actggaacat ataaaggtac    1080
tgtaacttct gacggaggta cctatgatat ttacacaact acaagaacta atgctccatc    1140
tatcgacgga aataacacta catttaccca gttttggtct gtcagacaat ctaaaagacc    1200
tattggaact aataatacca taactttcag taatcatgtt aacgcttgga agtcaaaagg    1260
tatgaacttg ggttcctcct ggtcctacca agttttggca actgagggtt accaatctag    1320
tggttattca aatgttactg tctggtaata ggcggccgcg aattaattcg ccttagacat    1380
gactgttcct cagttcaagt tgggcactta cgagaagacc ggtcttgcta gattctaatc    1440
aagaggatgt cagaatgcca tttgcctgag agatgcaggc ttcattttg atacttttt     1500
atttgtaacc tatatagtat aggattttt ttgtcatttt gtttcttctc gtacgagctt      1560
gctcctgatc agcctatctc gcagctgatg aatatcttgt ggtagggtt tgggaaaatc     1620
attcgagttt gatgttttc ttggtatttc ccactcctct tcagagtaca gaagattaag     1680
tgagaagttc gttgtgcaa gcttatcgat aagctttaat gcggtagttt atcacagtta    1740
aattgctaac gcagtcaggc accgtgtatg aaatctaaca atgcgctcat cgtcatcctc    1800
ggcaccgtca ccctggatgc tgtaggcata ggcttggtta tgccggtact gccgggcctc    1860
ttgcgggata tcgtccattc cgacagcatc gccagtcact atggcgtgct gctagcgcta    1920
tatgcgttga tgcaatttct atgcgcaccc gttctcggag cactgtccga ccgctttggc    1980
cgccgcccag tcctgctcgc ttcgctactt ggagccacta tcgactacgc gatcatggcg    2040
accacacccg tcctgtggat ctatcgaatc taaatgtaag ttaaaatctc taaataatta    2100
aataagtccc agtttctcca tacgaacctt aacagcattg cggtgagcat ctagaccttc    2160
```

```
aacagcagcc agatccatca ctgcttggcc aatatgtttc agtccctcag gagttacgtc    2220
ttgtgaagtg atgaacttct ggaaggttgc agtgttaact ccgctgtatt gacgggcata    2280
tccgtacgtt ggcaaagtgt ggttggtacc ggaggagtaa tctccacaac tctctggaga    2340
gtaggcacca acaaacacag atccagcgtg ttgtacttga tcaacataag aagaagcatt    2400
ctcgatttgc aggatcaagt gttcaggagc gtactgattg acatttccaa agcctgctc     2460 gtaggttgca accgataggg ttgtagagtg tgcaatacac ttgcgtacaa tttcaaccct    2520
tggcaactgc acagcttggt tgtgaacagc atcttcaatt ctggcaagct ccttgtctgt    2580
catatcgaca gccaacagaa tcacctggga atcaatacca tgttcagctt gagacagaag    2640
gtctgaggca acgaaatctg gatcagcgta tttatcagca ataactagaa cttcagaagg    2700
cccagcaggc atgtcaatac tacacagggc tgatgtgtca ttttgaacca tcatcttggc    2760
agcagtaacg aactggtttc ctggaccaaa tattttgtca cacttaggaa cagtttctgt    2820
tccgtaagcc atagcagcta ctgcctgggc gcctcctgct agcacgatac acttagcacc    2880
aaccttgtgg gcaacgtaga tgacttctgg ggtaagggta ccatccttct taggtggaga    2940
tgcaaaaaca atttctttgc aaccagcaac tttggcagga acacccagca tcagggaagt    3000
ggaaggcaga attgcggttc caccaggaat atagaggcca actttctcaa taggtcttgc    3060
aaaacgagag cagactacac cagggcaagt ctcaacttgc aacgtctccg ttagttgagc    3120
ttcatggaat ttcctgacgt tatctataga gagatcaatg gctctcttaa cgttatctgg    3180
caattgcata agttcctctg ggaaaggagc ttctaacaca ggtgtcttca aagcgactcc    3240
atcaaacttg gcagttagtt ctaaaagggc tttgtcacca ttttgacgaa cattgtcgac    3300
aattggtttg actaattcca taatctgttc cgttttctgg ataggacgac gaagggcatc    3360
ttcaatttct tgtgaggagg ccttagaaac gtcaattttg cacaattcaa tacgaccttc    3420
agaagggact tctttaggtt tggattcttc tttaggttgt tccttggtgt atcctggctt    3480
ggcatctcct ttccttctag tgacctttag ggacttcata tccaggtttc tctccacctc    3540
gtccaacgtc acaccgtact tggcacatct aactaatgca aaataaaata agtcagcaca    3600
ttcccaggct atatcttcct tggatttagc ttctgcaagt tcatcagctt cctccctaat    3660
tttagcgttc aacaaaactt cgtcgtcaaa taaccgtttg gtataagaac cttctggagc    3720
attgctctta cgatcccaca aggtggcttc catggctcta agacccttttg attggccaaa    3780 acaggaagtg cgttccaagt gacagaaacc aacacctgtt tgttcaacca caaatttcaa    3840
gcagtctcca tcacaatcca attcgatacc cagcaacttt tgagttgctc cagatgtagc    3900
acctttatac cacaaaccgt gacgacgaga ttggtagact ccagtttgtg tccttatagc    3960
ctccggaata gacttttttgg acgagtacac caggcccaac gagtaattag aagagtcagc    4020
caccaaagta gtgaatagac catcggggcg gtcagtagtc aaagacgcca acaaaatttc    4080
actgacaggg aacttttttga catcttcaga agttcgtat tcagtagtca attgccgagc    4140
atcaataatg gggattatac cagaagcaac agtggaagtc acatctacca actttgcggt    4200
ctcagaaaaa gcataaacag ttctactacc gccattagtg aaacttttca aatcgcccag    4260
tggagaagaa aaaggcacag cgatactagc attagcgggc aaggatgcaa ctttatcaac    4320
cagggtccta tagataaccc tagcgcctgg gatcatcctt tggacaactc tttctgccaa    4380
atctaggtcc aaaatcactt cattgatacc attattgtac aacttgagca agttgtcgat    4440
cagctcctca aattggtcct ctgtaacgga tgactcaact tgcacattaa cttgaagctc    4500
agtcgattga gtgaacttga tcaggttgtg cagctggtca gcagcatagg gaaacacggc    4560
```

```
ttttcctacc aaactcaagg aattatcaaa ctctgcaaca cttgcgtatg caggtagcaa    4620
gggaaatgtc atacttgaag tcggacagtg agtgtagtct tgagaaattc tgaagccgta    4680
tttttattat cagtgagtca gtcatcagga gatcctctac gccggacgca tcgtggccgg    4740
catcaccggc gccacaggtg cggttgctgg cgcctatatc gccgacatca ccgatgggga    4800
agatcgggct cgcccacttcg ggctcatgag cgcttgtttc ggcgtgggta tggtggcagg    4860
ccccgtggcc gggggactgt tgggcgccat ctccttgcat gcaccattcc ttgcggcggc    4920
ggtgctcaac ggcctcaacc tactactggg ctgcttccta atgcaggagt cgcataaggg    4980
agagcgtcga gtatctatga ttggaagtat gggaatggtg atacccgcat tcttcagtgt    5040
cttgaggtct cctatcagat tatgcccaac taaagcaacc ggaggaggag atttcatggt    5100
aaatttctct gacttttggt catcagtaga ctcgaactgt gagactatct cggttatgac    5160
agcagaaatg tccttcttgg agacagtaaa tgaagtccca ccaataaaga aatccttgtt    5220
atcaggaaca aacttcttgt ttcgaacttt ttcggtgcct tgaactataa aatgtagagt    5280
ggatatgtcg ggtaggaatg gagcgggcaa atgcttacct tctggaccct caagaggtat    5340
gtagggtttg tagatactga tgccaacttc agtgacaacg ttgctatttc gttcaaacca    5400
ttccgaatcc agagaaatca aagttgtttg tctactattg atccaagcca gtgcggtctt    5460
gaaactgaca atagtgtgct cgtgttttga ggtcatcttt gtatgaataa atctagtctt    5520
tgatctaaat aatcttgacg agccagacga taataccaat ctaaactctt taaacgttaa    5580
aggacaagta tgtctgcctg tattaaaccc caaatcagct cgtagtctga tcctcatcaa    5640
cttgaggggc actatcttgt tttagagaaa tttgcggaga tgcgatatcg agaaaaaggt    5700
acgctgattt taaacgtgaa atttatctca agatctctgc ctcgcgcgtt tcggtgatga    5760
cggtgaaaac ctctgacaca tgcagctccc ggagacggtc acagcttgtc tgtaagcgga    5820
tgccgggagc agacaagccc gtcagggcgc gtcagcgggt gttggcgggt gtcggggcgc    5880
agccatgacc cagtcacgta gcgatagcgg agtgtatact ggcttaacta tgcggcatca    5940
gagcagattg tactgagagt gcaccatatg cggtgtgaaa taccgcacag atgcgtaagg    6000
agaaaatacc gcatcaggcg ctcttccgct tcctcgctca ctgactcgct gcgctcggtc    6060
gttcggctgc ggcgagcggt atcagctcac tcaaaggcgg taatacggtt atccacagaa    6120 tcagggata acgcaggaaa gaacatgtga gcaaaaggcc agcaaaggc caggaaccgt    6180 aaaaaggccg cgttgctggc gtttttccat aggctccgcc cccctgacga gcatcacaaa    6240
aatcgacgct caagtcagag gtggcgaaac ccgacaggac tataaagata ccaggcgttt    6300
ccccctggaa gctccctcgt gcgctctcct gttccgaccc tgccgcttac cggatacctg    6360
tccgcctttc tcccttcggg aagcgtggcg ctttctcaat gctcacgctg taggtatctc    6420
agttcggtgt aggtcgttcg ctccaagctg ggctgtgtgc acgaaccccc cgttcagccc    6480
gaccgctgcg ccttatccgg taactatcgt cttgagtcca acccggtaag acacgactta    6540
tcgccactgg cagcagccac tggtaacagg attagcagag cgaggtatgt aggcggtgct    6600
acagagttct tgaagtggtg gcctaactac ggctacacta aaggacagt atttggtatc    6660 tgcgctctgc tgaagccagt taccttcgga aaaagagttg gtagctcttg atccggcaaa    6720
caaaccaccg ctggtagcgg tggtttttt gtttgcaagc agcagattac gcgcagaaaa    6780
aaaggatctc aagaagatcc tttgatcttt tctacgggt ctgacgctca gtggaacgaa    6840
aactcacgtt aagggatttt ggtcatgaga ttatcaaaaa ggatcttcac ctagatcctt    6900
```

```
ttaaattaaa aatgaagttt taaatcaatc taaagtatat atgagtaaac ttggtctgac    6960
agttaccaat gcttaatcag tgaggcacct atctcagcga tctgtctatt tcgttcatcc    7020
atagttgcct gactccccgt cgtgtagata actacgatac gggagggctt accatctggc    7080
cccagtgctg caatgatacc gcgagaccca cgctcaccgg ctccagattt atcagcaata    7140
aaccagccag ccggaagggc cgagcgcaga agtggtcctg caactttatc cgcctccatc    7200
cagtctatta attgttgccg ggaagctaga gtaagtagtt cgccagttaa tagttttgcgc    7260 aacgttgttg ccattgctgc aggcatcgtg gtgtcacgct cgtcgtttgg tatggcttca    7320
ttcagctccg gttcccaacg atcaaggcga gttacatgat cccccatgtt gtgcaaaaaa    7380
gcggttagct ccttcggtcc tccgatcgtt gtcagaagta agttggccgc agtgttatca    7440
ctcatggtta tggcagcact gcataattct cttactgtca tgccatccgt aagatgcttt    7500
tctgtgactg gtgagtactc aaccaagtca ttctgagaat agtgtatgcg gcgaccgagt    7560
tgctcttgcc cggcgtcaac acgggataat accgcgccac atagcagaac tttaaaagtg    7620
ctcatcattg gaaaacgttc ttcggggcga aaactctcaa ggatcttacc gctgttgaga    7680
tccagttcga tgtaacccac tcgtgcaccc aactgatctt cagcatcttt tactttcacc    7740
agcgtttctg ggtgagcaaa aacaggaagg caaaatgccg caaaaaaggg aataagggcg    7800
acacggaaat gttgaatact catactcttc ctttttcaat attattgaag catttatcag    7860
ggttattgtc tcatgagcgg atacatattt gaatgtattt agaaaaataa acaaataggg    7920
gttccgcgca catttccccg aaaagtgcca cctgacgtct aagaaaccat tattatcatg    7980
acattaacct ataaaaatag gcgtatcacg aggccctttc gtcttcaaga attaattctc    8040
atgtttgaca gcttatcatc gataagctga ctcatgttgg tattgtgaaa tagacgcaga    8100
tcgggaacac tgaaaaataa cagttattat tcgagatcta acatccaaag acgaaaggtt    8160
gaatgaaacc tttttgccat ccgacatcca caggtccatt ctcacacata agtgccaaac    8220
gcaacaggag gggatacact agcagcagac cgttgcaaac gcaggacctc cactcctctt    8280
ctcctcaaca cccactttg ccatcgaaaa accagcccag ttattgggct tgattggagc    8340
tcgctcattc caattccttc tattaggcta ctaacaccat gactttatta gcctgtctat    8400
cctggccccc ctggcgaggt tcatgttttgt ttatttccga atgcaacaag ctccgcatta    8460
cacccgaaca tcactccaga tgagggcttt ctgagtgtgg ggtcaaatag tttcatgttc    8520
cccaaatggc caaaactga cagttt                                           8546
```

<210> SEQ ID NO 34
<211> LENGTH: 8537
<212> TYPE: DNA
<213> ORGANISM: Artificial Sequence
<220> FEATURE:
<223> OTHER INFORMATION: plasmid pBCS12772
<220> FEATURE:
<221> NAME/KEY: misc_feature
<222> LOCATION: (1)..(8537)

<400> SEQUENCE: 34

```
tcaatattat tgaagcattt atcagggtta ttgtctcatg agcggataca tatttgaatg      60
tatttagaaa aataaacaaa tagggggttcc gcgcacattt ccccgaaaag tgccacctga    120
cgtctaagaa accattatta tcatgacatt aacctataaa aataggcgta tcacgaggcc    180
ctttcgtctt caagaattaa ttctcatgtt gacagctta tcatcgataa gctgactcat    240
gttggtattg tgaaatagac gcagatcggg aacactgaaa ataacagtt attattcgag    300
```

-continued

```
atctaacatc caaagacgaa aggttgaatg aaacctttt gccatccgac atccacaggt    360
ccattctcac acataagtgc caaacgcaac aggaggggat acactagcag cagaccgttg    420
caaacgcagg acctccactc ctcttctcct caacacccac ttttgccatc gaaaaaccag    480
cccagttatt gggcttgatt ggagctcgct cattccaatt ccttctatta ggctactaac    540
accatgactt tattagcctg tctatcctgg ccccctggc gaggttcatg tttgtttatt    600
tccgaatgca acaagctccg cattacaccc gaacatcact ccagatgagg gctttctgag    660
tgtggggtca aatagtttca tgttccccaa atggcccaaa actgacagtt taaacgctgt    720
cttggaacct aatatgacaa agcgtgatc tcatccaaga tgaactaagt ttggttcgtt    780
gaaatgctaa cggccagttg gtcaaaaaga aacttccaaa agtcggcata ccgtttgtct    840
tgtttggtat tgattgacga atgctcaaaa ataatctcat taatgcttag cgcagtctct    900
ctatcgcttc tgaaccccgg tgcacctgtg ccgaaacgca aatggggaaa caccccgcttt    960
ttggatgatt atgcattgtc tccacattgt atgcttccaa gattctggtg gaatactgc   1020
tgatagccta acgttcatga tcaaaattta actgttctaa ccctacttg acagcaatat   1080
ataaacagaa ggaagctgcc ctgtcttaaa cctttttttt tatcatcatt attagcttac   1140
tttcataatt gcgactggtt ccaattgaca agcttttgat tttaacgact tttaacgaca   1200
acttgagaag atcaaaaaac aactaattat tcgaaacgag gaattcaaac gatgagattt   1260
ccttcaattt ttactgcagt tttattcgca gcatcctccg cattagctgc tccagtcaac   1320
actacaacag aagatgaaac ggcacaaatt ccggctgaag ctgtcatcgg ttactcagat   1380
ttagaagggg atttcgatgt tgctgttttg ccattttcca acagcacaaa taacgggtta   1440
ttgtttataa atactactat tgccagcatt gctgctaaag aagaagggg atctctcgag   1500
aagagggcat ctactgacta ctggcagaac tggactgacg gtggtggtac cgtgaacgct   1560
actaatggta gtgatggtaa ttactcagtt tcttggtcaa actgtggaaa cttcgtcgtt   1620
ggtaagggat ggacaaccgg atctgctact agagtaatca actacaatgc cggagctttt   1680
tctccttctg gtaatggtta cttggccttg tatggatgga caagaaactc tttgattgaa   1740
tattacgttg tggattcctg gggtacttat cgtccaactg aacatataaa aggtactgta   1800
acttctgacg gaggtaccta tgatatttac acaactacaa gaactaatgc tccatctatc   1860
gacggaaata acactacatt tacccagttt tggtctgtca gacaatctaa aagacctatt   1920
ggaactaata ataccataac tttcagtaat catgttaacg cttggaagtc aaaaggtatg   1980
aacttgggtt cctcctggtc ctaccaagtt ttggcaactg agggttacca atctagtggt   2040
tattcaaatg ttactgtctg gtaataggcg gccgcggaat tcgccttaga catgactgtt   2100
cctcagttca agttgggcac ttacgagaag accggtcttg ctagattcta atcaagagga   2160
tgtcagaatg ccatttgcct gagagatgca ggcttcattt ttgatacttt tttatttgta   2220
acctatatag tataggattt ttttgtcat tttgtttctt ctcgtacgag cttgctcctg   2280
atcagcctat ctcgcagctg atgaatatct tgtggtaggg gtttgggaaa atcattcgag   2340
tttgatgttt ttcttggtat ttcccactcc tcttcagagt acagaagatt aagtgagacg   2400
ttcgtttgtg cggatcctaa tgcggtagtt tatcacagtt aaattgctaa cgcagtcagg   2460
caccgtgtat gaaatctaac aatgcgctca tcgtcatcct cggcaccgtc acctggatg    2520
ctgtaggcat aggcttggtt atgccggtac tgccgggcct cttgcgggat atcgtccatt   2580
ccgacagcat cgccagtcac tatggcgtgc tgctagcgct atatgcgttg atgcaatttc   2640
tatgcgcacc cgttctcgga gcactgtccg accgctttgg ccgccgccca gtcctgctcg   2700
```

```
cttcgctact tggagccact atcgactacg cgatcatggc gaccacaccc gtcctgtgga      2760
tctatcgaat ctaaatgtaa gttaaaatct ctaaataatt aaataagtcc cagtttctcc      2820
atacgaacct taacagcatt gcggtgagca tctagacctt caacagcagc cagatccatc      2880
actgcttggc caatatgttt cagtccctca ggagttacgt cttgtgaagt gatgaacttc      2940
tggaaggttg cagtgttaac tccgctgtat tgacgggcat atccgtacgt tggcaaagtg      3000
tggttggtac cggaggagta atctccacaa ctctctggag agtaggcacc aacaaacaca      3060
gatccagcgt gttgtacttg atcaacataa gaagaagcat tctcgatttg caggatcaag      3120
tgttcaggag cgtactgatt ggacatttcc aaagcctgct cgtaggttgc aaccgatagg      3180
gttgtagagt gtgcaataca cttgcgtaca atttcaaccc ttggcaactg cacagcttgg      3240
ttgtgaacag catcttcaat tctggcaagc tccttgtctg tcatatcgac agccaacaga      3300
atcacctggg aatcaatacc atgttcagct tgagacagaa ggtctgaggc aacgaaatct      3360
ggatcagcgt atttatcagc aataactaga acttcagaag gcccagcagg catgtcaata      3420
ctacacaggg ctgatgtgtc attttgaacc atcatcttgg cagcagtaac gaactggttt      3480
cctggaccaa atattttgtc acacttagga acagttctg ttccgtaagc catagcagct      3540
actgcctggg cgcctcctgc tagcacgata cacttagcac caaccttgtg ggcaacgtag      3600
atgacttctg gggtaagggt accatccttc ttaggtggag atgcaaaaac aatttctttg      3660
caaccagcaa ctttggcagg aacacccagc atcaggaag tggaaggcag aattgcggtt       3720
ccaccaggaa tatagaggcc aactttctca ataggtcttg caaaacgaga gcagactaca      3780
ccagggcaag tctcaacttg caacgtctcc gttagttgag cttcatggaa tttcctgacg      3840
ttatctatag agagatcaat ggctctctta acgttatctg gcaattgcat aagttcctct      3900 gggaaggag cttctaacac aggtgtcttc aaagcgactc catcaaactt ggcagttagt       3960 tctaaaggg ctttgtcacc attttgacga acattgtcga caattggttt gactaattcc       4020
ataatctgtt ccgttttctg gataggacga cgaagggcat cttcaatttc ttgtgaggag      4080
gccttagaaa cgtcaatttt gcacaattca atacgacctt cagaagggac ttctttaggt      4140
ttggattctt ctttaggttg ttccttggtg tatcctggct tggcatctcc tttccttcta      4200
gtgaccttta gggacttcat atccaggttt ctctccacct cgtccaacgt cacaccgtac      4260
ttggcacatc taactaatgc aaaataaaat aagtcagcac attcccaggc tatatcttcc      4320
ttggatttag cttctgcaag ttcatcagct tcctccctaa ttttagcgtt caacaaaact      4380
tcgtcgtcaa ataaccgttt ggtataagaa ccttctggag cattgctctt acgatcccac      4440
aaggtggctt ccatggctct aagacccttt gattggccaa aacaggaagt gcgttccaag      4500
tgacagaaac caacacctgt ttgttcaacc acaaatttca agcagtctcc atcacaatcc      4560
aattcgatac ccagcaactt ttgagttgct ccagatgtag cacctttata ccacaaaccg      4620
tgacgacgag attggtagac tccagtttgt gtccttatag cctccggaat agacttttg      4680 gacgagtaca ccaggcccaa cgagtaatta aagagtcag ccaccaaagt agtgaataga      4740 ccatcgggc ggtcagtagt caaagacgcc aacaaatttt cactgacagg gaacttttg      4800 acatcttcag aaagttcgta ttcagtagtc aattgccgag catcaataat ggggattata      4860
ccagaagcaa cagtggaagt cacatctacc aactttgcgg tctcagaaaa agcataaaca      4920
gttctactac cgccattagt gaacttttc aaatcgccca gtggagaaga aaaaggcaca       4980
gcgatactag cattagcggg caaggatgca actttatcaa ccagggtcct atagataacc      5040
```

```
ctagcgcctg ggatcatcct ttggacaact ctttctgcca aatctaggtc caaaatcact    5100
tcattgatac cattattgta caacttgagc aagttgtcga tcagctcctc aaattggtcc    5160
tctgtaacgg atgactcaac ttgcacatta acttgaagct cagtcgattg agtgaacttg    5220
atcaggttgt gcagctggtc agcagcatag ggaaacacgg cttttcctac caaactcaag    5280
gaattatcaa actctgcaac acttgcgtat gcaggtagca agggaaatgt catacttgaa    5340
gtcggacagt gagtgtagtc ttgagaaatt ctgaagccgt atttttatta tcagtgagtc    5400
agtcatcagg agatcctcta cgccggacgc atcgtggccg gcatcaccgg cgccacaggt    5460
gcggttgctg gcgcctatat cgccgacatc accgatgggg aagatcgggc tcgccacttc    5520
gggctcatga gcgcttgttt cggcgtgggt atggtggcag ccccgtggc cggggggactg    5580 ttgggcgcca tctccttgca tgcaccattc cttgcgcgg cggtgctcaa cggcctcaac    5640
ctactactgg gctgcttcct aatgcaggag tcgcataagg gagagcgtcg agtatctatg    5700 attgaagta tgggaatggt gatacccgca ttcttcagtg tcttgaggtc tcctatcaga    5760
ttatgcccaa ctaaagcaac cggaggagga gatttcatgg taaatttctc tgacttttgg    5820
tcatcagtag actcgaactg tgagactatc tcggttatga cagcagaaat gtccttcttg    5880
gagacagtaa atgaagtccc accaataaag aaatccttgt tatcaggaac aaacttcttg    5940
tttcgaactt tttcggtgcc ttgaactata aatgtagag tggatatgtc gggtaggaat    6000
ggagcgggca aatgcttacc ttctggacct tcaagaggta tgtagggttt gtagatactg    6060
atgccaactt cagtgacaac gttgctattt cgttcaaacc attccgaatc cagagaaatc    6120
aaagttgttt gtctactatt gatccaagcc agtgcggtct tgaaactgac aatagtgtgc    6180
tcgtgttttg aggtcatctt tgtatgaata aatctagtct ttgatctaaa taatcttgac    6240
gagccagacg ataataccaa tctaaactct ttaaacgtta aaggacaagt atgtctgcct    6300
gtattaaacc ccaaatcagc tcgtagtctg atcctcatca acttgagggg cactatcttg    6360
ttttagagaa atttgcggag atgcgatatc gagaaaaagg tacgctgatt ttaaacgtga    6420
aatttatctc aagatctgct gcctcgcgcg tttcggtgat gacggtgaaa acctctgaca    6480
catgcagctc ccggagacgg tcacagcttg tctgtaagcg gatgccggga gcagacaagc    6540
ccgtcagggc gcgtcagcgg gtgttggcgg gtgtcgggc gcagccatga cccagtcacg    6600
tagcgatagc ggagtgtata ctggcttaac tatgcggcat cagagcagat tgtactgaga    6660
gtgcaccata tgcggtgtga ataccgcac agatgcgtaa ggagaaaata ccgcatcagg    6720
cgctcttccg cttcctcgct cactgactcg ctgcgctcgg tcgttcggct gcggcgagcg    6780
gtatcagctc actcaaaggc ggtaatacgg ttatccacag aatcagggga taacgcagga    6840
aagaacatgt gagcaaaagg ccagcaaaag gccaggaacc gtaaaaaggc cgcgttgctg    6900 gcgttttcc ataggctccg ccccctgac gagcatcaca aaaatcgacg ctcaagtcag    6960
aggtggcgaa acccgacagg actataaaga taccaggcgt ttccccctgg aagctccctc    7020
gtgcgctctc ctgttccgac cctgccgctt accggatacc tgtccgcctt tctcccttcg    7080
ggaagcgtgg cgctttctca atgctcacgc tgtaggtatc tcagttcggt gtaggtcgtt    7140
cgctccaagc tgggctgtgt gcacgaaccc cccgttcagc ccgaccgctg cgccttatcc    7200
ggtaactatc gtcttgagtc caacccgta agacacgact tatcgccact ggcagcagcc    7260
actggtaaca ggattagcag agcgaggtat gtaggcggtg ctacagagtt cttgaagtgg    7320
tggcctaact acggctacac tagaaggaca gtatttggta tctgcgctct gctgaagcca    7380
gttaccttcg gaaaaagagt tggtagctct tgatccggca aacaaaccac cgctggtagc    7440
```

```
ggtggttttt tgtttgcaa gcagcagatt acgcgcagaa aaaaaggatc tcaagaagat    7500
cctttgatct tttctacggg gtctgacgct cagtggaacg aaaactcacg ttaagggatt    7560
ttggtcatga gattatcaaa aaggatcttc acctagatcc ttttaaatta aaaatgaagt    7620
tttaaatcaa tctaaagtat atatgagtaa acttggtctg acagttacca atgcttaatc    7680
agtgaggcac ctatctcagc gatctgtcta tttcgttcat ccatagttgc ctgactcccc    7740
gtcgtgtaga taactacgat acgggagggc ttaccatctg gccccagtgc tgcaatgata    7800
ccgcgagacc cacgctcacc ggctccagat ttatcagcaa taaaccagcc agccggaagg    7860
gccgagcgca gaagtggtcc tgcaacttta tccgcctcca tccagtctat taattgttgc    7920
cgggaagcta gagtaagtag ttcgccagtt aatagtttgc gcaacgttgt tgccattgct    7980
gcaggcatcg tggtgtcacg ctcgtcgttt ggtatggctt cattcagctc cggttcccaa    8040
cgatcaaggc gagttacatg atcccccatg ttgtgcaaaa aagcggttag ctccttcggt    8100
cctccgatcg ttgtcagaag taagttggcc gcagtgttat cactcatggt tatggcagca    8160
ctgcataatt ctcttactgt catgccatcc gtaagatgct tttctgtgac tggtgagtac    8220
tcaaccaagt cattctgaga atagtgtatg cggcgaccga gttgctcttg cccggcgtca    8280
acacgggata taccgcgcc acatagcaga actttaaaag tgctcatcat tggaaaacgt     8340
tcttcggggc gaaaactctc aaggatctta ccgctgttga gatccagttc gatgtaaccc    8400
actcgtgcac ccaactgatc ttcagcatct tttactttca ccagcgtttc tgggtgagca    8460
aaaacaggaa ggcaaaatgc cgcaaaaaag ggaataaggg cgacacggaa atgttgaata    8520
ctcatactct tcctttt                                                   8537
```

<210> SEQ ID NO 35
<211> LENGTH: 12763
<212> TYPE: DNA
<213> ORGANISM: Artificial Sequence
<220> FEATURE:
<223> OTHER INFORMATION: plasmid pSYN12773
<220> FEATURE:
<221> NAME/KEY: misc_feature
<222> LOCATION: (1)..(12763)

<400> SEQUENCE: 35

```
aagacgaaag gttgaatgaa acctttttgc catccgacat ccacaggtcc attctcacac      60
ataagtgcca aacgcaacag gaggggatac actagcagca gaccgttgca aacgcaggac     120
ctccactcct cttctcctca acacccactt ttgccatcga aaaccagcc cagttattgg      180 gcttgattgg agctcgctca ttccaattcc ttctattagg ctactaacac catgacttta     240
ttagcctgtc tatcctggcc ccctggcga ggttcatgtt tgtttatttc cgaatgcaac      300
aagctccgca ttacacccga acatcactcc agatgagggc tttctgagtg tggggtcaaa     360
tagtttcatg ttccccaaat ggcccaaaac tgacagttta aacgctgtct ggaacctaa      420 tatgacaaaa gcgtgatctc atccaagatg aactaagttt ggttcgttga atgctaacg      480 gccagttggt caaaaagaaa cttccaaaag tcggcatacc gtttgtcttg tttggtattg     540
attgacgaat gctcaaaaat aatctcatta atgcttagcg cagtctctct atcgcttctg     600
aaccccggtg cacctgtgcc gaaacgcaaa tggggaaaca cccgcttttt ggatgattat     660
gcattgtctc cacattgtat gcttccaaga ttctggtggg aatactgctg atagcctaac     720
gttcatgatc aaaattaac tgttctaacc cctacttgac agcaatatat aaacagaagg      780
aagctgccct gtcttaaacc tttttttta tcatcattat tagcttactt tcataattgc      840
```

```
gactggttcc aattgacaag cttttgattt taacgacttt taacgacaac ttgagaagat    900
caaaaaacaa ctaattattc gaaacgagga attccgatga gatttccttc aatttttact    960
gcagttttat tcgcagcatc ctccgcatta gctgctccag tcaacactac aacagaagat   1020
gaaacggcac aaattccggc tgaagctgtc atcggttact cagatttaga aggggatttc   1080
gatgttgctg ttttgccatt ttccaacagc acaataacg gttattgtt tataaatact     1140
actattgcca gcattgctgc taaagaagaa ggggtatctc tcgagaagag ggcatctact   1200
gactactggc agaactggac tgacggtggt ggtaccgtga acgctactaa tggtagtgat   1260
ggtaattact cagtttcttg gtcaaactgt ggaaacttcg tcgttggtaa gggatggaca   1320
accggatctg ctactagagt aatcaactac aatgccggag cttttttctcc ttctggtaat  1380
ggttacttgg ccttgtatgg atggacaaga aactctttga ttgaatatta cgttgtggat   1440
tcctggggta cttatcgtcc aactggaaca tataaaggta ctgtaacttc tgacggaggt   1500
acctatgata tttacacaac tacaagaact aatgctccat ctatcgacgg aaataacact   1560
acatttaccc agttttggtc tgtcagacaa tctaaaagac ctattggaac taataatacc   1620
ataactttca gtaatcatgt taacgcttgg aagtcaaaag gtatgaactt gggttcctcc   1680
tggtcctacc aagttttggc aactgagggt taccaatcta gtggttattc aaatgttact   1740
gtctggtaat aggcggccgc ggaattcgcc ttagacatga ctgttcctca gttcaagttg   1800
ggcacttacg agaagaccgg tcttgctaga ttctaatcaa gaggatgtca gaatgccatt   1860
tgcctgagag atgcaggctt cattttttgat acttttttat ttgtaaccta tatagtatag  1920
gatttttttt gtcatttttgt ttcttctcgt acgagcttgc tcctgatcag cctatctcgc  1980
agctgatgaa tatcttgtgg taggggtttg ggaaaatcat tcgagtttga tgtttttctt   2040
ggtatttccc actcctcttc agagtacaga agattaagtg agacgttcgt tgtgcggat    2100
ctaacatcca aagacgaaag gttgaatgaa ccttttgc catccgacat ccacaggtcc     2160
attctcacac ataagtgcca acgcaacag gaggggatac actagcagca gaccgttgca    2220
aacgcaggac ctccactcct cttctcctca cacccactt tgccatcga aaaccagcc      2280
cagttattgg gcttgattgg agctcgctca ttccaattcc ttctattagg ctactaacac   2340
catgactttta ttagcctgtc tatcctggcc cccctggcga ggttcatgtt tgtttatttc  2400
cgaatgcaac aagctccgca ttacacccga acatcactcc agatgagggc tttctgagtg   2460
tggggtcaaa tagtttcatg ttccccaaat ggcccaaaac tgacagttta aacgctgtct   2520
tggaacctaa tatgacaaaa gcgtgatctc atccaagatg aactaagttt ggttcgttga   2580
aatgctaacg gccagttggt caaaagaaa cttccaaaag tcggcatacc gtttgtcttg    2640
tttggtattg attgacgaat gctcaaaaat aatctcatta atgcttagcg cagtctctct   2700
atcgcttctg aaccccggtg cacctgtgcc gaaacgcaaa tggggaaaca cccgcttttt   2760
ggatgattat gcattgtctc cacattgtat gcttccaaga ttctggtggg aatactgctg   2820
atagcctaac gttcatgatc aaaatttaac tgttctaacc cctacttgac agcaatatat   2880
aaacagaagg aagctgccct gtcttaaacc ttttttttta tcatcattat tagcttactt   2940
tcataattgc gactggttcc aattgacaag cttttgattt taacgacttt taacgacaac   3000
ttgagaagat caaaaaacaa ctaattattc gaaggatcga tccaaacgat gagatttcct   3060
tcaattttta ctgcagtttt attcgcagca tcctccgcat tagctgctcc agtcaacact   3120
acaacagaag atgaaacggc acaaattccg gctgaagctg tcatcggtta ctcagattta   3180
```

```
gaaggggatt tcgatgttgc tgttttgcca ttttccaaca gcacaaataa cgggttattg    3240
tttataaata ctactattgc cagcattgct gctaaagaag aaggggtatc tctcgagaag    3300
agggcatcta ctgactactg gcagaactgg actgacggtg gtggtaccgt gaacgctact    3360
aatggtagtg atggtaatta ctcagtttct tggtcaaact gtggaaactt cgtcgttggt    3420
aagggatgga caaccggatc tgctactaga gtaatcaact acaatgccgg agcttttcct    3480
ccttctggta atggttactt ggccttgtat ggatggacaa gaaactcttt gattgaatat    3540
tacgttgtgg attcctgggg tacttatcgt ccaactggaa catataaagg tactgtaact    3600
tctgacggag gtacctatga tatttacaca actacaagaa ctaatgctcc atctatcgac    3660
ggaaataaca ctacatttac ccagttttgg tctgtcagac aatctaaaag acctattgga    3720
actaataata ccataacttt cagtaatcat gttaacgctt ggaagtcaaa aggtatgaac    3780
ttgggttcct cctggtccta ccaagttttg gcaactgagg gttaccaatc tagtggttat    3840
tcaaatgtta ctgtctggta ataggcggcc gcgaattaat tcgccttaga catgactgtt    3900
cctcagttca agttgggcac ttacgagaag accggtcttg ctagattcta atcaagagga    3960
tgtcagaatg ccatttgcct gagagatgca ggcttcattt ttgatacttt tttatttgta    4020
acctatatag tataggattt tttttgtcat tttgtttctt ctcgtacgag cttgctcctg    4080
atcagcctat ctcgcagctg atgaatatct tgtggtaggg gttgggaaa atcattcgag    4140 tttgatgttt ttcttggtat ttcccactcc tcttcagagt acagaagatt aagtgagacg    4200
ttcgtttgtg cggatctaac atccaaagac gaaaggttga atgaaccttt tttgccatcc    4260
gacatccaca ggtccattct cacacataag tgccaaacgc aacaggaggg gatacactag    4320
cagcagaccg ttgcaaacgc aggacctcca ctcctcttct cctcaacacc cacttttgcc    4380
atcgaaaaac cagcccagtt attgggcttg attggagctc gctcattcca attccttcta    4440
ttaggctact aacaccatga ctttattagc ctgtctatcc tggccccct ggcgaggttc    4500 atgtttgttt atttccgaat gcaacaagct ccgcattaca cccgaacatc actccagatg    4560
agggctttct gagtgtgggg tcaaatagtt tcatgttccc caaatggccc aaaactgaca    4620
gtttaaacgc tgtcttggaa cctaatatga caaaagcgtg atctcatcca agatgaacta    4680
agtttggttc gttgaaatgc taacggccag ttggtcaaaa agaaacttcc aaaagtcggc    4740
ataccgtttg tcttgtttgg tattgattga cgaatgctca aaaataatct cattaatgct    4800
tagcgcagtc tctctatcgc ttctgaaccc cggtgcacct gtgccgaaac gcaaatgggg    4860
aaacacccgc ttttggatg attatgcatt gtctccacat tgtatgcttc caagattctg    4920
gtgggaatac tgctgatagc ctaacgttca tgatcaaaat ttaactgttc taacccctac    4980
ttgacagcaa tatataaaca gaaggaagct gccctgtctt aaacctttt ttttatcatc    5040 attattagct tactttcata attgcgactg gttccaattg acaagctttt gattttaacg    5100
acttttaacg acaacttgag aagatcaaaa acaactaat tattcgaagg atcgatccaa    5160
acgatgagat ttccttcaat ttttactgca gttttattcg cagcatcctc cgcattagct    5220
gctccagtca acactacaac agaagatgaa acggcacaaa ttccggctga agctgtcatc    5280
ggttactcag atttagaagg ggatttcgat gttgctgttt tgccattttc caacagcaca    5340
aataacgggt tattgtttat aaatactact attgccagca ttgctgctaa agaagaaggg    5400
gtatctctcg agaagagggc atctactgac tactggcaga actggactga cggtggtggt    5460
accgtgaacg ctactaatgg tagtgatggt aattactcag tttcttggtc aaactgtgga    5520
aacttcgtcg ttggtaaggg atggacaacc ggatctgcta ctagagtaat caactacaat    5580
```

```
gccggagctt tttctccttc tggtaatggt tacttggcct tgtatggatg gacaagaaac   5640
tctttgattg aatattacgt tgtggattcc tggggtactt atcgtccaac tggaacatat   5700
aaaggtactg taacttctga cggaggtacc tatgatattt acacaactac aagaactaat   5760
gctccatcta tcgacggaaa taacactaca tttacccagt tttggtctgt cagacaatct   5820
aaaagaccta ttggaactaa taataccata actttcagta atcatgttaa cgcttggaag   5880
tcaaaaggta tgaacttggg ttcctcctgg tcctaccaag ttttggcaac tgagggttac   5940
caatctagtg gttattcaaa tgttactgtc tggtaatagg cggccgcgaa ttaattcgcc   6000
ttagacatga ctgttcctca gttcaagttg ggcacttacg agaagaccgg tcttgctaga   6060
ttctaatcaa gaggatgtca gaatgccatt tgcctgagag atgcaggctt catttttgat   6120
acttttttat ttgtaaccta tatagtatag gatttttttt gtcatttttgt ttcttctcgt   6180
acgagcttgc tcctgatcag cctatctcgc agctgatgaa tatcttgtgg taggggtttg   6240
ggaaaatcat tcgagtttga tgttttttctt ggtatttccc actcctcttc agagtacaga   6300
agattaagtg agacgttcgt ttgtgcggat ccaatgcggt agtttatcac agttaaattg   6360
ctaacgcagt caggcaccgt gtatgaaatc taacaatgcg ctcatcgtca tcctcggcac   6420
cgtcaccctg gatgctgtag gcataggctt ggttatgccg gtactgccgg gcctcttgcg   6480
ggatatcgtc cattccgaca gcatcgccag tcactatggc gtgctgctag cgctatatgc   6540
gttgatgcaa tttctatgcg cacccgttct cggagcactg tccgaccgct ttggccgccg   6600
cccagtcctg ctcgcttcgc tacttggagc cactatcgac tacgcgatca tggcgaccac   6660
acccgtcctg tggatctatc gaatctaaat gtaagttaaa atctctaaat aattaaataa   6720
gtcccagttt ctccatacga accttaacag cattgcggtg agcatctaga ccttcaacag   6780
cagccagatc catcactgct tggccaatat gtttcagtcc ctcaggagtt acgtcttgtg   6840
aagtgatgaa cttctggaag gttgcagtgt taactccgct gtattgacgg gcatatccgt   6900
acgttggcaa agtgtggttg gtaccggagg agtaatctcc acaactctct ggagagtagg   6960
caccaacaaa cacagatcca gcgtgttgta cttgatcaac ataagaagaa gcattctcga   7020
tttgcaggat caagtgttca ggagcgtact gattggacat ttccaaagcc tgctcgtagg   7080
ttgcaaccga tagggttgta gagtgtgcaa tacacttgcg tacaatttca acccttggca   7140
actgcacagc ttggttgtga acagcatctt caattctggc aagctccttg tctgtcatat   7200
cgacagccaa cagaatcacc tgggaatcaa taccatgttc agcttgagac agaaggtctg   7260
aggcaacgaa atctggatca gcgtatttat cagcaataac tagaacttca gaaggcccag   7320
caggcatgtc aatactacac agggctgatg tgtcattttg aaccatcatc ttggcagcag   7380
taacgaactg gtttcctgga ccaaatattt tgtcacactt aggaacagtt tctgttccgt   7440
aagccatagc agctactgcc tgggcgcctc ctgctagcac gatacactta gcaccaacct   7500
tgtgggcaac gtagatgact tctggggtaa gggtaccatc cttcttaggt ggagatgcaa   7560
aaacaatttc tttgcaacca gcaactttgg caggaacacc cagcatcagg gaagtggaag   7620
gcagaattgc ggttccacca ggaatataga ggccaacttt ctcaataggt cttgcaaaac   7680
gagagcagac tacaccaggg caagtctcaa cttgcaacgt ctccgttagt tgagcttcat   7740
ggaatttcct gacgttatct atagagagat caatggctct cttaacgtta tctggcaatt   7800
gcataagttc ctctgggaaa ggagcttcta acacaggtgt cttcaaagcg actccatcaa   7860
acttggcagt tagttctaaa agggctttgt caccattttg acgaacattg tcgacaattg   7920
```

```
gtttgactaa ttccataatc tgttccgttt tctggatagg acgacgaagg gcatcttcaa    7980
tttcttgtga ggaggcctta gaaacgtcaa ttttgcacaa ttcaatacga ccttcagaag    8040
ggacttcttt aggtttggat tcttctttag gttgttcctt ggtgtatcct ggcttggcat    8100
ctcctttcct tctagtgacc tttagggact tcatatccag gtttctctcc acctcgtcca    8160
acgtcacacc gtacttggca catctaacta atgcaaaata aaataagtca gcacattccc    8220
aggctatatc ttccttggat ttagcttctg caagttcatc agcttcctcc ctaattttag    8280
cgttcaacaa aacttcgtcg tcaaataacc gtttggtata agaaccttct ggagcattgc    8340
tcttacgatc ccacaaggtg gcttccatgg ctctaagacc ctttgattgg ccaaaacagg    8400
aagtgcgttc caagtgacag aaaccaacac ctgtttgttc aaccacaaat ttcaagcagt    8460
ctccatcaca atccaattcg atacccagca acttttgagt tgctccagat gtagcacctt    8520
tataccacaa accgtgacga cgagattggt agactccagt ttgtgtcctt atagcctccg    8580
gaatagactt tttggacgag tacaccaggc ccaacgagta attagaagag tcagccacca    8640
aagtagtgaa tagaccatcg gggcggtcag tagtcaaaga cgccaacaaa atttcactga    8700
cagggaactt tttgacatct tcagaaagtt cgtattcagt agtcaattgc cgagcatcaa    8760
taatggggat tataccagaa gcaacagtgg aagtcacatc taccaacttt gcggtctcag    8820
aaaaagcata aacagttcta ctaccgccat tagtgaaact tttcaaatcg cccagtggag    8880
aagaaaaagg cacagcgata ctagcattag cgggcaagga tgcaacttta tcaaccaggg    8940
tcctatagat aaccctagcg cctgggatca tcctttggac aactcttcct gccaaatcta    9000
ggtccaaaat cacttcattg ataccattat tgtacaactt gagcaagttg tcgatcagct    9060
cctcaaattg gtcctctgta acggatgact caacttgcac attaacttga agctcagtcg    9120
attgagtgaa cttgatcagg ttgtgcagct ggtcagcagc atagggaaac acggcttttc    9180
ctaccaaact caaggaatta tcaaactctg caacacttgc gtatgcaggt agcaagggaa    9240
atgtcatact tgaagtcgga cagtgagtgt agtcttgaga aattctgaag ccgtattttt    9300
attatcagtg agtcagtcat caggagatcc tctacgccgg acgcatcgtg gccggcatca    9360
ccggcgccac aggtgcggtt gctggcgcct atatcgccga catcaccgat ggggaagatc    9420
gggctcgcca cttcgggctc atgagcgctt gtttcggcgt gggtatggtg gcaggccccg    9480
tggccggggg actgttgggc gccatctcct tgcatgcacc attccttgcg gcggcggtgc    9540
tcaacggcct caacctacta ctgggctgct tcctaatgca ggagtcgcat aagggagagc    9600
gtcgagtatc tatgattgga agtatgggaa tggtgatacc cgcattcttc agtgtcttga    9660
ggtctcctat cagattatgc ccaactaaag caaccggagg aggagatttc atggtaaatt    9720
tctctgactt ttggtcatca gtagactcga actgtgagac tatctcggtt atgacagcag    9780
aaatgtcctt cttggagaca gtaaatgaag tcccaccaat aaagaaatcc ttgttatcag    9840
gaacaaactt cttgtttcga acttttcgg tgccttgaac tataaaatgt agagtggata    9900
tgtcgggtag gaatggagcg ggcaaatgct taccttctgg accttcaaga ggtatgtagg    9960
gtttgtagat actgatgcca acttcagtga caacgttgct atttcgttca aaccattccg   10020
aatccagaga aatcaaagtt gtttgtctac tattgatcca agccagtgcg gtcttgaaac   10080
tgacaatagt gtgctcgtgt tttgaggtca tctttgtatg aataaatcta gtctttgatc   10140
taaataatct tgacgagcca gacgataata ccaatctaaa ctctttaaac gttaaaggac   10200
aagtatgtct gcctgtatta aaccccaaat cagctcgtag tctgatcctc atcaacttga   10260
ggggcactat cttgttttag agaaatttgc ggagatgcga tatcgagaaa aaggtacgct   10320
```

```
gattttaaac gtgaaattta tctcaagatc tgctgcctcg cgcgtttcgg tgatgacggt   10380
gaaaacctct gacacatgca gctcccggag acggtcacag cttgtctgta agcggatgcc   10440
gggagcagac aagcccgtca gggcgcgtca gcgggtgttg gcgggtgtcg gggcgcagcc   10500
atgacccagt cacgtagcga tagcggagtg tatactggct taactatgcg gcatcagagc   10560
agattgtact gagagtgcac catatgcggt gtgaaatacc gcacagatgc gtaaggagaa   10620
aataccgcat caggcgctct ccgcttcct cgctcactga ctcgctgcgc tcggtcgttc   10680
ggctgcggcg agcggtatca gctcactcaa aggcggtaat acggttatcc acagaatcag   10740
gggataacgc aggaaagaac atgtgagcaa aaggccagca aaaggccagg aaccgtaaaa   10800
aggccgcgtt gctggcgttt ttccataggc tccgccccc tgacgagcat cacaaaaatc   10860
gacgctcaag tcagaggtgg cgaaacccga caggactata aagataccag gcgtttcccc   10920
ctggaagctc cctcgtgcgc tctcctgttc cgaccctgcc gcttaccgga tacctgtccg   10980
cctttctccc ttcgggaagc gtggcgcttt ctcatagctc acgctgtagg tatctcagtt   11040
cggtgtaggt cgttcgctcc aagctgggct gtgtgcacga accccccgtt cagcccgacc   11100
gctgcgcctt atccggtaac tatcgtcttg agtccaaccc ggtaagacac gacttatcgc   11160
cactggcagc agccactggt aacaggatta gcagagcgag gtatgtaggc ggtgctacag   11220
agttcttgaa gtggtggcct aactacggct acactagaag gacagtattt ggtatctgcg   11280
ctctgctgaa gccagttacc ttcggaaaaa gagttggtag ctcttgatcc ggcaaacaaa   11340
ccaccgctgg tagcggtggt ttttttgttt gcaagcagca gattacgcgc agaaaaaaag   11400
gatctcaaga agatccttg atcttttcta cggggtctga cgctcagtgg aacgaaaact   11460
cacgttaagg gattttggtc atgagattat caaaaaggat cttcacctag atccttttaa   11520
attaaaaatg aagttttaaa tcaatctaaa gtatatatga gtaaacttgg tctgacagtt   11580
accaatgctt aatcagtgag gcacctatct cagcgatctg tctatttcgt tcatccatag   11640
ttgcctgact ccccgtcgtg tagataacta cgatacggga gggcttacca tctggcccca   11700
gtgctgcaat gataccgcga gacccacgct caccggctcc agatttatca gcaataaacc   11760
agccagccgg aagggccgag cgcagaagtg gtcctgcaac tttatccgcc tccatccagt   11820
ctattaattg ttgccgggaa gctagagtaa gtagttcgcc agttaatagt ttgcgcaacg   11880
ttgttgccat tgctgcaggc atcgtggtgt cacgctcgtc gtttggtatg gcttcattca   11940
gctccggttc ccaacgatca aggcgagtta catgatcccc catgttgtgc aaaaaagcgg   12000
ttagctcctt cggtcctccg atcgttgtca gaagtaagtt ggccgcagtg ttatcactca   12060
tggttatggc agcactgcat aattctctta ctgtcatgcc atccgtaaga tgcttttctg   12120
tgactggtga gtactcaacc aagtcattct gagaatagtg tatgcggcga ccgagttgct   12180
cttgcccggc gtcaacacgg gataataccg cgccacatag cagaacttta aaagtgctca   12240
tcattggaaa acgttcttcg gggcgaaaac tctcaaggat cttaccgctg ttgagatcca   12300
gttcgatgta acccactcgt gcacccaact gatcttcagc atcttttact ttcaccagcg   12360
tttctgggtg agcaaaaaca ggaaggcaaa atgccgcaaa aaagggaata agggcgacac   12420
ggaaatgttg aatactcata ctcttccttt ttcaatatta ttgaagcatt tatcagggtt   12480
attgtctcat gagcggatac atatttgaat gtatttagaa aaataaacaa ataggggttc   12540
gcgcacatt tccccgaaaa gtgccacctg acgtctaaga aaccattatt atcatgacat   12600
taacctataa aaataggcgt atcacgaggc cctttcgtct tcaagaatta attctcatgt   12660
```

```
ttgacagctt atcatcgata agctgactca tgttggtatt gtgaaataga cgcagatcgg    12720
gaacactgaa aaataacagt tattattcga gatctaacat cca                       12763
```

<210> SEQ ID NO 36
<211> LENGTH: 9
<212> TYPE: DNA
<213> ORGANISM: Artificial Sequence
<220> FEATURE:
<223> OTHER INFORMATION: kex2
<220> FEATURE:
<221> NAME/KEY: misc_feature
<222> LOCATION: (1)..(9)

<400> SEQUENCE: 36

```
ctcgagaag                                                                9
```

<210> SEQ ID NO 37
<211> LENGTH: 3
<212> TYPE: PRT
<213> ORGANISM: Artificial Sequence
<220> FEATURE:
<223> OTHER INFORMATION: kex2 peptide
<220> FEATURE:
<221> NAME/KEY: misc_feature
<222> LOCATION: (1)..(3)

<400> SEQUENCE: 37

Gly Leu Arg
1

<210> SEQ ID NO 38
<211> LENGTH: 243
<212> TYPE: DNA
<213> ORGANISM: Saccharomyces cerevisiae
<220> FEATURE:
<221> NAME/KEY: CDS
<222> LOCATION: (1)..(243)

<400> SEQUENCE: 38

```
atg aga ttt cct tca att ttt act gca gtt tta ttc gca gca tcc tcc      48
Met Arg Phe Pro Ser Ile Phe Thr Ala Val Leu Phe Ala Ala Ser Ser
1               5                   10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
65                  70                  75                  80 tct                                                                 243
Ser
```

<210> SEQ ID NO 39
<211> LENGTH: 81
<212> TYPE: PRT
<213> ORGANISM: Saccharomyces cerevisiae

<400> SEQUENCE: 39

Met Arg Phe Pro Ser Ile Phe Thr Ala Val Leu Phe Ala Ala Ser Ser
1               5                   10                  15

-continued

```
Ala Leu Ala Ala Pro Val Asn Thr Thr Thr Glu Asp Glu Thr Ala Gln
        20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
 65                  70                  75                  80

Ser
```

MICROBIALLY EXPRESSES XYLANASES AND THEIR USE AS FEED ADDITIVES AND OTHER USES

CROSS-REFERENCE TO RELATED APPLICATIONS

This application is a divisional of U.S. application Ser. No. 11/018,645, filed on Dec. 20, 2004, now U.S. Pat. No. 7,291,493, which claims the benefit of U.S. Provisional Patent Application No. 60/531,404 filed Dec. 19, 2003, all of which is herein incorporated by reference.

FIELD OF THE INVENTION

The present invention relates to codon-optimized xylanase coding sequences and the expression of xylanases in microbes and yeast. The invention further relates to using multiple copies of the xylanase expression construct for high levels of protein expression. The invention also relates to the use of xylanases as feed or food additives. The invention also relates to methods of expression of enzymes to increase thermotolerance by expressing them in organisms that glycosylate proteins compared to expression that the same enzyme without the glycosylation. Further, the invention relates to methods of preparing feed, enzyme feed additives, and methods of reducing the feed conversion ratio or increasing weight gain of animals.

BACKGROUND OF THE INVENTION

Non-starch polysaccharides (NSP) have been implicated in the variability of the nutritional quality of cereals for chickens, associated with changes in viscosity of digesta (Bedford, M. R. & H. L. Classen (1993) "An in vitro Assay for Prediction of Broiler Intestinal Viscosity and Growth When Fed Rye-Based Diets in the Presence of Exogeneous Enzymes" *Poult. Sci.* 72, 137-143). Arabinoxylans are the major NSP of wheat and several commercially available xylanase enzyme products, produced from *Trichoderma*, *Humicola* and *Aspergillus* spp have been shown to reduce digesta viscosity and usually to improve the nutritive value of diets.

Xylans are linear polysaccharides formed from beta-1,4-linked D-xylopyranoses. In cereals, xylans frequently contain side chains of alpha-1,2, alpha-1,3, or alpha-1,2 and alpha-1,3 linked L-arabinofuranoside. These substituted xylans are commonly referred to as arabinoxylans. Xylanases (e.g., endo-1,4-beta-xylanase, EC 3.2.2.8) hydrolyze internal beta-1,4-xylosidic linkages in xylan to produce smaller molecular weight xylo-oligomers Xylanases can be used, e.g., in animal feed compositions which are rich in arabinoxylans and glucoxylans, in baking, in brewing, and in pulp and paper applications, e.g. to improve the bleachability of pulps. When added to feeds (e.g. for monogastric animals, including poultry or swine) which contain cereals (e.g. barley, wheat, maize, rye, triticale or oats) or cereal by-products, a hemicellulolytic enzyme improves the break-down of plant cell walls which leads to better utilization of the plant nutrients by the animal. This leads to improved growth rate and feed conversion. Also, the viscosity of the feeds containing xylan can be reduced.

In many of the practical applications, physical conditions (e.g., temperature and pH) hinder the use of xylanases; the xylanases must be active in the temperature and pH conditions of the process in which they are used. Formulation of commercial feed using pelleting, extrusion or expanding, often contains steps involving high temperatures (70-180° C.). Enzymes added to the formulation process should withstand these conditions. On the other hand, the corresponding temperature in the intestine of animals is about 40° C. Thus, ideal xylanases for feed compositions should withstand the above-mentioned extreme temperatures. In bleaching applications, xylanase application is not as simple as adding a xylanase treatment step. Because the bleaching process, and even the sequence of the steps used in the bleaching process varies in different pulp mills, there is thus a continuous need to find new xylanases active in different temperature and pH conditions.

Most commercial xylanases designed for feed applications are not very thermotolerant, especially when neutral or alkaline pH conditions are used. In practice, xylanases are generally inefficient or inactive at temperatures higher than 60° C. and often these enzymes work under acidic conditions. Generally, there are differences in the physical characteristics of xylanases of fungi and bacteria (for review, see Wong et al., Microbiol. Rev. 52:305-317 (1988)). Typically, fungal xylanases have a temperature optimum at about 50° C. and lower pH optimum than those of bacterial origin. Xylanases of bacterial origin generally have a temperature optimum in the range of 50 to 70° C. Numerous xylanases from fungal and bacterial microorganisms have been identified and characterized. (See, e.g., U.S. Pat. No. 5,437,992; Coughlin, M. P.; Biely, P. et al., "Proceedings of the second TRICEL symposium on *Trichoderma reesei* Cellulases and Other Hydrolases," Espoo 1993, P. Souminen and T. Reinikainen eds., Foundation for Biotechnical and Industrial Fermentation Research 8:125-135 (1993) and WO03/16654). In particular, three specific xylanases (XYL-I, XYL-II, and XYL-III) have been identified in *T. reesei* (Tenkanen, et al., Enzyme Microb. Technol. 14:566 (1992); Torronen, et al., Bio/Technology 10:1461 (1992); and Xu, et al., Appl. Microbiol. Biotechnol. 49:718 (1998)). Although numerous xylanases have been described in the literature, the need still exists to identify novel xylanases that are effective in applications such as those relating to animal feed and grain processing, biofuels, cleaning, fabric care, chemicals, plant processing, and delignifying and brightening of pulp and paper.

SUMMARY OF THE INVENTION

The present invention provides isolated nucleic acid molecules having the sequence of SEQ ID NOS:1, 3, 5 or 7, and expression cassettes, vectors and recombinant host cells comprising these sequences. The invention also provides methods of preparing a thermotolerant xylanase, comprising the steps of: expression in a microbial host cell an expression cassette comprising a promoter operably linked to a nucleic acid molecule encoding a xylanase which retains at least 40% activity after 30 minutes at 60° C. and has a specific activity of greater than 400 U/mg at a pH of less than pH 5.0 and greater than pH 1.5. The invention further provides a method of preparing a thermotolerant xylanase wherein the xylanase is glycosylated. The invention also provides an isolated thermotolerant xylanase produced by such methods. The invention also provides enzyme feed additives and animal feeds comprising a thermotolerant xylanase. The invention further provides methods of preparing a pelleted animal feed comprising a thermotolerant xylanase and pelleted animal feeds made by these methods. Also, the invention provides methods of decreasing the feed conversion ratio and increasing the weight gain of an animal, comprising the steps of feeding the animal an animal feed comprising the thermotolerant xylanase in an effective amount to decrease the feed conversion ratio in the animal. It also provides methods of improving the apparent metabolizable energy of animal feed comprising the step of formulating the animal feed with one or more thermotolerant xylanases in an effective amount to improve the apparent metabolizable energy of the feed. The invention also provides a method improving the nutritive value of animal feed or human food comprising the step of adding a thermotolerant xylanase during the preparation of animal feed or human food.

BRIEF DESCRIPTION OF THE SEQUENCE LISTING

Figure 1:
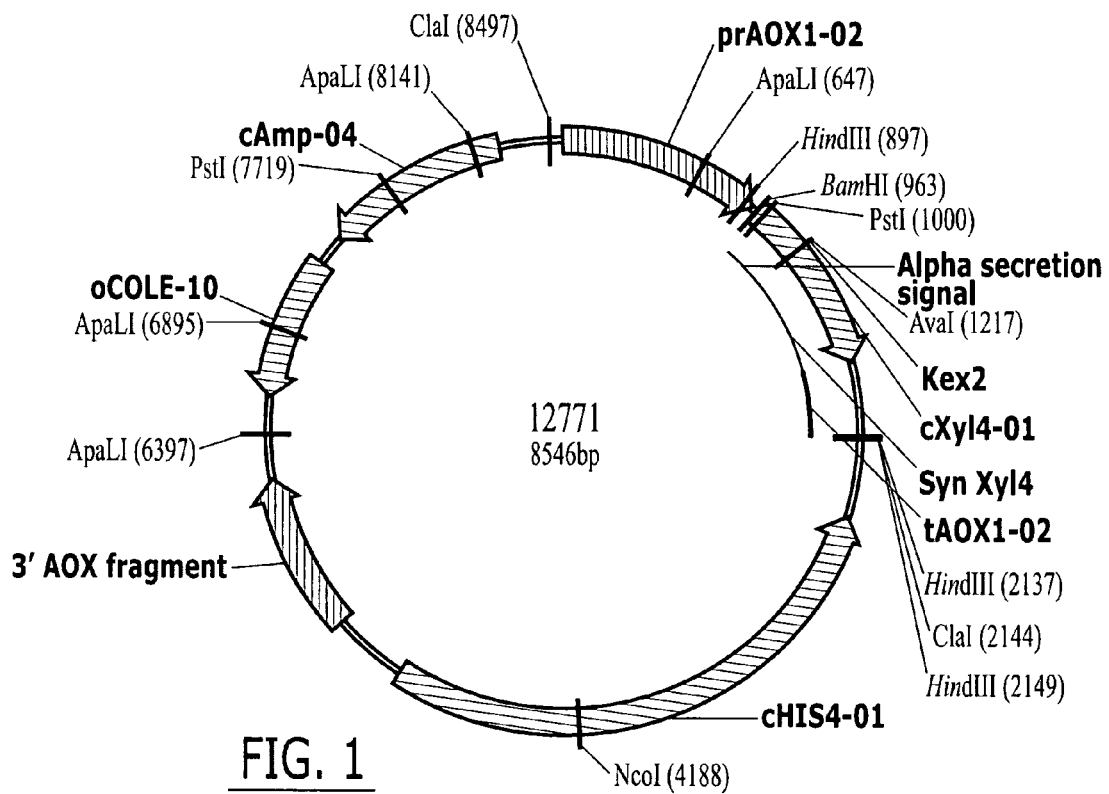
FIG. 1 is the vector map of plasmid pBCS12771.

SEQ ID NO:1 is the nucleotide sequence of the xylanase coding region of PP6002 (without the kex 2 protease cleavage site or AvaI restriction site). Codons optimized for expression in *Pichia*.
SEQ ID NO:2 is the amino acid sequence of the xylanase coding region of PP6002 (also the same as BD6002 without the secretion signal).
SEQ ID NO:3 is the nucleotide sequence of the xylanase coding region of PP6016 (without the kex2 protease cleavage site or AvaI restriction site). Codons optimized for expression in *Pichia*.
SEQ ID NO:4 is the amino acid sequence of the xylanase coding region of PP6016 (also the same amino acid sequence as BD6016 without the secretion signal).
SEQ ID NO:5 is the nucleotide sequence of the xylanase coding region of PP6407 (without the kex2 protease cleavage site or AvaI restriction site). Codons optimized for expression in *Pichia*.
SEQ ID NO:6 is the amino acid sequence of the xylanase coding region of PP6407 (also the same amino acid sequence as BD6407 without the secretion signal).
SEQ ID NO:7 is the nucleotide sequence of the xylanase coding region of PP7436 (without the kex2 protease cleavage site or AvaI restriction site). Codons optimized for expression in *Pichia*.
SEQ ID NO:8 is the amino acid sequence of the xylanase coding region of PP7436 (also the same amino acid sequence as BD7436 without the secretion signal).
SEQ ID NO:9 is the nucleotide sequence of the PP6002 comprising an AvaI restriction site, a kex2 protease cleavage site and a *Pichia* codon optimized xylanase.
SEQ ID NO:10 is the nucleotide sequence of PP6016 comprising an AvaI restriction site, a kex2 protease cleavage site and a *Pichia* codon optimized xylanase.
SEQ ID NO:11 is the nucleotide sequence of PP6407 comprising an AvaI restriction site, a kex2 protease cleavage site and a *Pichia* codon optimized xylanase.
SEQ ID NO:12 is the nucleotide sequence of PP7436 comprising an AvaI restriction site, a kex2 protease cleavage site and a *Pichia* codon optimized xylanase.

SEQ ID NO:13 is the nucleotide sequence of xylanase XylA1A (also called BD6002 without the secretion signal).
SEQ ID NO:14 is the amino acid sequence of XylA1A (also referred to as BD6002) without the original secretion signal sequence.
SEQ ID NO:15 is the nucleotide sequence of xylanase XylA1B lacking a secretion signal sequence coding region (the full length sequence is also known as BD7436).
SEQ ID NO:16 is the amino acid sequence of xylanase XylA1B (BD7436) lacking the original secretion signal region.
SEQ ID NO:17 is the nucleotide sequence of xylanase XylA1C lacking a secretion signal sequence coding region (the full length sequence is also known as BD2230).
SEQ ID NO:18 is the amino acid sequence of xylanase XylA1C (BD2230) lacking a secretion signal sequence region.
SEQ ID NO:19 is the nucleotide sequence of xylanase XylA1D lacking a secretion signal sequence coding region (the full length sequence is also known as BD6016).
SEQ ID NO:20 is the amino acid sequence of xylanase XylA1D (BD6016) lacking a secretion signal sequence region.
SEQ ID NO:21 is the nucleotide sequence of xylanase XylA1E lacking a secretion signal sequence coding region (the full length sequence is also known as BD6407).
SEQ ID NO:22 is the amino acid sequence of xylanase XylA1E (BD6407) lacking a secretion signal sequence region.
SEQ ID NO:23 is the nucleotide sequence of Primer 1.
SEQ ID NO:24 is the nucleotide sequence of Primer 2.
SEQ ID NO:25 is the nucleotide sequence of Primer 3.
SEQ ID NO:26 is the nucleotide sequence of Primer 4.
SEQ ID NO:27 is the nucleotide sequence of Primer 5.
SEQ ID NO:28 is the nucleotide sequence of Primer 6.
SEQ ID NO:29 is the nucleotide sequence of Primer 7.
SEQ ID NO:30 is the nucleotide sequence of Primer 8.
SEQ ID NO:31 is the nucleotide sequence of Primer 9.
SEQ ID NO:32 is the nucleotide sequence of Primer 10.
SEQ ID NO:33 is the nucleotide sequence of plasmid pBCS12771.
SEQ ID NO: 34 is the nucleotide sequence of plasmid pBCS12772.
SEQ ID NO:35 is the nucleotide sequence of plasmid pSYN12773.
SEQ ID NO:36 is the nucleotide sequence encoding the kex2 protease cleavage site.
SEQ ID NO:37 is the amino acid sequence of the kex2 protease cleavage site.
SEQ ID NO:38 is the nucleotide sequence encoding the *Saccharomyces cerevisiae* α-mating factor pre-pro-peptide secretion signal.
SEQ ID NO:39 is the amino acid sequence of the *Saccharomyces cerevisiae* α-mating factor pre-pro-peptide secretion signal peptide.

DETAILED DESCRIPTION OF THE INVENTION

The present invention relates to the use of a xylanase or xylanases, as well as the mutants and variants thereof, as an additive to animal feed, and to feedstuff that contains a xylanase.

The invention also relates to a method for improving the feed conversion ratio and/or the apparent metabolizable energy of feedstuffs using a xylanase or xylanases.

The invention provides a method of improving animal feed nutritive value. In this method, feed is formulated with one or more xylanases, such as for example, XylA1A, XylA1B, XylA1C, XylA1D, and XylA1E (SEQ ID NOS:13-22, respectively), for the purposes of improving feed nutrient utilization. The feed comprises any cereal grains since all contain xylans, but in particular wheat, rye, triticale, rice or corn, at an inclusion rate of less than 1.0%, more particularly, less than 0.1% w/w. The enzyme(s) is/are added to the feed using an inclusion rate of between 1 and 10000 U/kg. The enzyme(s) may be added to the feed prior to or following feed processing, which encompasses pelleting, expansion and extrusion although other methods exist, or simply added to unprocessed (mash) feed. Addition of one or more of these enzymes results in an increase in apparent metabolizable energy (AME) and/or a decrease in the feed conversion ratio (FCR) compared with unsupplemented diets.

The invention also provides methods of preparing and using a nucleic acid molecule (i.e., a polynucleotide) that encodes a xylanase. The xylanase may be thermotolerant, but it is not necessarily thermotolerant. Hence, the invention also relates to methods of preparing and using a nucleic acid molecule that encodes a thermotolerant xylanase. A thermotolerant xylanase includes those which retain at least 40% activity after 30 minutes at about 60° C. and which has a high specific activity, i.e., at least about 200 U/mg at 37° C. and at acid pH, e.g., pH 5.3. In another embodiment, the xylanase retains at least 40% activity after 30 minutes at 70° C., or retains at least 40% activity after 30 minutes at 80° C., or retains at least 40% activity after 30 minutes at 85° C. The method expresses xylanase that is a thermotolerant xylanase in the absence of glycosylation. Alternatively, the method emcompasses expressing a thermotolerant xylanase that is glycosylated by the host.

The invention also provides methods of preparing xylanases, including thermotolerant xylanases. The method comprises expressing in a microbial host cell an expression cassette comprising a promoter operably linked to a nucleic acid molecule encoding a xylanase. The microbial host cell may be a prokaryotic cell, such as a bacterial cell (e.g., *Escherichia*, *Pseudomonas*, *Lactobacillus*, and *Bacillus*), yeast (e.g., *Saccharomyces*, *Schizosaccharomyces*, *Pichia* or *Hansenula*) or fungal (e.g., *Aspergillus* or *Trichoderma*) cell. In particular, the host cell is *Pichia pastoris*. The microbial cell employed to prepare the recombinant xylanase may yield a glycosylated form of the recombinant xylanase.

The invention also provides the method of preparing a thermotolerant xylanase wherein the xylanase is encoded by the nucleotide sequence of SEQ ID NOS: 1, 3, 5 or 7. Further, the nucleic acid molecule encodes a fusion polypeptide comprising the xlyanase. The fusion protein can further comprise a secretion signal peptide operably linked to the xylanase.

The invention further comprises a polynucleotide encoding the xylanase operably linked to at least one regulatory sequence, such as a promoter, an enhancer, an intron, a termination sequence, or any combination thereof, and, optionally, to a second polynucleotide encoding a signal sequence, which directs the enzyme encoded by the first polynucleotide to a particular cellular location e.g., an extracellular location. Promoters can be constitutive promoters or inducible (conditional) promoters. As described herein, mutagenesis of a parent polynucleotide encoding a xylanase was employed to prepare variant (synthetic) DNAs encoding a xylanase having improved properties relative to the xylanase encoded by the parent polynucleotide. In an embodiment, xylanase enzymes are screened for improved activity at acidic or basic pH, improved intestinal stability, or improved expression level in host organisms. In another embodiment, the mutations in a number of the variant DNAs were combined to prepare a synthetic polynucleotide encoding a xylanase with enhanced thermotolerance and gastric stability and having a similar or a higher specific activity relative to the xylanase encoded by the parent polynucleotide. A parent polynucleotide may be obtained from any source including plant, bacterial or fungal nucleic acid, and any method may be employed to prepare a synthetic polynucleotide of the invention from a selected parent polynucleotide, e.g., combinatorial mutagenesis, recursive mutagenesis and/or DNA shuffling.

Thus, in one embodiment of the invention, the thermotolerant xylanase has one or more amino acid substitutions relative to a corresponding xylanase, which substitutions are associated with the retention of activity at temperatures equal to or greater than 60° C.

In another embodiment, the thermotolerant xylanase has at least 40% activity at about 60° C. for 30 minutes, or at least 40% activity at about 65° C. for 30 minutes, or at least 35% activity at 70° C. for 30 minutes, and which has a specific activity of at least 400 U/mg, more preferably at least 600 U/mg, and or at least 800 U/mg, at 37° C. and at acid pH, e.g., less than pH 6.0 or at less than pH 4.0 and greater than pH 1.5. One xylanase unit (XU) is the quantity of enzyme that liberates 1 μmol of reducing ends (xylose equivalents) per minute from WAXY (wheat arabinoxylan) at 37° C., pH 5.3, under standard conditions.

In another embodiment, the invention provides a method to make an enzyme thermotolerant due to glycosylation comprising the step of expressing the enzyme in *Pichia pastoris*. In a particular embodiment, the enzyme is a xylanase.

In an embodiment of the invention, is an isolated nucleic acid molecule having the sequence of SEQ ID NOS: 1, 3, 5, or 7. The invention also provides an expression cassette comprising a nucleic acid molecule comprising the nucleotide sequence of SEQ ID NOS: 1, 3, 5 or 7. The expression cassette can further comprise a proteolytic cleavage site such as the KEX2 protease cleavage site. In a more particular embodiment, the expression cassette is encoded by the nucleic acid sequence of SEQ ID NOS: 9, 10, 11 or 12. The expression cassette can further comprise an isolated nucleotide sequence encoding a secretion signal peptide, such as the *Saccharomyces cerevisiae* α-mating factor pre-pro-peptide secretion signal. The expression cassette can further comprise at least one nucleic acid molecule encoding a xylanase of the invention operably linked to a promoter.

The invention also provides recombinant host cells comprising at least one nucleic acid molecule of SEQ ID NOS; 1, 3, 5 or 7. The recombinant host cell can be a bacteria, yeast or fungal cell. In particular the host cell is *Escherichia, Pseudomonas, Lactobacillus, Bacillus, Saccharomyces, Schizosaccharomyces, Pichia, Hansenula, Aspergillus* or *Trichoderma* cell. In particular, the host cell is *Pichia pastoris*. In a more particular embodiment, the host cell comprises the vector pBCS12771, pBCS12772 or pSYN12773. In particular the host cell is *Pichia pastoris* comprising the vector pSYN12773.

Also provided by the invention are vectors comprising the expression cassette or polynucleotide of the invention, and transformed microbial cells comprising the polynucleotide, expression cassette or vector of the invention. A vector of the invention can encode more than one polypeptide including more than one xylanase or may encode a fusion polypeptide comprising the xylanase of the invention, and a transformed microbial cell may comprise one or more vectors of the invention. The transformed cells of the invention are useful for preparing the recombinant xylanase of the invention. Accordingly, the invention provides xylanase isolated from the transformed microbial cells of the invention, as well as synthetically prepared enzyme. In particular, the vectors comprise the plasmids designated pBCS12771 (SEQ ID NO:33), pBCS12772 (SEQ ID NO:34), or pSYN12773 (SEQ ID NO:35).

The invention also provides an isolated thermotolerant xylanase made by the method of the invention. Further, the isolated thermotolerant xylanase is glycosylated.

Further provided by the invention are methods for formulation of xylanases, xylanase formulations or formulated enzyme mixtures. The feed additives comprising thermotolerant xylanase comprise a thermotolerant xylanase of the invention. The feed additive formulations further comprise a stabilizing compound, such as but not limited to sorbital. The recombinant xylanase or formulations thereof may be added as a supplement to food or animal feed or to components of food and feed prior to, during, or after food or feed processing. Preferably, the recombinant xylanase of the invention is added to a mixture of feed components prior to and/or during heat (e.g., steam) conditioning in a pellet mill. Thus, the invention includes methods of making and using a xylanase.

Further, as a xylanase of the invention is capable of surviving the heat-conditioning step encountered in a commercial pellet mill during feed formulation, the invention provides a method of making animal feed, e.g., hard granular feed pellets comprising the xylanase. To make feed, the formulated xylanase may be mixed with feed components, the mixture steam conditioned in a pellet mill such that at least 50% of the pre-heat treated enzymatic activity is retained, and the feed extruded through a pellet dye. In another embodiment, greater than 70% of enzyme activity is recovered after pelleting at 85 C, or more particularly, greater than 90% of enzyme activity is recovered after pelleting at 85 C. In a particular embodiment, at least 80% of pre-treatement enzymatic activity is recovered after pelleting at 90° C.

The xylanase may thus be used as a supplement in animal feed by itself, in addition with vitamins, minerals, other feed enzymes, agricultural co-products (e.g., wheat middlings or corn gluten meal), or in a combination therewith. The enzyme may also be added to mash diets, i.e., diets that have not been through a pelletizer.

Some benefit of using xylanases in feed is produced during the feed manufacturing process, for example, during heat treatment when the temperatures would range from 75 to 95° C. as in traditional pelleting (expansion will be 105-125° C.). Such treatments can decrease the viscosity of the feed in the gut of the animal. See Silversides and Bedford, Poultry Sci. 78:1184-1190 (1999).

Xylanase enzymes that are not thermotolerant are often applied post pelleting, generally via spraying an enzyme solution onto pelleted feed. Some of the problems associated with spraying methods are that only a low percentage of the pellets are contacted with enzyme, the enzyme is only present on the surface of the coated pellets, and feed mills need to invest in and operate complex spraying machinery. In contrast, a thermotolerant xylanase of the invention, which may be added prior to pelleting, thereby facilitating production of a feed with an improved distribution of the enzyme. Moreover, feed comprising a thermotolerant xylanase of the invention may have a longer shelf life than feed sprayed with xylanase, as the spraying process introduces moisture which can support fungal and bacterial growth during storage. Current xylanases that are not thermotolerant can be made to survive high processing temperatures by coating with a wax layer to keep moisture out. This process is expensive, however, and reduces the efficacy of the product in low temperature pelleted diets or mash diets since the wax coating is slow to release the enzyme once introduced into the gut of the animal.

The invention thus provides a method of preparing animal feed comprising providing a mixture comprising one or more feed components and a preparation comprising a xylanase of the invention, such as a thermotolerant xylanase, and treating the mixture under appropriate conditions of temperature and moisture so as to hydrolyze xylan which is present in the mixture. Also provided is animal feed prepared by such a method. The animal feeds include, but are not limited to, poultry feed, swine feed or ruminant feeds.

Further provided is a method of preparing a xylanase containing composition for feed formulation comprising combining a liquid solution comprising the thermotolerant xylanase of the invention and meal flour, e.g., soy meal flour, to yield a mixture; and drying the mixture to yield a dried composition. Drying the mixture may be accomplished by techniques routinely used in the art, including but not limited to lyophilising and/or heating.

The invention further provides a method in which a mixture comprising animal feed components and a preparation comprising the xylanase of the invention is treated with heat so as to yield a heat-treated animal feed mixture. Heat-treated animal feed prepared by the method is also provided. The xylanase preparation may be a liquid or a solid preparation. In one embodiment, a liquid solution comprising a xylanase of the invention is combined with soy meal flour to yield a mixture and the mixture is then lyophilized. The mixture may also comprise at least one vitamin, mineral, an enzyme other than a xylanase, an organic acid, a probiotic product, an essential oil or a grain-processing co-product. The heat-treated feed may be further processed, for example, by extruding the heat-treated feed through a pellet mill to yield pelletized animal feed. Also provided is an animal feed composition comprising the xylanase of the invention, and an enzyme feed additive or a food additive comprising such a xylanase.

The invention further provides a pelletized animal feed. In one embodiment, the pelletized animal feed is steam conditioned in a pellet mill at about 85 C such that greater than 70% of the pre-heat treated enzymatic activity is retained, and the feed extruded through a pellet dye. In another embodiment, the pelletized animal feed is steam conditioned in a pellet mill at about 90 C such that at least 80% of the pre-heated enzymatic activity is retained, and the feed extruded through a pellet dye.

Also provided is a method of decreasing the feed conversion ratio and increasing the weight gain of an animal comprising the step of feeding to an animal a feed comprising a thermotolerant xylanase of the invention in an effective amount to decrease the feed conversion ratio in the animal and increase the weight gain of the animal.

The invention provides a method of improving the nutritive value of animal feed or human food. The method comprises the step of adding the xylanase of the invention during the preparation of animal feed or human food. Also provided is a method of preparing human food comprising providing a mixture of a food component and a preparation comprising the xylanase of the invention; and treating the mixture under appropriate conditions of temperature and moisture to facilitate hydrolysis of xylan.

The invention also provides a method for improving the apparent metabolizable energy (AME) of animal feed comprising the step of formulating the animal feed with one or more thermotolerant xylanases of the invention with the animal feed in an effective amount to improve the apparent metabolizable energy of the feed.

Animals within the scope of the invention include polygastric animals, e.g., calves, as well as monogastric animals including but not limited to, swine, poultry (e.g., chickens, turkeys, geese, ducks, pheasant, grouse, quail and ostrich), equine, ovine, caprine, canine and feline, as well as fish and crustaceans. Further, ruminant animals such as cows are included in the scope of the invention. The levels of xylanase in feed or food are added at an inclusion rate of between about 1 to 10000 U/kg, more particularly 50 to 5000 U/kg, or 200 to 3,200 U/kg.

The xylanase enzyme, as well as the enzyme mixtures described above, can in principle be added to all feedstuffs. Suitable and preferred examples are those which comply with the provisions of the feedstuffs legislation, such as complete feed, supplementary feed and mineral feed.

The invention is a method of improving animal feed nutritive value. In this method, feed is formulated with one or more of the enzymes, for example, XylA1A, XylA1B, XylA1C, XylA1D, and XylA1E, for the purposes of improving feed nutrient utilization. The feed may be composed of any cereal grains since all contain xylans, but in particular wheat, rye, triticale, rice or corn, at an inclusion rate of less than 1.0%, more particularly, less than 0.1% w/w. The enzyme(s) is/are added to this feed using an inclusion rate of between 1 and 10000 U/kg. The enzyme(s) may be added to the feed prior to or following feed processing, which encompasses pelleting, expansion and extrusion although other methods exist, or simply added to unprocessed (mash) feed. Addition of one or more of these enzymes results in an increase in apparent metabolizable energy (AME) and/or a decrease in the feed conversion ratio (FCR) compared with unsupplemented diets, but also in comparison with diets supplemented with the current commercial standard xylanases.

The enzyme dosed is in the range from 0.01 to 10,000 ppm, or alternatively in the range from 20 to 1000 ppm. The activity of xylanase enzyme product is normally stated in units (U).

The enzyme product, alone or in a mixture, is mixed with the feed batch wise in appropriate ratios by weight. In this connection, it is important that the active substances in the feed are homogeneously distributed.

Feedstuffs which contain a xylanase enzyme can be employed for feeding all livestock, but particularly advantageously for feeding agricultural livestock used for the production of foodstuffs, in particular broilers, turkeys, pigs and cattle.

Addition of the enzyme product or of the mixture to the feedstuffs brings about a considerable improvement in the utilization thereof and, connected with this, an improvement in growth of the livestock. The use thereof as additive to feedstuffs has, by comparison with additives having antibiotic activity, the great advantage that there is no risk of resistance development on use over a prolonged period.

Other Uses

Xylanases of the present invention can be used in any application for which other xylanases are used, such as but not limited to, grain processing, biofuels, cleaning, fabric care, chemicals, plant processing, and delignifying and brightening of pulp and paper.

Constructs and Host Cells of the Invention

The invention preferably provides an expression cassette comprising a nucleic acid sequence (promoter) capable of directing expression of a polynucleotide encoding a xylanase either in vitro or in vivo. Methods to prepare and/or identify a xylanase include mutagenesis, e.g., recursive mutagenesis, and/or selection or screening, e.g., for xylanases having activity at temperatures greater than 60° C. Methods for mutagenesis and nucleotide sequence alterations are well known in the art. See, for example, Kunkel, 1985; Kunkel et al., 1987; U.S. Pat. No. 4,873,192; Walker and Gaastra, 1983 and the references cited therein; and Arnold et al., 1996.

A. DNA and Host Cells for Transformation

Vectors, plasmids, cosmids, YACs (yeast artificial chromosomes) BACs (bacterial artificial chromosomes) and isolated nucleic acid molecules for use in transforming cells will generally comprise the xylanase encoding nucleic acid molecules, as well as other nucleic acid molecules such as cDNA, gene or genes which one desires to introduce into the cells. These nucleic acid constructs can further comprise nucleic acid molecules such as promoters, enhancers, polylinkers, or even regulatory genes as desired. One of the nucleic acid molecules or genes chosen for cellular introduction will often encode a protein which will be expressed in the resultant transformed (recombinant) cells, such as will result in a screenable or selectable trait and/or which will impart an improved phenotype to the transformed cell. However, this may not always be the case, and the present invention also encompasses transformed cells incorporating non-expressed transgenes.

Isolated nucleic acid molecules useful for introduction into cells comprise that which has been derived or isolated from any source, that may be subsequently characterized as to structure, size and/or function, chemically altered, and later introduced into cells. An example of an isolated nucleic acid molecule "derived" from a source, would be a nucleic acid sequence that is identified as a useful fragment within a given organism, and which is then chemically synthesized in essentially pure form. An example of such a nucleic acid molecule "isolated" from a source would be a useful nucleic acid molecule sequence that is excised or removed from said source by chemical means, e.g., by the use of restriction endonucleases, so that it can be further manipulated, e.g., amplified, for use in the invention, by the methodology of genetic engineering. Such a nucleic acid molecule is commonly referred to as "recombinant." Therefore useful nucleic acid molecules comprise completely synthetic nucleic acid molecules, semi-synthetic nucleic acid molecules, nucleic acid molecules isolated from biological sources, and nucleic acid molecules derived from introduced RNA. Generally, the introduced nucleic acid molecule is not originally resident in the genotype which is the recipient of the nucleic acid molecule, but it is within the scope of the invention to isolate a gene from a given genotype, and to subsequently introduce multiple copies of the gene into the same genotype, e.g., to enhance production of a given gene product.

The introduced nucleic acid molecule comprises, but is not limited to, nucleic acid molecules isolated from genes such as those from bacteria, yeasts, fungi, or viruses. The introduced nucleic acid molecule includes modified or synthetic genes, portions of genes, or chimeric genes, including genes from the same or different genotype. The term "chimeric gene" or "chimeric nucleic acid molecule" is defined as a gene or nucleic acid molecule sequence or segment comprising at least two nucleic acid sequences or segments from species which do not combine nucleic acid under natural conditions, or which nucleic acid sequences or segments are positioned or linked in a manner which does not normally occur in the native genome of the untransformed cell.

The introduced nucleic acid molecule used for transformation herein is circular or linear, double-stranded or single-stranded. Generally, the isolated nucleic acid molecule is in the form of chimeric DNA, such as plasmid DNA, that can also contain coding regions flanked by regulatory sequences which promote the expression of the recombinant DNA present in the transformed cell. For example, the nucleic acid molecule comprises or consists of a promoter that is active in a cell which is derived from a source other than that cell, or may utilize a promoter already present in the cell that is the transformation target.

Generally, the introduced nucleic acid molecule will be relatively small, i.e., less than about 30 kb to minimize any susceptibility to physical, chemical, or enzymatic degradation which is known to increase as the size of the nucleic acid molecule increases. The number of proteins, RNA transcripts or mixtures thereof, which is introduced into the cell is customarily pre-selected and defined, e.g., from one to about 5-10 such products of the introduced DNA may be formed.

The selection of an appropriate expression vector will depend upon the host cells. Typically an expression vector comprises (1) prokaryotic nucleic acid molecule elements coding for a bacterial origin of replication and an antibiotic resistance gene to provide for the amplification and selection of the expression vector in a bacterial host; (2) nucleic acid molecules that control initiation of transcription such as a promoter; (3) nucleic acid molecules that control the processing of transcripts such as introns, transcription termination/polyadenylation sequence; and (4) a nucleic acid molecule or gene of interest that is operatively linked to the nucleic acid molecule to control transcription initiation. In a particular embodiment, the xylanase gene and operable elements would not replicate autonomously in a host cell. The expression vector used may be one capable of autonomously replicating in the above host or capable of integrating into the chromosome, originally containing a promoter at a site enabling transcription of the linked xylanase gene.

If prokaryotes such as bacteria are used as the host, the expression vector for the xylanase is preferably one capable of autonomously replicating in the micro-organism and comprising a promoter, a ribosome-binding sequence, the novel xylanase gene, and a transcription termination sequence. The vector may also contain a gene for regulating the promoter.

Yeast or fungal expression vectors may comprise an origin of replication, a suitable promoter and enhancer, and also any necessary ribosome binding sites, polyadenylation site, splice donor and acceptor sites, transcriptional termination sequences, and 5' flanking nontranscribed sequences.

Suitable vectors include by way of example: for bacteria, pQE70, pQE60, pQE-9 (Qiagen), pBluescript II (Stratagene), pTRC99a, pKK223-3, pDR540, pRIT2T (Pharmacia); for eukaryotic cells: pXTI, pSG5 (Stratagene) pSVK3, pBPV, pMSG, pSVLSV40 (Pharmacia). Such commercial vectors include, for example, pKK223-3 (Pharmacia Fine Chemicals, Uppsala, Sweden) and GEMI (Promega Biotec, Madison, Wis., USA). However, any other plasmid or vector may be used as long as they are replicable and viable in the host.

As representative examples of appropriate hosts, there may be mentioned: bacterial cells, such as *E. coli, Streptomyces, Bacillus subtilis*; and various species within the genera *Escherichia, Pseudomonas, Serratia, Streptomyces, Corynebacterium, Brevibacterium, Bacillus, Microbacterium*, and *Staphylococcus*, although others may also be employed as a matter of choice; fungal cells belonging to the genera *Aspergillus, Rhizopus, Trichoderma, Neurospora, Mucor, Penicillium*, etc., such as yeast belonging to the genera *Kluyveromyces, Saccharomyces, Schizosaccharomyces, Trichosporon, Schwanniomyces, Pichia* and the like.

The construction of vectors which may be employed in conjunction with the present invention will be known to those of skill of the art in light of the present disclosure (see, e.g., Sambrook et al., *Molecular Cloning*, Cold Spring Harbor Press, 1989; Gelvin et al., *Plant Molecular Biology Manual*, 1990). The expression cassette of the invention may contain one or a plurality of restriction sites allowing for placement of the polynucleotide encoding a xylanase under the regulation of a regulatory sequence. The expression cassette may also contain a termination signal operably linked to the polynucleotide as well as regulatory sequences required for proper translation of the polynucleotide. The expression cassette containing the polynucleotide of the invention may be chimeric, meaning that at least one of its components is heterologous with respect to at least one of the other components. Expression of the polynucleotide in the expression cassette may be under the control of a constitutive promoter, inducible promoter, regulated promoter, viral promoter or synthetic promoter.

The expression cassette may include in the 5'-3' direction of transcription, a transcriptional and translational initiation region, the polynucleotide of the invention and a transcriptional and translational termination region functional in vivo and/or in vitro. The termination region may be native with the transcriptional initiation region, may be native with the polynucleotide, or may be derived from another source. The regulatory sequences may be located upstream (5' non-coding sequences), within (intron), or downstream (3' non-coding sequences) of a coding sequence, and influence the transcription, RNA processing or stability, and/or translation of the associated coding sequence. Regulatory sequences may include, but are not limited to, enhancers, promoters, repressor binding sites, translation leader sequences, introns, and polyadenylation signal sequences. They may include natural and synthetic sequences as well as sequences which may be a combination of synthetic and natural sequences.

The vector, used in the present invention may also include appropriate sequences for amplifying expression.

B. Regulatory Sequences

A promoter is a nucleotide sequence that controls the expression of a coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be derived entirely from a native gene, or be composed of different elements derived from different promoters found in nature, or even be comprised of synthetic DNA segments. A promoter may contain DNA sequences that are involved in the binding of protein factors that control the effectiveness of transcription initiation in response to physiological or developmental conditions. A promoter may also include a minimal promoter plus a regulatory element or elements capable of controlling the expression of a coding sequence or functional RNA. This type of promoter sequence contains of proximal and more distal elements, the latter elements are often referred to as enhancers.

Representative examples of promoters include, but are not limited to, promoters known to control expression of genes in prokaryotic or eukaryotic cells or their viruses. Particular bacterial promoters include *E. Coli* lac or trp, the phage lambda $P_L$, lacI, lacZ, T3, T7, gpt, and lambda $P_R$ promoters.

Any promoter capable of expressing in yeast hosts can be used as the promoter. Examples thereof include promoters for genes of hexokinase and the like in the glycolytic pathway, and promoters such as gal 1 promoter, gal 10 promoter, heat shock protein promoter, MFa-1 promoter and CUP 1 promoter.

Any promoter capable of expressing in filamentous fungi may be used. Examples are a promoter induced strongly by starch or cellulose, e.g., a promoter for glucoamylase or a-amylase from the genus *Aspergillus* or cellulase (cellobiohydrase) from the genus *Trichoderma*, a promoter for enzymes in the glycolytic pathway, such as phosphoglycerate kinase (pgk) and glycerylaldehyde 3-phosphate dehydrogenase (gpd), etc.

Two principal methods for the control of expression are known, viz.: over-expression and under-expression. Over-expression can be achieved by insertion of one or more than one extra copy of the selected gene. For under-expression there are two principle methods which are commonly referred to in the art as "antisense down-regulation" and "sense down-regulation". Generically these processes are referred to as "gene silencing". Both of these methods lead to an inhibition of expression of the target gene.

Several inducible promoters are known in the art. Many promoters are described in a review by Gatz, (Current Opinion in Biotech. 7(2):168-172 (1996) (see also Gatz, Annual Rev. Plant. Physiol. and Plant Mol. Biol. 48:89-108, 1997)). Examples include tetracycline repressor system, Lac repressor system, copper-inducible systems, salicylate-inducible systems (such as the PR1a system), glucocorticoid-inducible (Aoyama T. et al., Plant Journal 11(3):605-612, 1997) and ecdysome-inducible systems. Also included are the benzene sulphonamide-inducible system (U.S. Pat. No. 5,364,780), alcohol-inducible (WO 97/06269 and WO 97/06268) inducible systems and glutathione S-transferase promoters.

Regulated expression of a chimeric transacting viral replication protein can be further regulated by other genetic strategies. For example, Cre-mediated gene activation as described by Odell et al., (Molecular and General Genetics 223:369-378 1990). Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al., Plant Mol. Biol. 35(4):417-424, 1997. Again, either the chimeric tRNA suppressor gene, the chimeric transacting replication gene, or both can be under the control of developmental-specific or inducible promoters.

In addition to the use of a particular promoter, other types of elements can influence expression of transgenes. In particular, introns have demonstrated the potential for enhancing transgene expression.

Other elements include those that can be regulated by endogenous or exogenous agents, e.g., by zinc finger proteins, including naturally occurring zinc finger proteins or chimeric zinc finger proteins. See, e.g., U.S. Pat. No. 5,789,538, WO 99/48909; WO 99/45132; WO 98/53060; WO 98/53057; WO 98/53058; WO 00/23464; WO 95/19431; and WO 98/54311.

An enhancer is a DNA sequence which can stimulate promoter activity and may be an innate element of the promoter or a heterologous element inserted to enhance the level or tissue specificity of a particular promoter. An enhancer is capable of operating in both orientations (5' to 3' and 3'-5' relative to the gene of interest coding sequences), and is capable of functioning even when moved either upstream or downstream from the promoter. Both enhancers and other upstream promoter elements bind sequence-specific DNA-binding proteins that mediate their effects.

Vectors for use in accordance with the present invention may be constructed to include an enhancer element. Constructs of the invention will also include the gene of interest along with a 3' end DNA sequence that acts as a signal to terminate transcription and allow for the polyadenylation of the resultant mRNA.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure.

C. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., an antibiotic, or the like), or whether it is simply a trait that one can identify through observation or testing, i.e., by 'screening'. Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA and small active enzymes detectable in extracellular solution.

Selectable markers for use in prokaryotes include a tetracycline resistance or an ampillicin resistance gene. Screenable markers that may be employed include, but are not limited to, a b-glucuronidase or uidA gene (GUS) which encodes an enzyme for which various chromogenic substrates are known; a beta-lactamase gene (Sutcliffe, Proc. Natl. Acad. Sci. USA 75(8):3737-3741, 1978), which encodes an enzyme for which various chromogenic substrates are known (e.g., PADAC, a chromogenic cephalosporin); a xylE gene (Zukowsky et al., Proc. Natl. Acad. Sci. USA 80:1101, 1983) which encodes a catechol dioxygenase that can convert chromogenic catechols; an alpha-amylase gene (Ikuta et al., Biotechnology 8(3):241-242, 1990); a tyrosinase gene (Katz et al., J. General Microbiol. 129(Pt. 9):2703-14, 1983) which encodes an enzyme capable of oxidizing tyrosine to DOPA and dopaquinone which in turn condenses to form the easily detectable compound melanin; a beta-galactosidase gene, which encodes an enzyme for which there are chromogenic substrates; a luciferase (lux) gene (Ow et al., Science 234: 856-859, 1986), which allows for bioluminescence detection; or even an aequorin gene (Prasher et al., Biochem Biophys Res Commun. 126(3):1259-68, 1985), which may be employed in calcium-sensitive bioluminescence detection, or a green fluorescent protein gene (Niedz et al., Plant Cell Reports 14(7):403-406, 1995). The selectable marker may also be a negative selectable marker such as, but not limited to, transforming the gene into an organism that is ura3-genotype and using the ura3 system ±5FOA, ±uracil in the medium.

Transformation

The expression cassette, or a vector construct containing the expression cassette, may be inserted into a cell. The expression cassette or vector construct may be carried episomally or integrated into the genome of the cell, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any vector may be used as long as it is replicable and viable in the host.

A variety of techniques are available and known to those skilled in the art for introduction of constructs into a cellular host. Transformation of microbial cells may be accomplished through use of polyethylene glycol, calcium chloride, viral infection, DEAE dextran, phage infection, electroporation and other methods known in the art. Transformation of fungus, in particular Pichia, may be accomplished according to "Pichia Protocols", in Methods Mol. Biol., Higgins, David R. and Cregg, James M.; Eds. (Humana, Totowa, N.J.) (1998). Introduction of the recombinant vector into yeasts can be accomplished by methods including electroporation, use of spheroplasts, lithium acetate, and the like. Any method capable of introducing DNA into animal cells can be used: for example, electroporation, calcium phosphate, lipofection and the like.

Recombinant Enzyme

For preparation of recombinant xylanase, following transformation of a suitable host strain and growth of the host strain to an appropriate cell density, e.g., a bacterial or yeast host, a selected promoter may be induced by appropriate means (e.g., temperature shift or chemical induction) and cells cultured for an additional period to yield recombinant enzyme. Cells are then typically harvested by centrifugation, disrupted by physical or chemical means, and the resulting crude extract retained for further purification. Alternatively, the recombinant protein may be produced as a fusion to a signal peptide that facilitates export of the recombinant protein from the host cell. In this situation, cells are harvested by centrifugation and the supernatant is retained. The recombinant protein may then be purified from the supernatant.

Microbial cells employed in expression of proteins can be disrupted by any convenient method, including freeze-thaw cycling, sonication, mechanical disruption, or use of cell lysing agents, such methods are well known to those skilled in the art.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a product of chemical synthetic procedures, or produced by recombinant techniques from a microbial host (for example, by bacterial, yeast, and fungal cells in culture). Depending upon the host employed in a recombinant production procedure, the enzyme of the present invention may or may not be covalently modified via glycosylation. In eukaryotic cells, glycosylation of secreted proteins serves to modulate protein folding, conformational and thermostability stability, and resistance to proteolysis. Given a specific application of xylanase use, a glycosylated version of the enzyme may be preferable over a non-glycosylated form. For example, the use of a glycosylated xylanase in animal feed helps protect the enzyme from thermal denaturation during feed pelleting and from proteolytic inactivation as it passes through the stomach of the animal, helping deliver active enzyme to the intestinal tract and site of action. For food processing applications where enzyme activity is desired only during processing and not in the final product a non-glycosylated, thermolabile, and proteolytic susceptible xylanase is preferred. By producing the xylanase of this invention in various microbial hosts, both thermotolerance and susceptibility to proteolytic degradation are altered.

The enzymes of this invention may be employed for any purpose in which such enzyme activity is necessary or desired. In a preferred embodiment, the enzyme is employed for catalyzing the hydrolysis of xylan in animal feed. In another preferred embodiment, the enzyme is employed for catalyzing the hydrolysis of xylan in food.

Xylanase Compositions

Generally, xylanase compositions are liquid or dry. Liquid compositions need not contain anything more than the xylanase enzyme, preferably in a highly purified form. However, a stabilizer such as glycerol, sorbitol or mono propylene glycol may be added. The liquid composition may also comprise other additives, such as salts, sugars, preservatives, pH-adjusting agents, and proteins,. Typical liquid compositions are aqueous or oil-based slurries. The liquid compositions may be added to a food or feed before or after an optional pelleting thereof.

Dry compositions may be freeze-dried or spray dried compositions, in which case the composition need not contain anything more than the enzyme in a dry form. Dry compositions may be granulates which may readily be mixed with, e.g., food or feed components, or more preferably, form a component of a pre-mix. The particle size of the enzyme granulates preferably is compatible with that of the other components of the mixture. This provides a safe and convenient means of incorporating enzymes into, e.g., processed food or animal feed.

For example, a stable xylanase enzyme formulation can be prepared by freezing a mixture of liquid enzyme solution with a bulking agent such as ground soybean meal, and then lyophilizing the mixture. The reduction in moisture and the binding interactions of the xylanase with the bulking agent protect the enzyme from external environmental factors such as the temperature extremes experienced during compound feed manufacture. Dry formulations can further enhance stability by minimizing the activity of potential proteolytic enzymes that may be present as by-products in the liquid fermentation mixture used to manufacture the target enzyme. The resulting dry enzyme-soy flour mixture of the present invention can withstand high extremes of temperature. This formulated enzyme mixture can be used as a feed supplement for use in poultry and swine production.

Once a dry enzyme preparation is obtained, agglomeration granulates are prepared using agglomeration techniques in a high shear mixer during which a filler material and the enzyme are co-agglomerated to form granules. Absorption granulates are prepared by having cores of a carrier material to absorb/be coated by the enzyme. Typical filler materials are salts such as disodium sulphate. Other fillers include kaolin, talc, magnesium aluminium silicate and cellulose fibres. Optionally, binders such as dextrins are also included in agglomeration granulates.

Typical carrier materials include starch, e.g., in the form of cassava, corn, potato, rice and wheat. Salts may also be used.

Optionally, the granulates are coated with a coating mixture. Such a mixture comprises coating agents, preferably hydrophobic coating agents, such as hydrogenated palm oil and beef tallow, and if desired, other additives such as calcium carbonate or kaolin.

Additionally, xylanase compositions may contain other substituents such as coloring agents, aroma compounds, stabilizers, vitamins, minerals, other feed or food enhancing enzymes and the like. This is so in particular for the so-called pre-mixes.

A "food or feed additive" is an essentially pure compound or a multi component composition intended for or suitable for being added to food or feed. In particular it is a substance that by its intended use is becoming a component of a food or feed product or affects any characteristics of a food or feed product. Thus, a xylanase additive is understood to mean a xylanase which is not a natural constituent of the main feed or food substances or is not present at its natural concentration therein, e.g., the xylanase is added to the feed separately from the feed substances, alone or in combination with other feed additives. A typical additive usually comprises one or more compounds such as vitamins, minerals or feed enhancing enzymes and suitable carriers and/or excipients.

A "ready for use" xylanase additive is herein defined as an additive that is not produced in situ in animal feed or in processed food. A ready for use xylanase additive may be fed to humans or animals directly or, preferably, directly after mixing with other feed or food constituents. For example, a feed additive according to this aspect of the present invention is combined with other feed components to produce feed. Such other feed components include one or more other (preferably thermostable) enzyme supplements, vitamin feed additives, mineral feed additives and amino acid feed additives. The resulting (combined) feed additive including possibly several different types of compounds can then be mixed in an appropriate amount with the other feed components such as cereal and protein supplements to form an animal feed. Processing of these components into an animal feed can be performed using any of the currently used processing apparatuses such as a double-pelleting machine, a steam pelleter, an expander or an extruder.

Similarly, a food additive according to this aspect of the present invention is combined with other food components to produce processed food products. Such other food components include one or more other (in particular thermostable) enzyme supplements, vitamin food additives and mineral food additives. The resulting (combined) food additive, including possibly several different types of compounds can then be mixed in an appropriate amount with the other food components such as cereal and plant proteins to form a processed food product. Processing of these components into a processed food product can be performed using any of the currently used processing apparatuses.

In another embodiment, the xylanase compositions of the invention additionally comprises an effective amount of one or more feed or food enhancing enzymes, in particular feed or food enhancing enzymes selected from the group consisting of alpha-galactosidases, beta-galactosidases, in particular lactases, other xylanases, beta-glucanases, in particular endo-beta-1,4-glucanases and endo-beta-1,3(4)-glucanases, cellulases, xylosidases, galactanases, in particular arabinogalactan endo-1,4-beta-galactosidases and arabinogalactan endo-1,3-beta-galactosidases, endoglucanases, in particular endo-1,2-beta-glucanase, endo-1,3-alpha-glucanase, and endo-1,3-beta-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-alpha-rhamnosidase, pectate lyases, and alpha-galacturonisidases, mannanases, beta-mannosidases, mannan acetyl esterases, xylan acetyl esterases, proteases, xylanases, arabinoxylanases and lipolytic enzymes such as lipases, phospholipases, phytases and cutinases.

The animal feed additive of the invention is supplemented to the animal before or simultaneously with the diet. Preferably, the animal feed additive of the invention is supplemented to the animal simultaneously with the diet.

An effective amount of xylanase in food or feed is from about 1 to 10,000 U/kg; more particularly from about 50 to 5,000 U/kg, more particularly from about 500 to 4,000 U/kg or from about 250 to 3200 U/kg.

Also within the scope of this invention is the use of xylanase for processing and manufacturing human foods and animal feeds. Grains and flours destined for human foods can be enzymatically treated with xylanase to reduce the xylan content of the material. The reduced levels of xylan enhance the quality of the food by increasing the nutrient availability of essential minerals such as iron, calcium, and zinc. In addition to increasing the nutritional quality of food, xylanase used during food processing can improve the overall efficiency of the food production method. During food manufacture the xylanase is active during manufacture and processing only, and is not active in the final food product. This aspect is relevant for instance in dough making and baking. Similarly, animal feed grains such as toasted soybean meal or canola meal may be pre-processed with xylanase prior to compound feed manufacture. Removal of the anti-nutritive factors in animal feed components prior to compound feed manufacture produces a nutritionally higher quality and more valuable animal feed ingredient. In this processing method the xylanase is active during feed manufacturing, and may or may not be active in the digestive tract of the animal upon ingestion of the treated feed.

In addition to using xylanase as a food processing aid, the scope of this invention encompasses the use of xylanase as a human supplemental digestive aid. Xylanase in tablet form can be ingested at the time of food consumption to deliver active enzyme to the gastrointestinal tract of the recipient. Nutritional gains for the consumer would be experienced in vivo and may be taken with foods that cannot be treated with a xylanase during food processing.

Also within the scope of the invention is the use of a xylanase of the invention during the preparation of food or feed preparations or additives, i.e., the xylanase is active during the manufacture only and is not active in the final food or feed product. This aspect is particularly relevant, for instance, in dough making and baking and the production of other ready-to-eat cereal based products.

The xylanase may also be used advantageously in monogastrics as well as in polygastrics, especially young calves. Diets for fish and crustaceans may also be supplemented with xylanase to further improve feed conversion ratio. The feed according to the present invention may also be provided to animals such as poultry, e.g., turkeys, geese, ducks, as well as swine, equine, bovine, ovine, caprine, canine and feline, as well as fish and crustaceans. It is however, particularly preferred that the feed is provided to pigs or to poultry, including, but not limited to, broiler chickens, hens, in particular laying hens, turkeys and ducks.

Feed Compositions and Methods of Use

The xylanases (formulated as described above) of the current invention may be combined with other ingredients to result in novel feed compositions with particular advantages.

The xylanases of the present invention are so active that they can be used to create novel animal feed formulations that allow superior feed conversion efficiency and improved weight gain relative to normal diets.

Specifically, the animal feed of the invention comprises the combination of a xylanase of the present invention in combination with animal feed ingredients to form a feed that has substantially lowered intact xylan content. In a preferred embodiment, the feed compositions of the invention comprises typical feed ingredients, micronutrients, vitamins, etc. and an effective amount of thermostable xylanase where the amounts of the xylanase is from about between the levels of 1-10,000 units of xylanase per kg of feed; more particularly between the levels of 50-5,000 units of xylanase per kg of feed.

Also, within the scope of the invention are methods of improving weight gains, and feed conversions ratios (FCR) associated with production of farm animals. A xylanase of the present invention allows improved weight gains and FCR. Specifically the method of the present invention is to improve the FCR, or weight gain by feeding a diet to an animal comprising a xylanase of the present invention.

The animal feed of the present invention can be used on monogastric or polygastric animals. The animal feed of the present invention can be feed for poultry, or swine, or calves, or companion animals such as dogs, cats, or horses. The animal feed can also be used on ruminants such as cows.

The invention will be further described by the following examples, which are not intended to limit the scope of the invention in any manner.

EXAMPLE 1

XylA1A Expression Constructs pBSC12771 (pPIC9 harboring the Synthetic XylA1A Xylanse Gene). A synthetic gene encoding the XylA1A xylanase amino acid sequence was constructed at Entelechon (Regensburg, Germany) utilizing *Pichia pastoris* preferred codons and was designated PP6002 (for *Pichia pastoris* optimized codon version of XylA1A) (SEQ ID NO:1). The synthetic gene sequence was designed to include the KEX2 protease cleavage signal (Glu-Lys-Arg) (SEQ ID NO: 37 and nucleotide sequence SEQ ID NO:36) in front of the mature peptide coding sequence. The synthetic gene was supplied in the pPIC9 vector (Invitrogen, Carlsbad, Calif.) and was designated pBSC12771 by Syngenta Quality Control (FIG. 1 and SEQ ID NO:33). This cloning strategy produced a fusion protein in which the *Saccharomyces cerevisiae* α-mating factor pre-pro-peptide secretion signal (nucleotide and amino acid sequences, SEQ ID NOS: 38 and 39, respectively) is fused in frame to the N-terminus of the PP6002 gene sequence. The fusion peptide encoded by this gene is secreted from the cell after production. During the secretion process, the α-factor peptide portion of the fusion protein is cleaved by the Kex2 protease and XylA1A xylanase is released into the extracellular environment.

This facilitates the isolation and purification of XylA1A enzyme. The PP6002 gene in this construct is under the control of the *P. pastoris* alcohol oxidase-1 (AOX1) promoter that is inducible with methanol. The synthetic gene was confirmed by using plasmid specific 5AOX and 3AOX sequencing primers supplied by the manufacturer (Invitrogen, Carlsbad, Calif.). After sequence confirmation, the pBSC12771 plasmid was retransformed into chemically competent *E. coli* TOP10 cells as previously described and a glycerol stock was prepared using methods described by Sambrook J, Russel D W. 2001. "Molecular Cloning: A Laboratory Manual," $3^{rd}$ Ed. (Cold Spring Harbor Press, Cold Spring Harbor, N.Y.).

Construction of pCR4Blunt_5AOX-PP6002-3AOXTT Intermediate. The yeast multi-copy expression vector pAO815 (Invitrogen, Carlsbad, Calif.) was used to make multimers of the PP6002 expression cassette. In order to make the pAO815 multimerization expression vector, a series of intermediate vectors were constructed. The parent vector pBSC12771 was linearized by BamHI digestion. The BamHI restriction site was then backfilled using T4 polymerase (NEB, Beverly, Mass.). The backfilled BamHI site was then ligated upon itself using T4 quick ligase (NEB, Beverly, Mass.). Any remaining, unmodified parent vector was removed by a second BamHI digestion. The BamHI-digested, backfilled, and religated DNA was transformed into chemically-competent *E. coli* TOP10 cells and selected on $LB_{amp100}$ overnight at 37° C. Single isolated colonies were grown in selective media and DNA was purified by methods described by Qiagen (Qiagen mini-prep purification kit, Valencia, Calif.). The elimination of the BamHI site was confirmed by restriction digestion with BamHI. The modified vector was designated pPIC9mod-PP6002 and was used as template for PCR. A GeneAmp® PCR System 9700 thermocycler (Applied Biosystems, Foster City, Calif.) and Advantage cDNA Polymerase (Clontech, Palo Alto, Calif.) were used to amplify the target DNA using the oligos and thermocycling parameters below:

```
Primer1:                              (SEQ ID NO:23)
5'-AGATCTAACATCCAAAGACGAAAGGTTGAATGAAAC-3'

Primer2:                              (SEQ ID NO:24)
5'-CATTAGGATCCGCACAAACGAACGTCTCACTTAATC-3'
```

TABLE 1

Thermocycler parameters

| Step | Temp(C.) | Time | Cycles |
|---|---|---|---|
| 1 | 94 | 5 min | 1 |
| 2 | 94 | 30 sec | 25 |
| 3 | 65 | 30 sec | |
| 4 | 72 | 30 sec | |
| 5 | 72 | 5 min | 1 |
| 6 | 4 | 5 min to about 24 hrs | |

Primers 1 and 2 were designed to amplify from the 5' end of the AOX1 promoter to the 3' end of the AOX1 transcription terminator, including the alpha-secretion factor-xylanase ORF. Also, these primers were designed to incorporate a BglII site on the 5' end of the product and a BamHI site on the 3' end of the product for subsequent multimerization of the expression cassette. The resulting PCR product was cloned directly into the topoisomerase-1 activated vector pCR4Blunt-TOPO by methods described by Invitrogen (Invitrogen, Carlsbad, Calif.). This vector was designated pCR4Blunt_5AOX-PP6002-3AOXTT. SP6, T7 and gene specific sequencing primers confirmed the fidelity of the amplification and cloning.

Construction of pBSC12772 (pAO815_1x PP6002) Expression Vector.

Oligonucleotides (see primers 3 and 4 below) were designed to amplify the ORF containing the *Saccharomyces cerevisiae* α-mating factor and PP6002 from pBSC12771 by PCR. A GeneAmp® PCR System 9700 thermocycler (Applied Biosystems, Foster City, Calif.) and PfuUltra Hotstart Polymerase (Statagene, La Jolla, Calif.) were used to amplify the target DNA.

```
Primer3:                                    (SEQ ID NO:25)
5'-GGGGCCGGGAATTCCGATGAGATTTCCTTCAATTTTT-3'

Primer4:                                    (SEQ ID NO:26)
5'-GCCGGGGAATTCCGCGGCCGCCTATTACCAGACAGTAACATT
TGA-3'
```

The primers incorporated EcoRI sites onto the ends of the PCR product allowing for subsequent insertion of the product into the pAO815 recipient vector. Amplification by thermocycle reactions was performed using the following parameters:

TABLE 2

| Thermocycle parameters | | | |
|---|---|---|---|
| Step | Temp(C.) | Time | Cycles |
| 1 | 94 | 5 min | 1 |
| 2 | 94 | 30 sec | 25 |
| 3 | 65 | 30 sec | |
| 4 | 72 | 1 min | |
| 5 | 72 | 7 min | 1 |
| 6 | 4 | 5 min to about 24 hrs | |

Figure 2:
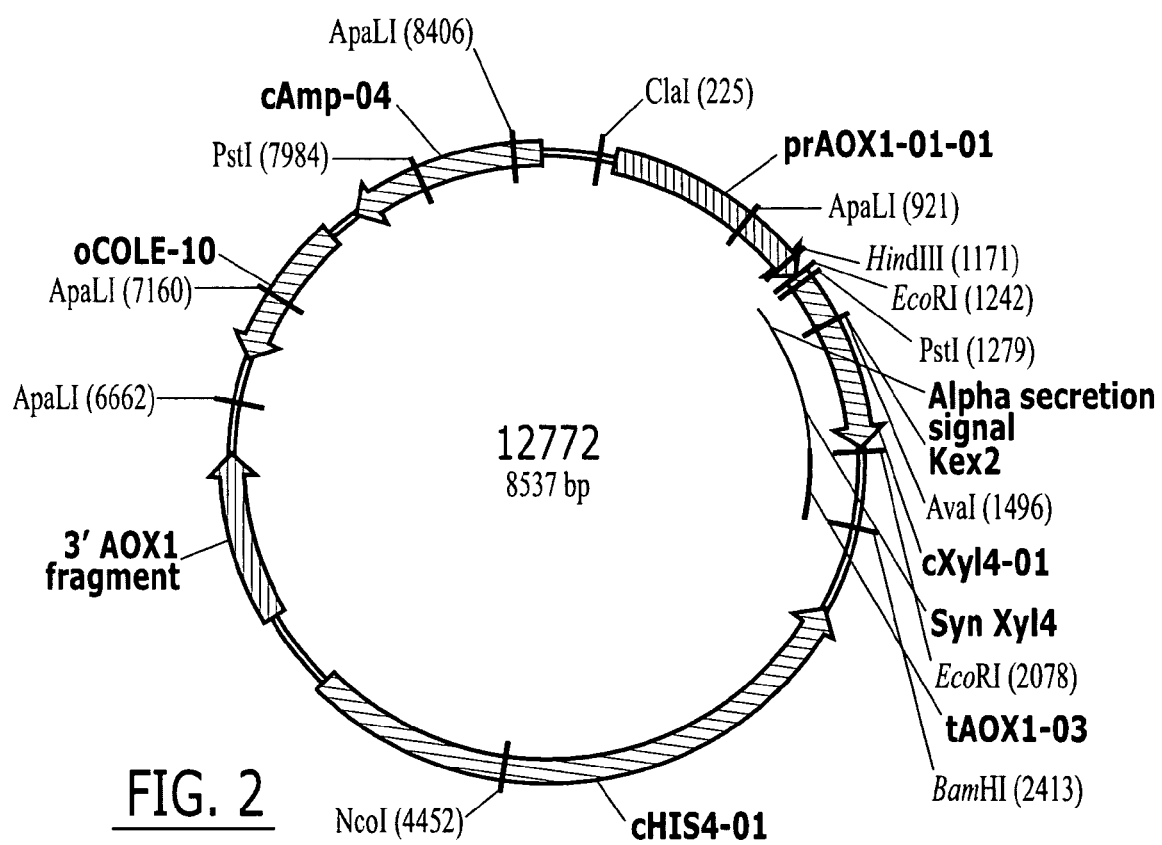
FIG. 2 is the vector map of plasmid pBCS12772.

The PCR product was digested with EcoRI. The restriction reaction was separated by electrophoresis through a 0.8% TAE gel and a 0.8 kb fragment was gel purified by methods described by Qiagen (Qiaquick Gel extraction Kit; Qiagen, Valencia, Calif.). In a parallel restriction digest reaction, the 7.7 kb *Pichia pastoris* multicopy expression vector pAO815 (Invitrogen; Carlsbad, Calif.) was digested with EcoRI and its cohesive ends were dephosphorylated by calf intestine phosphatase treatment (New England Biolabs, Berverly, Mass.). The vector fragment was separated by electrophresis through a 0.8% TAE gel and gel purified as above. The EcoRI-digested and gel-purified PCR fragment was ligated directly into the linearized, dephosphorylated pAO815 using T4 DNA ligase (Quick Ligation Kit, New England Biolabs; Beverly, Mass.). The ligation reaction was transformed into chemically competent *E. coli* TOP10 cells and spread onto LB plates containing ampicillin (100 □g/mL). Single isolated colonies were grown in the selective media and DNA was purified by methods described by Qiagen (Qiagen mini-prep purification kit, Valencia, Calif.). The gene orientation and sequence were confirmed using plasmid specific 5AOX and 3AOX sequencing primers supplied by the manufacturer (Invitrogen, Carlsbad, Calif.). After sequence confirmation, the pAO815_1x PP6002 plasmid was retransformed into chemically competent *E. coli* TOP10 cells and a glycerol stock was prepared using methods described by Sambrook, et al. 2001. The pAO815_1x PP6002 construct was submitted to Syngenta Biotechnology, Inc. Quality Control and was designated pBSC12772 (See FIG. 2 and SEQ ID NO:34).

Multimerization of the PP6002 Expression Cassette. The expression cassette (5AOX-PP6002-3AOXTT) was removed from pCR4Blunt_5AOX-PP6002-3AOXTT by double-digestion with BglII and BamHI (New England Biolabs; Beverly, Mass.) and the 2.1 kb fragment was gel purified. In a separate reaction, the pBSC12772 was digested with BamHI and its cohesive ends dephosphorylated by CIP treatment as previously described. The BamHI-digested, CIP-treated pBSC12772 was electrophoresed through a 0.8% TAE gel and gel purified. The gel purifed BamHI-BglII expression fragment was ligated into the BamHI-linearized, CIP-treated pBSC12772 vector using T4 DNA ligase (Quick Ligation Kit, New England Biolabs; Beverly, Mass.) and transformed into chemically competent *E. coli* TOP10 cells (Invitrogen; Carlsbad, Calif.). The transformed cells were spread onto LB plates containing ampicillin (100 μg/mL) and the plates incubated at 37° C. overnight. Single isolated colonies were grown in selective media and DNA was prepared by methods described by Qiagen (Valencia, Calif.). The two copy xylanase construct was confirmed by restriction analysis and DNA sequence analysis at the junctions using vector specific primers. The resulting pAO815 vector containing two copies of PP6002 was designated pAO815_2x PP6002.

Figure 3:
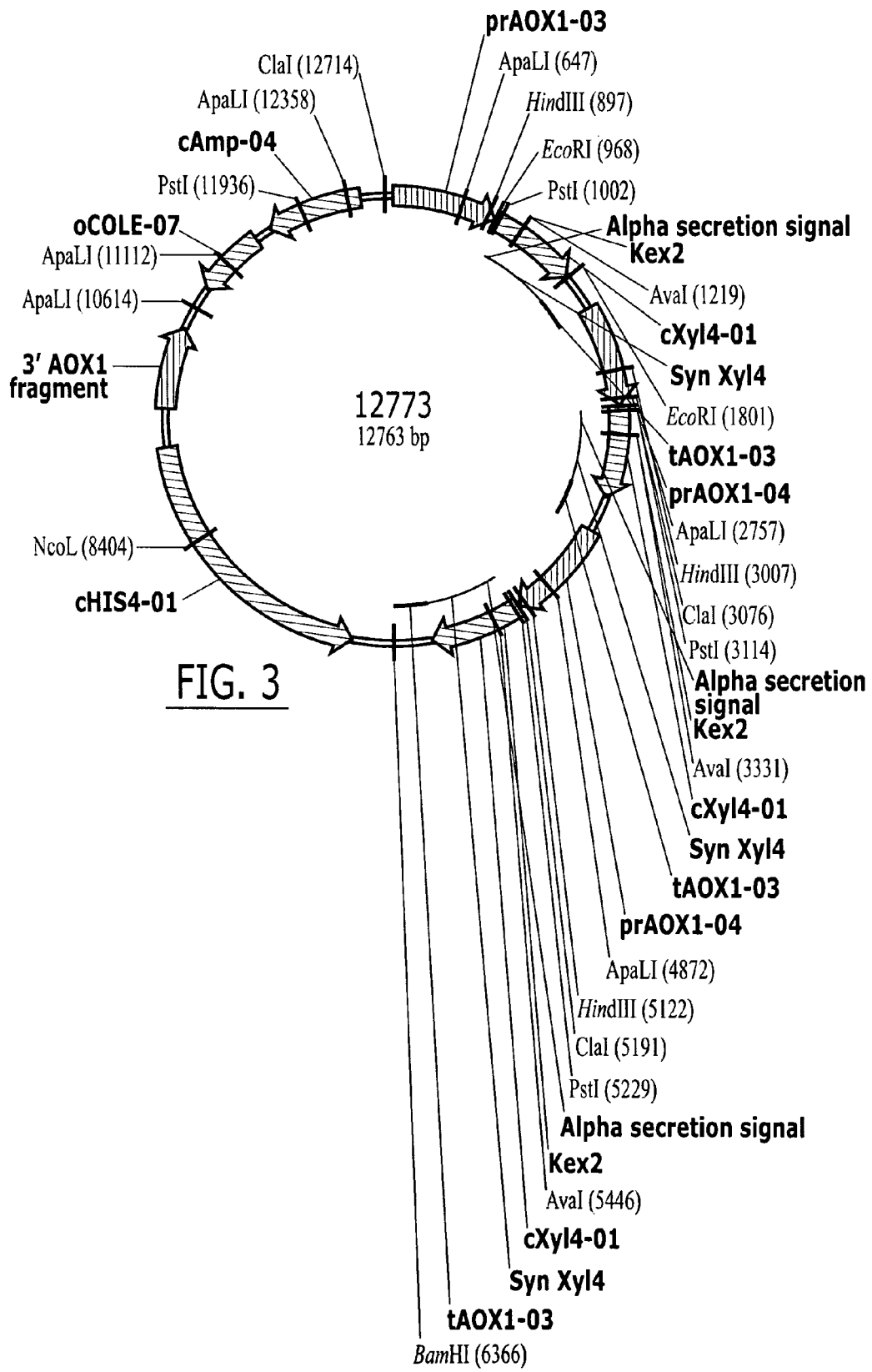
FIG. 3 is the vector map of plasmid pSYN12773.
Figure 4:
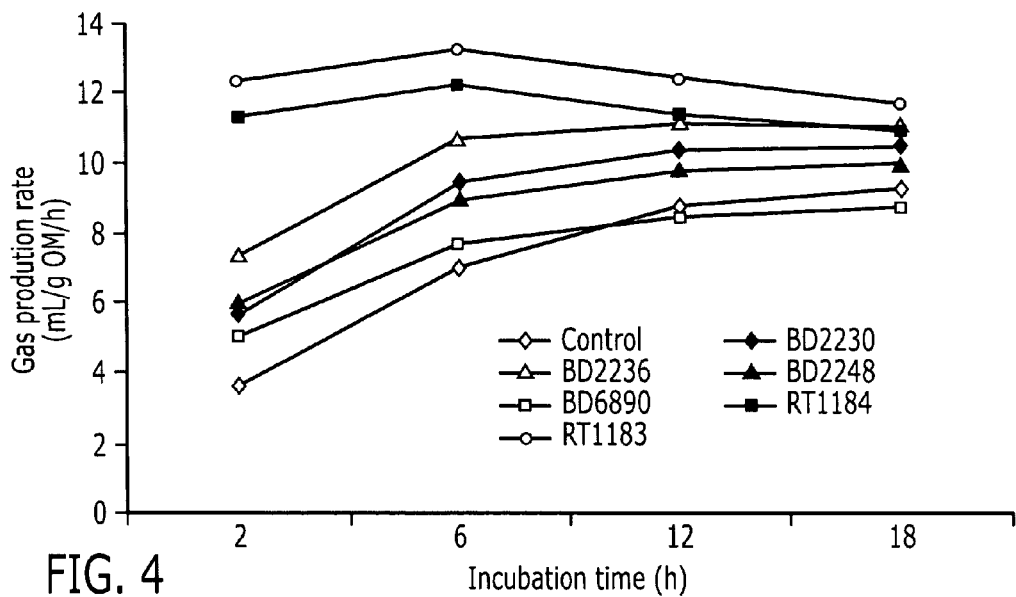
FIG. 4 is a graph of gas production rate for selected xylanase enzymes for 18 h of fermentation. Each point represents the mean of 6 observations.

Construction of pSYN12773 (pAO815_3x PP6002). A construct containing three copies of the synthetic XylA1A expression cassette was constructed by digesting pAO815_2x PP6002 with BamHI and CIP treating the cohesive ends. The purified expression cassette fragment from the BamHI-BglII double digest reaction pCR4Blunt_5AOX-PP6002-3AOXTT was ligated into the BamHI-digested, CIP-treated pAO815_2x PP6002 vector using T4 DNA ligase (Quick Ligation Kit, New England Biolabs; Beverly, Mass.) and subsequently transformed into chemically competent *E. coli* TOP10 cells as previously described. The transformed cells were spread onto LB plates containing ampicillin (100 μg/mL) and the plates incubated at 37° C. overnight. Single isolated colonies were grown in selective media and DNA was prepared by methods described by Qiagen (Valencia, Calif.). The 3x copy expression construct was confirmed by restriction fragment analysis. Furthermore, the complete nucleotide sequence of pAO815_3x PP6002 was confirmed by Syngenta Biotechnology Inc. Quality Control. The pAO815_3x PP6002 construct was designated pSYN12773 (see FIG. 3 and SEQ ID NO:35) by Syngenta QC.

EXAMPLE 2

Preparation of pSYN12773 DNA for Transformation of *P. pastoris*. A 50 mL culture of TB broth supplemented with ampicillin (100 μg/mL) was inoculated with the glycerol stock of *E. coli* TOP10 cells harboring pSYN12773, and grown over-night at 37° C. DNA was purified from the culture by methods described by Qiagen (Qiaprep Midiprep protocol, Qiagen, Valencia, Calif.). The isolated plasmid DNA was digested over-night with BglII endonuclease (New England Biolabs, Beverly, Mass.). The digestion mix was electrophoresed through a 0.8% Tris Acetate EDTA (TAE) agarose gel and the 10.4 kb fragment corresponding to the XylA1A integration cassette purified from the gel by methods described by Qiagen (QiaQuick gel purification protocol, Valencia, Calif.). A portion of the purified fragment was electrophoresed through a 0.8% TAE gel to confirm complete digestion and its relative concentration. In addition, a portion of the purified fragment was transformed into chemically competent *E. coli* DH5α cells to confirm that no residual circularized plasmid harboring the ampicillin marker contaminated in the sample. The entire transformation mix was spread on an LB$_{Amp100}$ plate and incubated at 37° C. for 16 hours. No colonies grew on the plate.

EXAMPLE 3

Construction of P. pastoris XylA1A Expression Host

Preparation of P. pastoris GS115 Cells for Transformation. All microbiological manipulations were conducted in a laminar flow hood using aseptic techniques. Pichia pastoris GS115 yeast cells (Invitrogen, Carlsbad, Calif.) were prepared by streaking the cells onto YPD agarose plates. Following overnight growth at 30 □C, a single yeast colony from the YPD agarose plate was transferred to 5 ml of YPD broth and grown at 30° C. overnight. A portion of this "seed culture" was used to inoculate a sterile 2-liter, baffeled flask containing 500 mL of YPD broth. This culture was grown with vigorous shaking overnight at 30° C. to an optical density OD$_{600}$=1.5. The cells were harvested by centrifugation at 4000 Xg, 4° C., 5 minutes, and resuspended in 80 mL of sterile double distilled (sdd) water. Ten milliliters of 10× TE buffer (10 mM Tris-HCl, 0.1 mM EDTA), pH 7.5 was added to the suspension followed by 10 mL of 1M lithium acetate (LiAc). The cell suspension was incubated at 30° C. with gentle swirling. After 45 minutes of incubation, 2.5 mL of 1 M dithiothreitol (DTT) was added and the cell suspension returned to incubate at 30° C. for an additional 15 minutes. The cells were then washed in a series of water washes and finally resuspended in 5 mL of ice-cold 1 M sorbitol.

Transformation of pSYN12773 DNA into Pichia pastoris GS115. Purified DNA (100 ng) of the XylA1A expression cassette from the BglII digested pSYN12773 plasmid was mixed with 80 μL of LiAc/sorbitol-treated Pichia pastoris GS115 cells in a 0.2 cm electroporation cuvette (Gene Pulser Cuvettes, BioRad, Hercules, Calif.) and incubated on ice for 5 minutes. The electroporation cuvette was placed into a BioRad Gene Pulser II instrument and pulsed using settings of 1.5 kV, 25 μF, and 200Ω Ice-cold sorbitol (0.5 mL) was added to the electroporation mix which was then plated onto histidine deficient, minimal media-dextrose (MD) agar plates. P. pastoris strain GS115 is a histidine auxotroph and is unable to grow in the absence of histidine, but stable transformants containing the his4 gene on the XylA1A expression cassette are restored to histidine prototrophy and are capable of growth on histidine-free media. Growth at 30° C. for 3 days produced a number of histidine prototrophic transformants. LiAc/Sorbitol washed GS115 cells electroporated in the absence of transforming DNA were plated onto MD and MD/histidine agar plates as controls. The GS115 cells with no transforming DNA present during electroporation generated no colonies capable of growth on MD plates lacking histidine.

Identification of P. pastoris Transformants Producing Xylanase. From the primary transformants on MD plates, 256 single, his$^+$ prototrophic, isolated colonies were picked and replica plated onto a MD master plate. These colonies were subsequently replica-plated to histidine-deficient, minimal-media with 1.0% methanol (MM) agar plates containing 0.1% Azo-wheat arabinoxylan (abbrev. AzoWAXY; Megazyme, County Wicklow, Ireland). After 16 hours incubation at 30 □C, clearing zones surrounding colonies on the MM AzoWAXY plate identified 92 transformants producing xylanase activity. Twenty-four (24) of the 92 xylanase expressing clones were inoculated into 3 mL of BMMY induction broth contained in a 24 position, deep-well block and the clones expressed for 5 days. After induction, the supernatants were analyzed by xylanase activity assay and ELISA. Eight (8) transformants produced xylanase at levels putatively higher than yields of the controls. The expression levels for these 8 transformants were further investigated in 50 mL shake flasks. Following 5 days of induction, events 5501, 5517, and 5520 gave statistically significant improvements in yield and productivity.

Preparation of Glycerol Stocks for Long-Term Storage of P. pastoris Harboring pSYN12273 Transformants. Glycerol freezer stocks were prepared by inoculating 7 mL of sterile liquid MD media in a capped 16×150 mm glass tube with each of the 8 putative high-expressing xylanase positive clone from the MD master plate. These were grown overnight at 30° C. on a rotating culture wheel. One milliliter (1 mL) of sterile glycerol was mixed into each culture to yield a 15% (v/v) mixture of glyercol to culture. Each culture was aliquoted into a sterile cryo-vials and stored at −80° C.

Characterization of XylA1A P. pastoris Expression Host

Screening for MutS Phenotype. In order to identify the MutS clones, the xylanase-positive clones were streaked onto histidine-deficient, minimal-media containing 1.0% methanol (MM) agar plates along side a MutS positive control (GS115 harboring pPIC9-secHSA; Invitrogen, Carlsbad, Calif.) and a Mut+ control (GS115 harboring pPIC3-βGal; Invitrogen, Carlsbad, Calif.). The plates were incubated at 30° C. for 4 days and the growth on MM recorded. Thirty-nine (39) of the original 92 his$^+$ xyn$^+$ events identified previously exhibited slow growth on MM media comparable to the controls. Of these thirty nine events, eight had previously been identified as high expressors by activity and ELISA.

Preliminary Hybridization Screen for the XylA1A Expression Cassette. A series of hybridization experiments were conducted. In the preliminary hybridization screen, genomic DNA was prepared using standard techniques (Miles J D, Busser K, Stalder C, and Higgins D R (1998) Isolation of nucleic acids, in Pichia Protocols, vol. 103 (Higgins D R & Cregg J M, eds.), Humana Press, Totowa, N.J., pp. 73-80) for the eight putative high-expressing events. Two micrograms of genomic DNA was digested using BglII restriction endonuclease. The digests were run through a 0.8% agarose gel then transferred bi-directionally onto two nitrocellulose membranes generating duplicate blots. DNA hybridization probes specific for PP6002 CDS PP6002 and the ampicillin gene (cAmp-04) were prepared. The xylanase and amp probes were generated by polymerase chain reaction using gene specific primers (see primers 5 and 6 for PP6002 and primers 7 and 8 for amp).

```
Primer5:
5'-GCATCTACTGACTACTGGCAG-3'       (SEQ ID NO:27)

Primer6:
5'-CCAGACAGTAACATTTGAATAACC-3'    (SEQ ID NO:28)

Primer7:
5'-GGGCGACACGGAAATGTTGAATACTCAT-3' (SEQ ID NO:29)

Primer8:
5'-TTACCAATGCTTAATCAGTGAGGCACC-3'  (SEQ ID NO:30)
```

The products were gel purified and radiolabelled with [$^{32}$P]-dCTP using the Rediprime-II labeling system (Amersham Biosciences, Piscataway, N.J.). Following stringent hybridization with the [$^{32}$P]dCTP-amp probe in hybridization buffer at 65 □C, the first blot did not show any hybridizing bands, with the exception of the positive control, BglII digested pSYN12773. This experiment indicated that the ampicillin gene did not integrate into the genome of P. pastoris in any of these events. The duplicate blot was probed with [$^{32}$P]dCTP- PP6002 using the high stringency methods previously described and produced a single band of approximately 10.4 kb for events 5517 and 5520, indicating that three copies of the xylanase gene had successfully integrated into these events.

Detailed Hybridization Screen for Event 5520. In support of the preliminary hybridization screen, additional restriction digestions of the event 5520 genomic DNA were performed. Two micrograms of event 5520 genomic DNA were digested with BamHI, BglII, EcoRI×NotI PstI, PvuII, and XhoI×NotI restriction endonucleases. The digests were run through a 0.8% agarose gel then transferred bi-directionally onto two nitrocellulose membranes generating duplicate blots. DNA hybridization probes specific for the cXyl4-01 CDS αss-PP6002 and the vector backbone genes (cAmp-04 and oCOLE-10) were prepared. The xylanase and backbone probes were generated by polymerase chain reaction using gene specific primers (primers 3 and 6 for cXyl4-01 and primers 9 and 10 below for backbone).

```
Primer9:
5'-GCTGCCTCGCGCGTTTCGGTGATGA-3'    (SEQ ID NO:31)

Primer10:
5'-GGGAACACTGAAAAATAACAGTTAT-3'    (SEQ ID NO:32)
```

The products were gel purified and radiolabelled with [$^{32}$P]-dCTP using the Rediprime-II labeling system (Amersham Biosciences, Piscataway, N.J.). Following stringent hybridization with the [$^{32}$P]dCTP-Backbone probe in PerfectHyb™ Plus hybridization buffer (Sigma Chemical Co., St. Louis Mo.) at 65° C., the first blot did not show any hybridizing bands, with the exception of the positive control, BglII digested pSYN12773. This experiment indicated that the vector backbone did not integrate into the genome of P. pastoris in event 5520. The duplicate blot was probed with [$^{32}$P] dCTP-cXyl4-01 using the high stringency methods previously described and produced a single band of approximately 10.4 kb in the BglII digested sample, indicating that three copies of the xylanase gene had successfully integrated into event 5520. The BamHI, EcoRI×NotI, PstI, PvuII and XhoI× NotI digested samples produced bands with the expected migration profile for integration at the AOX1 locus of P. pastoris. In summary, all characterizations of P. pastoris PP6002 expression event 5520 by Southern blotting and growth characteristics on methanol containing minimal media demonstrates that the event has a His$^+$, Mut$^S$ phenotype, contains three copies of the PP6002 expression cassette inserted into the AOX1 locus, and does not contain the ampicillin resistance gene or other components of the vector backbone.

EXAMPLE 4

Preparation of the PP6002 P. pastoris Master Cell Bank

From the MD glycerol freezer stock of event 5520, a master cell bank was made; hereafter named SYN12773. Under aseptic conditions, a sample from the SYN12773 glycerol freezer stock was revived by streaking onto a MD plate and incubated at 30° C. until the appearance of colonies. A single colony was picked from the MD plate and inoculated into a culture tube containing 5 mL of MD liquid media. The tube was incubated over night on a rotating wheel at 30° C. The following day, the SYN12773 starter culture was inoculated into a 2.8 L baffled flask containing 350 mL of YPD medium. The culture was grown at 30 □C on a shaker at 250 rpm until an OD$_{600}$=2.0-3.0, 3.0×10$^7$ cells was reached. Under aseptic conditions, 150 mL of sterile glycerol was added to the 350 mL of YPD culture resulting in a 30% (v/v) ratio of glycerol to YPD. Aliquots (1.0 mL) of culture were transferred to 243 sterile 2.0 mL polypropylene cryogenic tubes with screw caps and 0-ring seal attachments (Fisher Science, Cat No. 056698). The 243 cryo-vials were placed into 3 cryo-boxes and stored at −80° C.

Purity of the P. pastoris Xylanase Master Cell Bank. A one microliter sample from one of the vials in the master cell bank was streaked onto a YPD agar plate. The plate was incubated overnight at 30° C. to generate individual colonies. These colonies were examined visually and were found to have a homogenous colony morphology that was identical to that of the parent strain P. pastoris GS115. A single colony from the YPD plate was streaked to a MD and a MM AzoWAXY agar plate and grown at 30 □C until the appearance of single colonies. The resulting colonies were able to grow on both MD and MM agar that lack histidine, indicating that like event SYN12773, but unlike the parent strain GS115, they all had a His$^+$ phenotype. Furthermore, all colonies grew slowly on MM agar containing methanol as a source of carbon, indicating that like event SYN12773, but unlike strain GS115, they have a Muts phenotype that is expected of AOX1 mutants. Additionally, all colonies on the MM AzoWAXY plate produced clearing zones indicating expression of active xylanase. The results of these analyses indicate that the MCB described herein is pure and uncontaminated with other microbes.

Genetic stability of P. pastoris xylanase clone. The genetic stability of the multicopy PP6002 expression cassette in event SYN12773 was tested by conducting 20 consecutive plating experiments on MD agar. Cells from one of the MCB cryogenic vials were revived by streaking onto a MD agar plate and grown up for 48 hours at 30° C. (plate 1). From plate 1, a single colony was picked and replated onto a second MD plate. This cycle of single colony picking and replating was conducted 20 consecutive times. Genomic DNA was purified from a single colony from plates 1 and 20, and used for Southern analysis. The hybridization profiles were compared between the generations 1 and 20. Southern analysis was performed as previously described and no differences were observed between generations 1 and 20. Liquid cultures were prepared from single colonies of plates 1 and 20 for protein expression analysis. Three individual colonies from each of these plates were used to inoculate 50 mL of BMGY media. Cells were grown up overnight at 30° C., spun down and resuspended in 50 mL of BMMY. Cultures were incubated at 30° C. for 5 days with the addition of methanol (MeOH) every day to a final concentration of 1.0% (v/v). At the end of the fermentation period, clarified supernatant was analyzed for xylanase activity.

Clones from both plates produced active xylanase at statistically indistinguishable levels (p<0.05) among cultures from same plate as well as between cultures from plates 1 and 20. Analyses of genomic DNA by Southern analysis and by protein expression for cells from plates 1 and 20 demonstrate the stability of the integrated PP6002 expression cassette in the genome of Pichia pastoris GS115 and expression of the xylanase gene within it.

EXAMPLE 5

Determination of the Xylanase Activity

Enzymatic activity was determined using wheat arabinoxylan as substrate and measuring the release of reducing ends by reaction of the reducing ends with either 3,5-dinitrosalicylic acid (DNS) or 2,2'-bicinchoninic acid (BCA). The substrate was prepared as a 1.4% w/w solution of wheat arabinoxylan (Megazyme P-WAXYM) in 100 mM sodium acetate buffer pH5.30 containing 0.02% sodium azide. The DNS reagent consisted of 0.5% w/w, 15% sodium potassium tartrate, and 1.6% w/w sodium hydroxide. This solution was stable and was stored for up to 3 months at room temperature. The BCA reagent was prepared by combining 50 parts reagent A with 1 part reagent B (reagents A and B were from Pierce, product numbers 23223 and 23224, respectively). These reagents were combined no more than four hours before use.

In the DNS assay, 500 microliters of substrate were combined with 200 microliters of enzyme sample. After incubation at the desired temperature for the desired length of time, 700 microliters of DNS reagent was added. The contents were mixed and placed at 100° C. for 10 minutes. The contents were allowed to cool and then transferred to cuvettes and the absorbance at 540 nm was measured relative to known concentrations of xylose. The choice of enzyme dilution, incubation time, and incubation temperature could be varied by one skilled in the art.

In the BCA assay, 200 microliters of substrate were combined with 80 microliters of enzyme sample. After incubation at the desired temperature for the desired length of time, 2.80 milliliters of BCA reagent was added. The contents were mixed and placed at 80° C. for 35 minutes. The contents were allowed to cool and then transferred to cuvettes and the absorbance at 560 nm was measured relative to known concentrations of xylose. The choice of enzyme dilution, incubation time, and incubation temperature could be varied by one skilled in the art. Enzymatic activity was determined in accordance with the procedure of Miller G. L. (1959) *Anal. Chem.* 31 426-428.

EXAMPLE 6

Trials with Chickens

Standard poultry diets were used containing wheat, rye and soybean meal as the main ingredients. An exemplary diet is set forth in Table 3 XylA1A xylanase, produced in recombinant *P. pastoris* was used. Six (6) replicate pens of 6 chickens for each diet were grown until 21 days of age, and final weights determined by subtracting the weight of the one-day-old chicks. Records were kept of the amount of feed consumed by each pen of chickens, and an average feed consumption was determined. The XylA1A xylanase was formulated by lyophilising the active enzyme preparation then reconstituting with water at the trial site. This formulation was added directly to the diets. Avizyme 1300 was used according to as a commercial standard at similar dosages as the XylA1A xylanase.

TABLE 3

| 3.2 Diet formulation | |
| --- | --- |
| Ingredient | Starter |
| Rye | 20.00% |
| Wheat - Feed | 37.49% |
| Soybean meal 48 | 33.65% |
| Soy oil | 5.31% |
| Salt | 0.39% |
| DL Methionine | 0.22% |
| Lysine HCl | 0.04% |
| Limestone | 1.13% |

TABLE 3-continued

| 3.2 Diet formulation | |
| --- | --- |
| Ingredient | Starter |
| Dicalcium Phos | 1.28% |
| VIT/MIN | 0.49% |
| Crude protein % | 22.88 |
| Poult ME kcal/kg | 3,000.00 |
| Pig DE Kcal | 3,487.48 |
| Calcium % | 0.85 |
| Phos % | 0.67 |
| Avail Phos % | 0.40 |
| Fat % | 6.46 |
| Fibre % | 2.52 |
| Met % | 0.56 |
| Cys % | 0.39 |
| Me + Cys % | 0.95 |
| Lys % | 1.25 |
| His % | 0.56 |
| Tryp % | 0.28 |
| Thr % | 0.84 |
| Arg % | 1.52 |
| Iso % | 0.95 |
| Leu % | 1.69 |
| Phe % | 1.07 |
| Tyr % | 0.75 |
| Val % | 1.05 |
| Gly % | 0.93 |
| Ser % | 1.07 |
| Phe + Tyr % | 1.82 |
| Na % | 0.18 |
| Cl % | 0.29 |
| K % | 0.96 |
| Linoleic acid % | 2.54 |
| Na + K—Cl | 241.72 |
| DUA | 396.57 |
| Sulphur % | 0.22 |
| Magnesium | 0.16 |
| Betaine | 0.47 |
| Choline | 1,378.97 |
| Poult ME MJ/kg | 12.55 |
| Total soya | 0.34 |

Table 4 illustrates the effect of dietary inclusion of XylA1A xylanase on poultry growth performance, represented by feed conversion ratios (FCR). Feed conversion ratio (FCR) refers to the amount of feed consumed divided by the net weight gain of the chicken. A lower ratio indicates that a chicken gained more weight per unit of feed consumed. A lower ratio indicates that a chicken more efficiently utilized the feed that was consumed.

The control diets (with no enzyme supplementation) clearly showed poorer perfomance than addition of even the lowest dose of either enzyme. FCR of the control improved in concert with each incremental dose of enzyme, from 1.671 to an optimum of 1,449 at an inclusion rate of 400 units of XylA1A xylanase. Whilst both xylanases improved performance as dosage increased, it is clear that the XylA1A xylanase was superior to that of Avizyme 1300 as shown by the significant enzyme statistical term. Thus, the use of this XylA1A Xylanase of the invention to supplement such feeds reduces the amount of feed required to produce each unit of weight of broiler chicken compared with the unsupplemented diet and diets containing the commercial standard.

TABLE 4

Data from Feeding Studies of chickens

| | Dose | Intake | Gain | FCR | FCRc | Mortality |
|---|---|---|---|---|---|---|
| Enzyme | | | | | | |
| None | 0 | 1088 | 653 | 1.671 | 1.648 | 4.46 |
| Az 1310 | 50 | 1125 | 716 | 1.571 | 1.541 | 2.38 |
| Az 1310 | 100 | 1079 | 710 | 1.521 | 1.521 | 0.00 |
| Az 1310 | 200 | 1068 | 682 | 1.570 | 1.570 | 0.00 |
| Az 1310 | 400 | 1079 | 699 | 1.544 | 1.544 | 0.00 |
| Az 1310 | 800 | 1069 | 690 | 1.552 | 1.552 | 0.00 |
| Az 1310 | 1600 | 1104 | 709 | 1.558 | 1.535 | 2.38 |
| 6002 | 50 | 1063 | 712 | 1.493 | 1.493 | 0.00 |
| 6002 | 100 | 1097 | 733 | 1.497 | 1.497 | 0.00 |
| 6002 | 200 | 1097 | 707 | 1.554 | 1.545 | 2.38 |
| 6002 | 400 | 1074 | 741 | 1.449 | 1.449 | 0.00 |
| 6002 | 800 | 1072 | 730 | 1.469 | 1.469 | 0.00 |
| 6002 | 1600 | 1097 | 753 | 1.457 | 1.457 | 0.00 |
| | 0 | 1088 | 653 | 1.671 | 1.648 | 4.46 |
| | 50 | 1094 | 714 | 1.532 | 1.517 | 1.19 |
| | 100 | 1088 | 722 | 1.509 | 1.509 | 0.00 |
| | 200 | 1083 | 694 | 1.562 | 1.558 | 1.19 |
| | 400 | 1077 | 720 | 1.497 | 1.497 | 0.00 |
| | 800 | 1070 | 710 | 1.510 | 1.510 | 0.00 |
| | 1600 | 1101 | 731 | 1.508 | 1.496 | 1.19 |
| Az 1310 | | 1087 | 694 | 1.569 | 1.559 | 1.32 |
| 6002 | | 1084 | 718 | 1.513 | 1.508 | 0.98 |
| Statistical p values | | | | | | |
| Enzyme | | 0.7119 | 0.0001 | 0.0001 | 0.0001 | 0.6801 |
| Dose | | 0.6719 | 0.0000 | 0.0000 | 0.0000 | 0.0627 |
| Enz*Dose | | 0.2444 | 0.1804 | 0.2595 | 0.3358 | 0.7516 |
| R-Square | | 0.1495 | 0.5615 | 0.5702 | 0.5577 | 0.1886 |
| RMSE | | 42.99 | 27.86 | 0.06277 | 0.05728 | 3.73 |

EXAMPLE 7

Thermostability of Xylanase Enzyme Produced in Different Hosts

The xylanase protein, BD6002 (also called XylA1A, SEQ ID NO: 14), was expressed in the hosts *Escherichia coli*, *Pichia pastoris*, *Saccharomyces cerevisiae*, and *Pseudomonas fluorescens*. Purified enzyme was obtained and residual activity at 85° C. was measured to determine if there was a difference in thermostability of the xylanase due to expression in different hosts. These hosts differ in the ability to glycosyate the proteins expressed.

Residual Xylanase Assay

This assay procedure is specific for endo-1,4-beta-D-xylanase activity. On incubation of Azo-Wheat Arabinoxylan with endo-xylanase, the substrate is depolymerised by an endo-mechanism to produce low-molecular weight dyed fragments, which remain in solution on addition of industrial methylated spirits (IMS) or 95% ethanol to the reaction mixture. High molecular-weight material is removed by centrifugation, and the color of the supernatant is measured. Endo-Xylanase in the assay solution is determined by reference to a Standard Curve. Each enzyme has its own Standard Curve. The same enzyme produced in different hosts will have different Standard Curves.

Solutions

A. 0.1M Citric Acid.

Dissolve 21.02 g citric acid monohydrate (EM Sciences CX1725-1) in 900 mL demineralized water in glass beaker with stirring. Transfer solution to 1 L volumetric flask and make to 1 L with demineralized water. Filter sterilize and store at room temperature.

B. 0.2M Sodium Phosphate, Dibasic

Dissolve 53.6 g sodium phosphate dibasic heptahydrate (Sigma S9390) in 900 mL demineralized water in glass beaker with stirring. Transfer solution to 1 L volumetric flask and make to 1 L with demineralized water. Filter sterilize and store at room temperature.

C. 50 mM Citrate Phosphate Buffer pH 5.4 (abbrev 50CPB54)

Combine 22.2 mL 0.1M citric acid (§3.A.) with 27.8 mL 0.2M sodium phosphate in 100 mL volumetric flask. Make volume to 100 mL with demineralized water.

D. 1% w/v Wheat Arabinoxylan in 50 mM Citrate Phosphate Buffer pH 5.4

Add 90 ml of 50CPB54 buffer in a 200 ml beaker with stir bar. Cover beaker with aluminum foil. The beaker and contents are placed on a hot-plate stirrer and the water is brought to a boil with vigorous stirring. The aluminum foil is carefully removed, powdered substrate (1.000 g) is added, and the aluminum foil is replaced. The solution is allowed to stir for 10 min while boiling and the heat is turned off. The solution is stirred until it has cooled to room temperature, no clumps of substrate should be observed. The solution is transferred to a 100 mL volumetric flask with stopper. Sodium azide (2% w/v, 1 ml) is added to the volumetric flask. The sides of the beaker are twice washed with a small amount (3-4 ml) of 50CPB54 to remove residual substrate. The washes are combined with the contents in the volumetric flask. The volume is adjusted to 100 ml with 50CPB54 and stopper is inserted. The flask is shaken vigorously. This substrate solution should be stored the solution at 4° C. between uses. Under these conditions and excluding contamination, the substrate is stable for at least several months.

Assay
A. Place 16×100 mm glass tubes in rack in 37° C. water bath.
B. Add 500 uL of 1% w/v WAXY to each tube and equilibrate to 37° C. for at least 5 minutes.
C. Place 600 μL+sample at appropriate dilution in 1.5 mL eppendorf tube and place in 37° C. water bath for at least 5 minutes.
   Typically, it is desirable to target ~0.1 U/mL following dilution to give a signal within the linear range for this assay.
D. Initiate reaction by adding 500 uL sample to substrate in glass tubes. Vortex immediately and start timer.
E. Incubate for exactly 10 minutes at 37° C.
F. Add 2.5 mL 95% ethanol with repeat pipettor and vortex immediately. Transfer tube to rack at room temperature.
G. Let stand 10 minutes at room temperature then vortex again.
H. Centrifuge 10 minutes at 1,000 g, 22° C. in Eppendorf 5810R with acceleration and brake at maximal speed.
I. Remove supernatant to 1.5 mL polystyrene cuvettes.
J. Measure absorbance at 590 nm.

The results from the assays on residual activity of xylanase BD6002 are set forth in Table 5. The results show that the xylanase BD6002 expressed in *Pichia pastoris* had the greatest amount of residual activity after 30 minutes at 85° C. The difference in thermotolerance is expected to be due to difference in the glycosylation of the protein expressed in different host organisms. It is known that prokaryotic hosts, such as *E. coli* and *Pseudomonas* strains do not glycosylate proteins.

TABLE 5

Residual Activity at 85° C. of BD6002 Produced in Different Hosts

| Time | E. coli | P. pastoris | S. cerevisiae | P. fluorescens |
|---|---|---|---|---|
| 0 | 100.0 | 100.0 | 100.0 | 100.0 |
| 5 | 9.1 | 70.9 | 43.8 | 6.5 |
| 10 | 2.4 | 59.3 | 26.3 | 4.3 |
| 15 | 0.8 | 43.0 | 14.4 | 1.9 |
| 20 | 0.1 | 36.6 | 7.3 | 1.4 |
| 25 | 0.5 | 30.7 | 5.7 | 1.4 |
| 30 | 0.3 | 26.7 | 4.0 | 1.0 |

EXAMPLE 8

Effects of Xylanase Enzyme Addition on the Cumulative Gas Production in Ruminal Fluid This example illustrates the difference of additional xylanase enzymes added to ruminant feed as measured by the difference in the gas production when incubated with ruminal fluid.

The objective of this experiment is to assess the effect of xylanase supplementation on ruminal degradation with alfalfa hay. Based on the results of endoglucanase activity and manufacturer's recommendation, dose level 2 and 3 were chosen for enzymes. On the other hand, four commercial products were applied at a rate of 1.0 mg/g DM alfalfa hay. One gram DM of alfalfa hay was ground for 10 sec using a Knifetec 1095 sample mill (Foss Tecator, Höganäs, Sweden) and weighed into fermentation bottles (125 ml capacity). All enzymes were resuspended by adding 10 ml of $H_2O$, and appropriate volume of each enzyme was added to corresponding bottles in six replications. Enzymes were applied at 20 h prior to inoculation with ruminal fluid. Three hours later, 40 ml anaerobic buffer medium, prepared as outlined by Goering and Van Soest (1970) and adjusted to pH 6.0 using 1 M trans-aconitic acid (Sigma Chemicals), was added, and the bottles stored at 20° C. overnight. Ruminal fluid was obtained 4 h post feeding (1100 h) from a lactating dairy cow fed a TMR diet composed of barley silage, chopped alfalfa hay, rolled corn grain, and concentrate for early lactation. Strained ruminal fluid was transported to the laboratory in sealed, preheated containers and kept at 39° C. in a water bath. The inoculum was dispensed (10 ml per bottle) into culture bottles that had been warmed to 39° C. in an incubator and flushed with oxygen-free $CO_2$. The bottles were then sealed with a 14 mm butyl rubber stopper plus aluminum crimp cap immediately after loading and incubated for 18 h. Negative controls (ruminal fluid plus buffer alone and ruminal fluid plus buffer and enzyme product) were also incubated. These controls were used to correct for gas release and fermentation residues resulting directly from the inoculum. These treatments and controls were included in 6 replications. Headspace gas produced by substrate fermentation was measured at 2, 6, 12, and 18 h post inoculation by inserting a 23 gauge (0.6 mm) needle attached to a pressure transducer (type T443A, Bailey and Mackey, Birmingham, UK) connected to a visual display (Data Track, Christchurch, UK). The transducer was then removed leaving the needle in place to permit venting. Pressure values, corrected by the amount of substrate OM incubated and for gas release from negative controls, were used to generate volume estimates using the quadratic equation (gas volume=0.18+3.697×gas pressure+0.0824×gas pressure$^2$) reported by Mauricio et al., Anim. Feed Sci. Technol. 79:321-330 (1999). On removal, the bottles were placed in the refrigerator at 4° C. to stop fermentation, and filtered through a commercial coffee filter paper with vacuum application. Apparent DM degradation (DMD) was determined by drying residues at 100° C. for 24 h and OM degradation (OMD) was determined by difference after ashing the dry residues at 500° C. overnight.

The results from the assays are set forth below in Tables 6 and 7. These results demonstrate that xylanases differ in their ractivity in ruminal fluid.

TABLE 6

Effects of xylanase enzyme addition on the cumulative gas production (mL/g OM) on alfalfa hay for 18 h of incubation with ruminal fluid.

| Treatment | Incubation time, h | | | | Ranking[1] |
|---|---|---|---|---|---|
| | 2 | 6 | 12 | 18 | |
| Control | 7.19 | 42.0 | 105.1 | 166.4 | 14 |
| BD2230 | 11.2[c] | 56.5[a] | 124.0[a] | 189.8[a] | 4 |
| BD2236 | 14.8[a] | 64.3[a] | 133.9[a] | 199.5[a] | 2 |
| BD2248 | 12.0[b] | 53.9[a] | 117.5[c] | 179.3 | 9 |
| BD6002 | 11.4[b] | 54.5[a] | 119.1[b] | 183.3[b] | 7 |
| BD6004 | 13.9[a] | 57.7[a] | 122.5[a] | 188.2[a] | 6 |
| BD6405 | 15.4[a] | 60.2[a] | 122.6[a] | 183.2[b] | 8 |
| BD6407 | 12.5[a] | 52.4[b] | 112.4 | 170.7 | 12 |
| BD6890 | 10.0 | 45.9 | 101.4 | 157.0 | 15 |
| BD7150 | 13.6[a] | 52.9[b] | 109.9 | 167.8 | 13 |
| BD7182 | 13.9[a] | 55.1[a] | 114.0 | 173.8 | 11 |
| A | 16.1[a] | 59.6[a] | 119.5[b] | 179.1 | 10 |
| B | 22.7[a] | 73.1[a] | 136.4[a] | 197.7[a] | 3 |
| C | 20.5[a] | 69.1[a] | 130.9[a] | 189.0[a] | 5 |
| D | 24.5[a] | 79.3[a] | 148.5[a] | 210.8[a] | 1 |
| SEM | 0.8 | 1.9 | 2.7 | 3.5 | |

[1]Relative ranking according to the cumulative gas production measured at 18 h of incubation.
[a,b,c]Different from the control within columns at P < 0.001, P < 0.01, and P < 0.05, respectively.

TABLE 7

Effects of xylanase enzyme addition on the apparent degradability of DM (DMD), OM (OMD), and partitioning factor of fermentation (PF) on alfalfa hay after 18 h of incubation with ruminal fluid.

| Treatment | Added activity of xylanase[1] | DMD, % | Rank[2] | OMD, % | Rank[2] | PF[3] | Rank[2] |
|---|---|---|---|---|---|---|---|
| Control | — | 41.1 | 14 | 39.3 | 14 | 2.36 | 4 |
| BD2230 | 874 | 44.2[b] | 5 | 42.5[a] | 5 | 2.24 | 10 |
| BD2236 | 666 | 45.9[a] | 3 | 44.3[a] | 3 | 2.22 | 11 |
| BD2248 | 755 | 43.7[b] | 6 | 42.3[a] | 6 | 2.36 | 4 |
| BD6002 | 1695 | 42.1 | 10 | 40.6 | 10 | 2.22 | 11 |
| BD6004 | 787 | 43.4[c] | 7 | 41.2 | 9 | 2.19[c] | 13 |
| BD6405 | 582 | 40.8 | 15 | 38.9 | 15 | 2.12[b] | 14 |
| BD6407 | 643 | 41.5 | 12 | 39.8 | 12 | 2.33 | 6 |
| BD6890 | 1050 | 47.5[a] | 1 | 45.7[a] | 1 | 2.99[a] | 1 |
| BD7150 | 988 | 41.7 | 11 | 39.8 | 12 | 2.38 | 3 |
| BD7182 | 596 | 41.5 | 12 | 40.1 | 11 | 2.31 | 8 |
| A | 54.5 | 42.3 | 9 | 41.5[c] | 7 | 2.32 | 7 |
| B | — | 43.4[c] | 7 | 41.5[c] | 7 | 2.10[a] | 15 |
| C | 213 | 44.6[a] | 4 | 42.9[a] | 4 | 2.27 | 9 |
| D | 15.1 | 46.3[a] | 2 | 44.4[a] | 2 | 2.41 | 2 |
| SEM |  | 0.6 |  | 0.5 |  | 0.04 |  |

[1]Xylanase activity was expressed as nanomoles of glucose released per minute.
[2]Relative ranking according to DMD, OMD, and FE.
[3]Partitioning factor = mg OM degraded/mL gas produced.
[a,b,c]Different from the control within columns at $P < 0.001$, $P < 0.01$, and $P < 0.05$, respectively.

EXAMPLE 9

Characterization of the Enzyme

Purification from Test Article Material (TAM) (without Separation of the Isoforms)

Preparation of the Xylanase Affinity Column:

Lyophilized xylanase, approximately 10 mg of *Pichia pastoris* produced BD6002 (rXylPP6002, lot Xvl-BD6002-PB206) was resuspended in 1.25 ml distilled water and brought up to 5 mls with 0.1M NaHCO$_3$ pH8.3. This solution was dialyzed against 4 L of 0.1M NaHCO$_3$ for 5.5 hr at 4° C. and then added to distilled water-washed affigel-10 (Bio-Rad) according to the manufacturer's instruction. The xylanase-coupled affigel-10 was poured into a 2 ml column.

Goat Antiserum:

Antibodies to xylanase were generated from purified xylanase protein BD7346 and prepared in goats (American Alpine). The goat was injected with 500 μg of xylanase in complete Freund's adjuvant, were allowed to rest for 3 weeks and then injected with 500 μg of xylanase in incomplete Freund's adjuvant. The goats were bled 10 days after each injection.

Immuno-Affinity Purification of Xylanase Antibodies:

The xylanase affinity column was pre-eluted with 1 ml of 0.1M glycine-HCl pH 2.5 followed by equilibration in phosphate buffered saline, pH 7.3 (PBS). Five mls of goat anti-xylanase serum was applied to the column by gravity. The column was then washed with PBS until baseline was reached. Bound xylanase antibodies were eluted using 1 ml of 0.1M glycine-HCl pH 2.5 followed by PBS. Two ml fractions were collected. Absorbance at 280 nm was recorded for each fraction. The recovered antibodies were dialyzed against 0.1M NaHCO$_3$ pH 8.3.

Preparation of the Goat Anti-Xylanase Affinity Column:

Goat anti-xylanase (~13 mg) was added to distilled water-washed affigel-10 (Bio-Rad) according to the manufacturer's instruction. The xylanase antibody-coupled affigel-10 was poured into a 2 ml column.

Immuno-Affinity Purification of Xylanase:

The xylanase antibody affinity column was pre-eluted with 1 ml of 0.1 M glycine-HCl pH 2.5 followed by equilibration in phosphate buffered saline, pH 7.3 (PBS). One gram of lyophilized *Pichia xylanase* (XYL-PP6002-PD064) was suspended in 5 ml dH$_2$O plus 5 mls PBS and mixed for 30 min at 4° C. The entire suspension was applied to the column by gravity and the unbound solution was collected (flow-through). The column was then washed with PBS until baseline was reached. Bound xylanase was eluted using 1 ml of 0.1M glycine-HCl pH2.5 followed by PBS. Two ml fractions were collected. Absorbance at 280 nm was recorded for each fraction. Fractions containing protein (A280>0.09) were pooled. The flow-through was repeatedly passed over the column until no more xylanase was recovered.

EXAMPLE 10

Protein Concentration of Purified Enzyme

Two different methods were used to measure the concentration of the purified *Pichia xylanase* (XYL-PP6002-PD064). First a BCA protein assay (Pierce Chemicals), was used with Bovine Serum Albumin (BSA) as a reference protein. Two different conditions (37° C., 30 minutes, room temperature for 2 hours) gave very similar results.

The protein concentration was estimated to be 0.403 mg/mL (see below Tables 8 and 9).

TABLE 8

37° C., 30 minutes

| sample | microg/mL | Abs 562 nm | Abs 562 nm | Average Abs | Adjusted abs | Slope $R^2$ |
|---|---|---|---|---|---|---|
| BSA | 0 | 0.0695 | 0.0755 | 0.0725 | 0.0000 | 981.9888 |
| BSA | 5 | 0.0849 | 0.0743 | 0.0796 | 0.0071 | 0.995803 |
| BSA | 25 | 0.0936 | 0.0914 | 0.0925 | 0.0200 | |
| BSA | 125 | 0.2334 | 0.2361 | 0.2348 | 0.1623 | |
| BSA | 250 | 0.4012 | 0.393 | 0.3971 | 0.3246 | |
| BSA | 500 | 0.6718 | 0.6784 | 0.6751 | 0.6026 | |
| BSA | 750 | 0.9008 | 0.9212 | 0.911 | 0.8385 | |
| BSA | 1000 | 1.1868 | 1.206 | 1.1964 | 1.1239 | |
| BSA | 1500 | 1.5761 | 1.6613 | 1.6187 | 1.5462 | |
| BSA | 2000 | 2.0807 | 2.0882 | 2.08445 | 2.0120 | |
| xyn | 407.1653 | 0.4818 | | 0.487133 | 0.414633333 | |
| xyn | | 0.4791 | | | | |
| xyn | | 0.5005 | | | | |

TABLE 9

Room Temperature 2 hours

| sample | microg/mL | Abs 562 nm | Abs 562 nm | Average Abs | Adjusted abs | Slope $R^2$ |
|---|---|---|---|---|---|---|
| BSA | 0 | 0.0596 | 0.0601 | 0.0599 | 0.0000 | 932.3376 |
| BSA | 5 | 0.071 | 0.062 | 0.0665 | 0.0067 | 0.99865 |
| BSA | 25 | 0.0788 | 0.0759 | 0.0774 | 0.0175 | |
| BSA | 125 | 0.2271 | 0.2211 | 0.2241 | 0.1643 | |
| BSA | 250 | 0.3771 | 0.3577 | 0.3674 | 0.3076 | |
| BSA | 500 | 0.6796 | 0.6417 | 0.6607 | 0.6008 | |
| BSA | 750 | 0.928 | 0.8889 | 0.90845 | 0.8486 | |
| BSA | 1000 | 1.1788 | 1.1864 | 1.1826 | 1.1228 | |
| BSA | 1500 | 1.6548 | 1.6566 | 1.6557 | 1.5959 | |
| BSA | 2000 | 2.271 | 2.1562 | 2.2136 | 2.1538 | |
| xyn | 398.3723 | 0.4818 | | 0.487133 | 0.4273 | |
| xyn | | 0.4791 | | | | |
| xyn | | 0.5005 | | | | |

The second method consists of measuring the pixel intensity of protein run in as SDS-PAGE and stained with the protein specific dye SYPRO Tangerine (Invitrogen). Since the *Pichia* produced xylanase contains multiple isoforms in addition to the 20 kD native protein, all bands were selected for Pixel quantitation. Concentration of the enzyme is compared to the standard Carbonic anhydrase that migrates at about 33 kDa. The concentration in the purified xylanase sample is about 0.125 mg/mL.

TABLE 10

| Carbonic Anhydrase micro g/mL | Pixel intensity (mean) | Adjusted |
|---|---|---|
| 1000 | 167.5 | 43.5 |
| 500 | 164.5 | 40.5 |
| 250 | 155 | 31 |
| 125 | 144.23 | 20.23 |
| background | 124 | |

Xylanase PP6002 PD064

| all bands selected lane | Pixel intensity (mean) | Adjusted | Average | Concentration |
|---|---|---|---|---|
| 1 | 136.7 | 18.7 | 20.55 | 125 microgram/mL |
| 2 | 140.4 | 22.4 | | |
| background | 118 | | | |

EXAMPLE 11

Specific Activity of the Purified Enzyme

The antibody purified sample was assayed for its specific activity on wheat arabinoxylan. An aliquot was diluted to about 1000 fold and assayed with the DNS protocol.

This protocol describes a method to measure reducing ends produced during the hydrolysis of carbohydrates, especially xylans and glucans. The assay is based on the reaction of reducing ends with dinitrosalicylic acid (DNS). The DNS assay has several advantages over other reducing sugar assays, such as the Somogyi-Nelson, including a lower detection limit, slightly faster analysis time, and use of less toxic reagents (i.e., sodium arsenate used in Somogyi-Nelson protocol). The method presented here is based on a protocol in Miller G. L. (1959) Anal. Chem. 31 426-428.

Reagents

Use 18 mΩ water for the preparation of all reagents and test solutions 0.4 M Sodium Hydroxide. Dissolve 16.0 g of anhydrous sodium hydroxide (Fisher S318) in 900 mL of water with stirring in a 1 L beaker. Transfer to a 1 L volumetric flask, and adjust volume to 1 L with water. Label and store at 4° C. for not more than 90 days.

DNS Reagent. Dissolve 5.0 g 3,5-dinitrosalicylic acid (Sigma D0550) and 150. g sodium potassium tartrate tetrahydrate (Fisher S387) in 900 ml of 0.4 M Sodium Hydroxide. Transfer to a 1 L volumetric flask and adjust volume to 1 L with 0.4 M Sodium Hydroxide. Filter through 0.2 μm filter. Store at room temperature. Note: this reagent is a yellow-orange color.

200 mM Sodium Acetate Buffer, pH 5.30 (2× SAB). Dissolve 27.2 g of sodium acetate trihydrate (Fisher S209-3) in 900 mL of water with stirring in a 1 L beaker. Adjust pH to 5.30±0.05 with Glacial Acetic Acid (Fisher A38) and transfer to a 1 L volumetric flask. Add 20. mL 2% w/v Sodium Azide in Water and adjust volume to 1 L. Filter through 0.2 μm filter. Label and store at 4° C. Solution is stable for several months.

2% w/v Sodium Azide in Water. Dissolve 2.00 g sodium azide (Sigma S8032) in 90 mL water in a glass beaker with stirring. Transfer to 100 mL volumetric flask. Wash beaker with water and combine in volumetric flask. Bring volume to 100 mL with water.

100 mM Sodium Acetate Buffer, pH 5.30 (1× SAB). Add 500 mL 2× SAB to a 1 L volumetric flask. Adjust volume to 1 L with water. Label and store at 4° C. Solution is stable for several months.

Substrate Solution: 1.40% w/v wheat arabinoxylan in 1× SAB. Accurately weigh 1.40 g wheat arabinoxylan (Megazyme P-WAXYM) into a 120 ml dry pyrex beaker. Wet the sample with 8 mL of 95% ethanol. Add a magnetic stirrer bar followed by 50 mL of 2× SAB and 30 mL of water. Cover and immediately place the slurry on a magnetic stirrer plate with vigorous stirring overnight or until dissolved. Transfer to a 100 mL volumetric flask. Wash the beaker with ~10 mL water and combine with contents of volumetric flask. Adjust volume to 100 mL with water. Label and store at 4° C. Solution is stable for several months.

Xylose Concentrated Stock Solution, 10.0 mg/mL D (+) Xylose in 1× SAB

Dissolve 250.0 mg D (+) xylose (Sigma X1500) in 20 mL 1× SAB in a 50 mL glass beaker with stirring. Transfer solution to 25 mL volumetric flask. Wash beaker with 4 mL 1× SAB and combine in volumetric flask. Adjust volume to 25 mL with 1× SAB.

Xylose Working Stock Solution, 1.00 mg/mL D (+) Xylose in 1× SAB

Add 10.0 mL Xylose Concentrated Stock Solution to 100 mL volumetric flask. Add 1× SAB to 100 mL.

Xylose Standards

Use the table below to prepare the appropriate dilutions for the *Xylose Standards* in 15 mL conicals where Solution A=Xylose Working Stock Solution and Solution B=1× SAB. A positive displacement pipettor should be used to transfer the Solutions A and B. Xylose Standards should be stored at 4° C. between uses.

TABLE 11

| Xylose (μmol) | Volume A (μL) | Volume B (μL) | Total Volume (μL) |
|---|---|---|---|
| 0 | 0 | 500 | 500 |
| 0.20 | 75 | 425 | 500 |
| 0.40 | 150 | 350 | 500 |
| 0.60 | 225 | 275 | 500 |
| 0.80 | 300 | 200 | 500 |
| 1.00 | 375 | 125 | 500 |
| 1.20 | 450 | 50 | 500 |
| 1.33 | 500 | 0 | 500 |

Larger aliquots of Xylose Standards may be prepared and stored at 4° C. for up to 90 days.

Sample Preparation

For those new to the DNS Assay for Measurement of Xylanase Activity, a single vial of control xylanase is prepared as described below. For the interlaboratory cross-over study, five vials of control xylanase are prepared as described below.

Note: Only glassware should be used to prepare xylanase solutions as plasticware has been shown to bind xylanase and decrease activity.

Control Xylanase (Including for Cross-Over Study)

Record the weight of solid contained in the vial (from the label). Add 10.0 g±0.100 g of water to one vial of the control xylanase (lot XYL-PP6002-PD014R) and record the weight. Each vial of Control Xylanase contains 100. mg±1.0 mg of solid. Vortex gently until completely dissolved.

Working Control Xylanase Solution

As very high dilution rates are encountered in this assay, detail to sample preparation is very important. All dilutions are made using 1× SAB. For specific activity determination, make dilutions for each vial of Control Xylanase as described below.

For the initial dilution, weigh ~0.100 g Control Xylanase into a tared 16×100 mm glass tube and record weight. Add ~10 mL of 1× SAB and record weight, generating a 1:100 dilution (see dilution table below).

The second serial dilution is made by weighing ~0.100 g of the 1:100 dilution into a tared 16×100 mm glass tube and record weight. Add ~10 mL of 1× SAB and record weight, generating a 1:10,000 dilution (see dilution table below).

TABLE 12

Serial Dilutions for Control Xylanase

| Starting Dilution | Enzyme Sample | 1× SAB | Final Volume (mL) | Final Dilution |
|---|---|---|---|---|
| Xylanase Standard Stock Solution | 0.100 g | ~10 mL | ~10.0 | ~1:100 |
| 1:100 | 0.100 g | ~10 mL | ~10.0 | ~1:10,000 |

Preparation of Liquid Xylanase Samples

Liquid xylanase samples are without modification used as a stock solution for preparing the Working Xylanase Solution as described below.

Preparation of Solid (e.g., freeze-dried) Xylanase Samples

Add 1.00 mL of water to 100 mg of Solid Xylanase Sample. Vortex gently until completely dissolved.

Working Xylanase Solution for Liquid or Solid Xylanase Samples

Due to variable expected expression levels in non-standard samples, the appropriate dilution rate may vary among samples. Prepare initial dilution (1:100) as described above for Working Control Xylanase Solution.

If desired dilution is between 1:100 and 1:10,000, then prepare a final working dilution and record weights of sample and 1× SAB used for dilution. If desired dilution is higher than 1:10,000, then a 1:10,000 dilution is first prepared as described above for the Working Xylanase Solution. Then, a final working dilution is prepared by weight as above for the Control Xylanase.

Overview of Specific Activity Determination Procedure

For the accurate determination of specific activity using the DNS Assay for Measurement of Xylanase Activity, it is required that each Working Xylanase Solution be tested in triplicate. For this assay protocol, data is taken at 0 and 15 minutes. Note that only a single replicate of the zero time may be sufficient when doing many samples. In this case, 4 data points are generated for each Working Xylanase Solution. Also, it is recommended that the Xylose Standards be included in at least duplicate.

Note: The 0 μg/mL Xylose Standard is also considered to be the Reagent Blank, i.e., this sample represents the background produced by the Substrate Solution alone.

The table below is intended to show how the samples, standards, and control reactions are derived:

TABLE 13

Set-up of Controls, Samples, and Standards

| Reaction | Substrate Solution | 1× SAB | Working Xylanase Solution | Xylose Standard |
|---|---|---|---|---|
| Enzyme + Substrate | 500 μL | — | 200 μL | — |
| Substrate Control | 500 μL | 200 μL | — | — |
| Standard | 500 μL | — | — | 200 μL |

Pipettor Calibration

Measure and record the mass of five 0.2 mL aliquots of 1× SAB delivered to a beaker tared on an analytical balance using a P-1000. The spreadsheet calculates the average mass of a 0.2 mL aliquot of 1× SAB. Use this calibrated P-1000 pipetman to conduct the protocol.

Specific Activity Determination Procedure

Dispense 500 μL aliquots of Substrate Solution into 13×100 mm glass tubes using a positive displacement dispenser with a 5 mL repeat pipettor tip. Reminder: Each enzyme is tested with three replicates for each time point (0 and 15 minutes; therefore, 6 aliquots of substrate are required for each Working Xylanase Solution).

Place tubes containing Substrate Solution in 37° C. water bath for at least 5 minutes.

Aliquot 5 mL of each Working Xylanase Solution to be tested into 16×100 mm glass tube and equilibrate in 37° C. water bath for at least 5 minutes Aliquot 500 μL of each Xylose Standards into 1.5 mL eppendorf tubes and equilibrate in 37° C. water bath for at least 5 minutes.

For the zero time point samples, add 700 μL of DNS Reagent to these tubes using a positive displacement pipettor with a 5 mL tip.

Initiate the reaction by adding 200 μL Working Xylanase Solution to an aliquot of Substrate Solution with a 5 mL repeat pipettor tip. Mix solution by vortexing and return to 37° C. water bath.

Following the initiation of all the enzyme reactions, add 200 μL of Xylose Standards to the appropriately labeled tubes containing Substrate Solution.

At 15 minutes, add 700 μL DNS Reagent to the appropriate-labelled tubes using a positive displacement pipettor with a 5 mL tip and remove from water bath. Vortex vigorously.

After termination of all enzyme reactions, add 700 μL DNS Reagent to each aliquot of Xylose Standard in Substrate Solution and remove samples from bath and vortex vigorously.

Place tubes in vigorously boiling water bath or oil bath for exactly 10 minutes. Note: It is essential that the bath be at exactly 100° C. and that the incubation be exactly 10 minutes.

Remove tubes from boiling water bath and place in a room temperature water bath. Allow to cool at room temperature for at least 5 minutes.

Transfer at least 1 mL of the contents to 1.5 mL polystyrene cuvettes and measure absorbance at 540 nm.

Calculation of Specific Activity

Enter the absorbances for the standards and samples on the appropriate cells in the embedded worksheet. The worksheet automatically generates a xylose standard curve by plotting the absorbance readings ($OD_{540}$) vs. the xylose concentration (μmol/assay). This standard curve is then used to convert the sample absorbances into specific activity using the equation below.

$$\text{Activity intercept} = \frac{DF^*}{(t_2 - t_1) * V_s} \left\{ \left\{ \frac{(OD_{540} sample_{t2})}{\text{slope}} \right\} \left\{ \frac{(OD_{540} sample_{t1})}{\text{slope}} \right\} \right\}$$

$$= \frac{DF^*}{(t_2 - t_1) * V_s} \left\{ \frac{OD_{540} sample_{t2} - OD_{540} sample_{t1}}{\text{slope}} \right\}$$

[ = ] μmoles xylose equivalents/min/g of original enzyme

[ = ] Units/g original undiluted enzyme sample where DF=dilution factor (calculated from First, Second, and Additional Dilutions)

$t_2$=second time point (e.g., 15 minutes)

$t_1$=first time point (e.g., 0 minutes)

$V_s$=sample weight (e.g., 0.2 g)

The results of three independent experiments conducted during three different days is reported in Table 14. The activity for the TAM material PD064 is also reported to compare the two fractions.

TABLE 14

| PP6002 PDO64 lot | unpurified 10 mg/mL | | | Antibody purified | | |
|---|---|---|---|---|---|---|
| | exp 1 | exp 2 | exp 3 | exp 1 | exp 2 | exp 3 |
| Dilution factor | 10100 | 10317 | 10018 | 994 | 955 | 1001 |
| time (min) | 15 | 15 | 15 | 15 | 15 | 15 |
| Absorbance: $OD_{15min} - OD_{0min}$ | 0.957 | 1.003 | 1.035 | 0.697 | 0.731 | 0.683 |
| weight of enzyme in original stock | 0.2 | 0.207 | 0.2 | 0.201 | 0.207 | 0.2 |
| slope (xylose calibration curve) | 0.86 | 0.893 | 0.869 | 0.882 | 0.893 | 0.869 |
| Activity (Units per g) | 3746 | 3731 | 3975 | 262 | 252 | 262 |

Formula used is:

Activity(Units/g)=(dilution factor/time×sample weight)×($OD_{15min}-OD_{0min}$/slope)

The average activity of the purified enzyme is 259 units per gram of enzyme solution, and there is very little variation between experiments. The unpurified lot shows an activity of more than 10 fold higher because its concentration is much higher (10 mg/mL versus 0.400 mg/mL in the purified sample as measured by the BCA method). When one corrects for enzyme concentration, the activity per grams of dry material is now 650 U per mg of solid in the purified fraction, versus 373 U per mg of solid in the TAM sample.

EXAMPLE 12

Optimal Reaction Conditions

The activity of Quantum Xylanase was measured over a broad range of pH values to determine the optimal pH, but also whether the enzyme display significant activity under acidic condition of pH 2 to 3 that mimics conditions in the digestive tract of a monogastric animal.

The PP6002 lot PD064 Quantum® Xylanase (10 mg/mL) was diluted at 1:9187 and submitted to a range of pH conditions from 1.5 to 9. Both reaction conditions and wheat arabinoxylan substrate were prepared in the buffer components indicated below in the Table 15.

TABLE 15

| Reaction pH | Buffer Composition and Concentration |
|---|---|
| 1.5 | 0.031 mHCl + 0.05M KCl |
| 2.0 | 0.01M HCl + 0.05M KCl |
| 2.5 | 0.1M Glycine + 0.1M HCl |
| 3.0 | 0.1M Glycine + 0.1M HCl |
| 3.5 | 0.1M Glycine + 0.1M HCl |
| 4.0 | 0.1M Sodium Acetate |
| 4.5 | 0.1M Sodium Acetate |
| 5.0 | 0.1M Sodium Acetate |
| 5.5 | 0.1M Sodium Acetate |
| 6.0 | 0.1M Tris-HCl |
| 6.5 | 0.1M Tris-HCl |
| 7.0 | 0.1M Tris-HCl |
| 8.0 | 0.1M Tris-HCl |
| 9.0 | 0.1M Tris-HCl |

The enzyme stock (10 mg/mL) was diluted in the pH buffer solution and added to the substrate also prepared in the same buffer. All reactions were conducted at 37 C for 15 min using the DNS protocol. A calibration curve for xylose (in 0.1 M Na Acetate, pH 5.3) was established with a slope of 0.8582, also corrected for an intercept of 0 value. ($R^2$=0.9982). The results are from two experiments and represent the average of 3 absorbance readings, corrected to the t=0 min absorbance (DNS added just prior to reaction).

Figure 5:
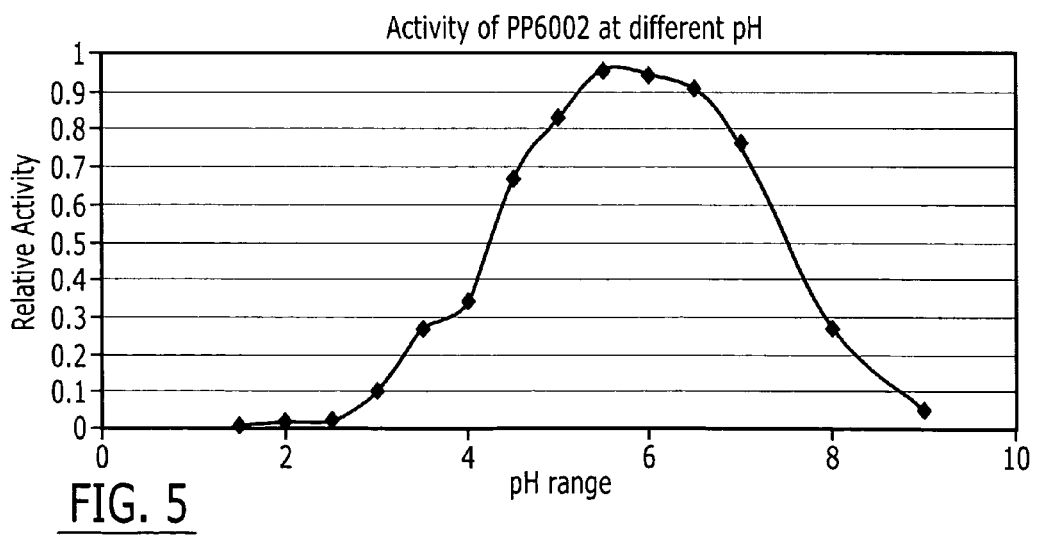
FIG. 5 is a graph of the enzyme activity of *Pichia* expressed xylanase PP6002 compared with pH.

The activity of Quantum® Xylanase is then recorded as a percentage of the value corresponding to the maximum activity, observed here at pH=5.5. At higher pH the activity drops and becomes marginal at pH 9.0 (about 5% of the activity at pH 6.0). There is residual activity at acidic pH, but only 11% at pH=3.0, and none at lower pH (1.5; 2; 2.5). Results in FIG. 5.

EXAMPLE 13

Thermal Tolerance

Thermal Tolerance of Enzyme by ELISA and Activity

The activity of Quantum Xylanase was measured following thermal treatment from 37 to 99° C. with a five degree increment. Solutions of enzyme of 10 mg/mL were prepared in 0.1 M NaOAc pH 5.3 and diluted to 1:100. Samples of 1 mL of 1:100 diluted enzyme were heat rated, then diluted further to 1:10,000 and assayed for activity using the DNS protocol.

Figure 6:
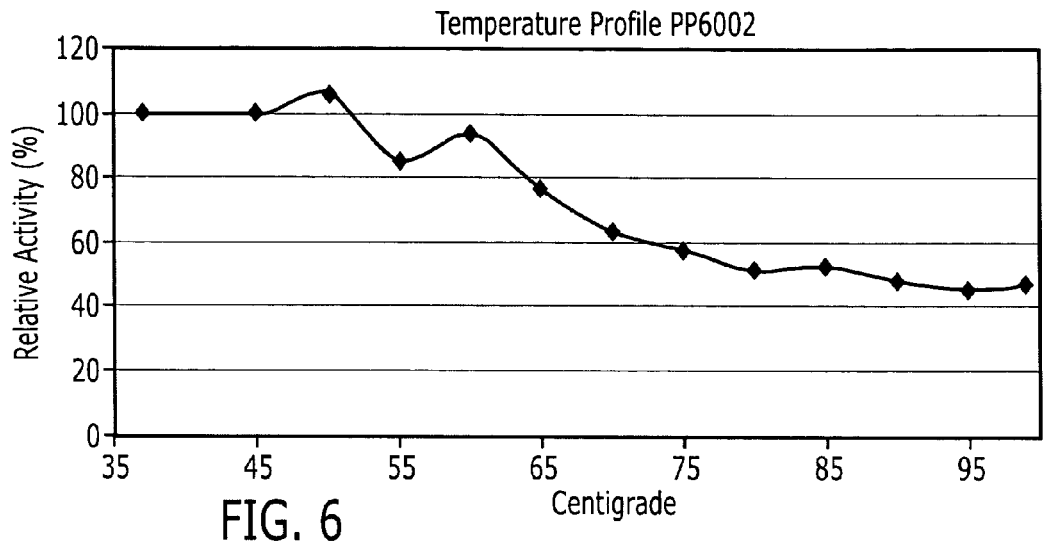
FIG. 6 is a graph of thermal tolerance of PP6002 Quantum® zylanase.

A calibration curve was determined for xylose. The results are shown in FIG. 6 as a percentage of the activity at 37° C. They are the average of two experiments done on two different days. Results in FIG. 6.

PP6002 shows 100% activity until 55 C when it starts to decrease. Then its activity stays above 80% until 65° C., when it drops further down to about 45% at 80° C. Above this temperature the activity remains at the same level. This clearly indicates that PP6002 shows high specific activity at even higher temperatures.

Comparison of Heat Tolerance of Pure Protein with Other Xylanases by Activity

The activity of Quantum xylanase was compared with the activity of *Thermomyces lanuginosus* (Megazyme®), and the *E. coli* produced BD6002 xylanase. Solutions of enzyme of 10 mg/mL were prepared in 0.1 M NaOAc pH.5.3 and diluted to various levels so that the absorbance measurements are in a similar range at the control temperature 37° C.

Figure 7:
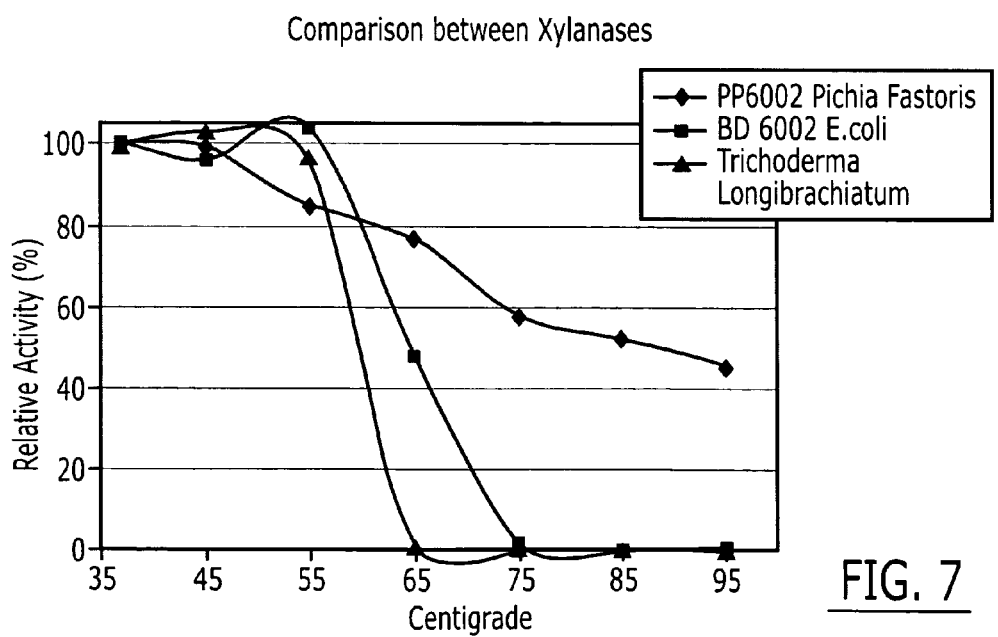
FIG. 7 is a graph comparing the thermostability or thermotolerance of various xylanases.

Temperatures assayed were in the range of 37° C. to 95° C. A calibration curve was determined for xylose. The results are shown in the FIG. 7 as a percentage of the activity at 37° C. As observed above, PP6002 shows some strong specific activity even at high temperature, and it shows more then 40% activity at 95° C.

BD6002 *E. coli* showed 100% activity until 55° C. Above this temperature it drops sharply until no activity is detected at or above 75° C.

A commercial enzyme from *Trichoderma Longibrachiatum* (Megazyme International) also shows no thermotolerance. Its activity droped sharply above 55° C., to no activity above 65° C. These results demonstrate the thermotolerant property of Quantum® Xylanase, when produced in *Pichia pastoris*, and one possibility is that it is related to its isoforms, some of are glycosylation modifications. See FIG. 7 for results.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

Numerous patents, applications and references are discussed or cited within this specification, and all are incorporated by reference in their entireties.

What is claimed is:

1. A feed additive comprising a xylanase encoded by the nucleic acid molecule of SEQ ID NO: 1.

2. The feed additive of claim 1, wherein the feed additive is a liquid.

3. A method of preparing animal feed comprising mixing at least one animal feed component and the feed additive of claim 1.

4. The method of claim 3, wherein the feed additive is a liquid preparation.

5. The method of claim 3, wherein the feed additive is a solid preparation.

6. The method of claim 3, wherein the animal feed component comprises at least one vitamin, mineral, an enzyme other than a thermotolerant xylanase, an organic acid, a probiotic product, an essential oil, sorbitol, a grain processing co-product, glycerol, mono propylene glycol, salts, sugars, preservatives, pH-adjusting agents, or proteins.

7. The method of claim 3, wherein the animal feed is processed by heat treatment, pelleting, extruding, or steam-conditioning.

8. The method of claim 3, wherein one or more of the feed components is selected from the group consisting of wheat, rye, triticale, rice and corn.

9. The method of claim 3, wherein the animal feed is poultry feed, swine feed, or ruminant feed.

10. The method of claim 4, wherein the feed additive is combined with a meal flour.

11. The method of claim 10, wherein the meal flour is soy meal flour.

12. A method of preparing animal feed with hydrolyzed xylan comprising the steps of providing a mixture comprising one or more feed components and a preparation comprising a xylanase encoded by the nucleic acid molecule of SEQ ID NO: 1; and treating the mixture under appropriate conditions of temperature and moisture so as to hydrolyze xylan which is present in the mixture.

* * * * *